United States Patent [19]  [11] Patent Number: 4,638,067
Culbertson et al.  [45] Date of Patent: Jan. 20, 1987

[54] ANTIBACTERIAL AGENTS

[75] Inventors: Townley P. Culbertson, Ann Arbor; John M. Domagala, Canton; Thomas F. Mich, Ann Arbor; Jeffrey B. Nichols, Ypsilanti, all of Mich.

[73] Assignee: Warner-Lambert Co., Morris Plains, N.J.

[21] Appl. No.: 764,357

[22] Filed: Aug. 12, 1985

Related U.S. Application Data

[60] Division of Ser. No. 692,820, Jan. 23, 1985, which is a continuation-in-part of Ser. No. 581,157, Feb. 17, 1984, abandoned, which is a continuation-in-part of Ser. No. 522,275, Aug. 12, 1983, abandoned, which is a continuation-in-part of Ser. No. 416,406, Sep. 9, 1982, abandoned.

[51] Int. Cl.$^4$ .................. C07D 471/04; C07D 401/14; C07D 215/02

[52] U.S. Cl. ..................... 546/15; 546/156; 546/123; 544/70; 540/486; 540/543

[58] Field of Search ............... 544/70; 546/15, 17, 546/18; 260/239 B, 244.4; 574/289, 312, 278, 215

[56] References Cited

U.S. PATENT DOCUMENTS 4,550,103 10/1985 Mich et al. ..................... 574/278
4,550,104 10/1985 Mich et al. ..................... 574/278

*Primary Examiner*—Glennon H. Hollrah
*Assistant Examiner*—D. Dinner
*Attorney, Agent, or Firm*—Ronald A. Daignault

[57] ABSTRACT

Novel naphthyridine-, quinoline- and benzoxazine-carboxylic acids as antibacterial agents are described as well as methods for their manufacture, formulation, and use in treating bacterial infections including the description of certain novel intermediates used in the manufacture of the antibacterial agents.

8 Claims, No Drawings

ANTIBACTERIAL AGENTS

This is a division of application Ser. No. 692,820 filed Jan. 23, 1985, which is a continuation-in-part of U.S. Ser. No. 581,157 filed Feb. 17, 1984, now abandoned, which is a continuation-in-part of U.S. application Ser. No. 522,275 filed Aug. 12, 1983, now abandoned, which is a continuation-in-part of U.S. application Ser. No. 416,406 filed Sept. 9, 1982, now abandoned.

BACKGROUND OF THE INVENTION

U.S. Pat. No. 4,341,784 discloses certain substituted 7-(3-amino-1-1-pyrrolidinyl)-1-ethyl-6-fluoro-1,4-dihydro-4-oxo-1,8-naphthyridine-3-carboxylic acids having the general formula:

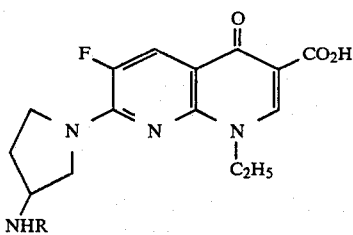

The compounds are disclosed to have antibacterial activity.

The Journal of Medicinal Chemistry, 23, 1358 (1980) discloses certain substituted quinoline-3-carboxylic acids having the structural formula

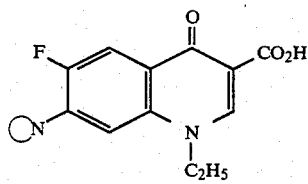

wherein

may be pyrrolidinyl. See also U.S. Pat. No. 4,146,719. The compounds are disclosed to have antibacterial activity.

European Patent Application No. 81 10 6747, Publication No. 047,005, published Mar. 10, 1982, discloses certain benzoxazine derivatives having the structural formula

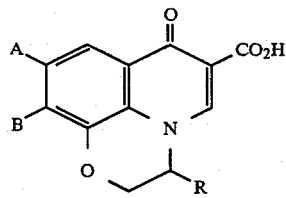

wherein A is halogen and B may be a cyclic amine substituent such as pyrrolidine, or piperidine.

Certain 7-heterocyclic substituted 1,8-naphthyridines are disclosed in Eur. J. Med. Chem. - Chimica Therapeutica, 29, 27 (1977). U.S. Pat. Nos. 3,753,993 and 3,907,808 disclose certain 7-pyridylquinolines.

The references teach that these compounds possess antibacterial activity.

SUMMARY OF THE INVENTION

The invention in a first generic chemical compound aspect is a compound having the structural formula I

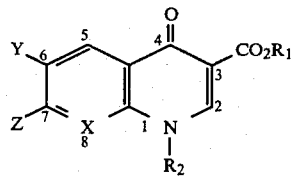

wherein
Z is

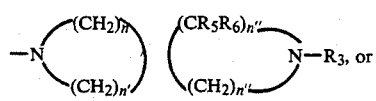

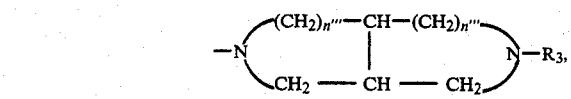

in which
Z' is

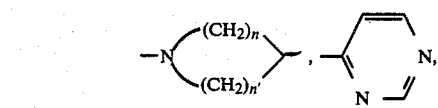

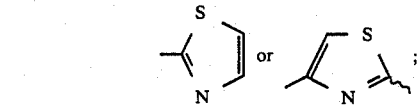

X is CH, CCl, CF, C—OH, CO-alkyl having from one to three carbon atoms, C—NH—alkyl having from one to three carbon atoms or N;

Y is hydrogen, fluorine, chlorine, or bromine;

n is 1, 2, 3, or 4;

n' is 1, 2, 3, or 4 wherein $n+n'$ is a total of 2, 3, 4, or 5;

n'' is 0, 1, or 2, and n''' is 1, or 2;

$R_1$ is hydrogen, alkyl having from one to six carbon atoms or a cation;

$R_2$ is alkyl having from one to four carbon atoms, vinyl, haloalkyl, or hydroxyalkyl having from two to four carbon atoms, or cycloalkyl having three to six carbon atoms;

$R_3$ is hydrogen, alkyl having from one to four carbon atoms or cycloalkyl having three to six carbon atoms;

$R_4$ is hydrogen, alkyl from one to four carbon atoms, hydroxyalkyl having two to four carbon atoms, trifluoroethyl or $R_7CO—$ wherein $R_7$ is alkyl having from one to four carbon atoms, or alkoxy having from one to four carbon atoms, with the proviso that when X is N and Z is

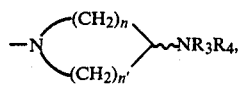

in which
n+n' is 3,
R$_3$ is cycloalkyl having three to six carbon atom, or R$_3$ is alkyl from one to four carbon atoms and R$_4$ is alkyl from one to four carbon atoms, hydroxyalkyl having two to four carbon atoms or trifluoroethyl;
R$_5$ is hydrogen, or alkyl having from one to three carbon atoms;
R$_6$ is hydrogen or alkyl having from one to three carbon atoms;
where
X is C—OH said hydrogen of C—OH and said R$_2$ of N—R$_2$ may be displaced by the ring forminq radical

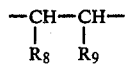

wherein
R$_8$ is hydrogen or an alkyl group of one to three carbon atoms and
R$_9$ is hydrogen or an alkyl group of one to three carbon atoms,
R$_9$ is hydrogen or an alkyl group of one to three carbon atoms,
and the pharmaceutically acceptable acid addition or gase salts thereof.

The significance of the symbol ~ is intended only to show point of attachment of the radical to other atoms to the remaining component of the molecule.

Compounds where X is C—OH wherein said hydrogen and said R$_2$ of NR$_2$ are displaced by the ring forming radical

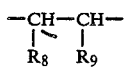

have the following formula:

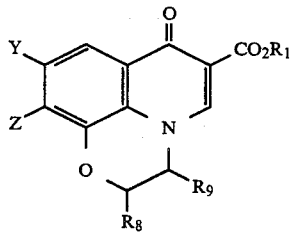

Ia

The preferred compounds of this invention are those wherein Z' is

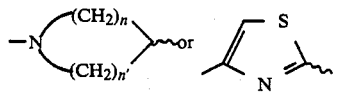

Also preferred compounds of this invention are those wherein Z is

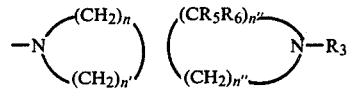

Other preferred compounds of this invention are those wherein Y is fluorine.

Other preferred compounds of this invention are those wherein X is N, CH, or C—F.

Other preferred compounds of this invention are those cyclic derivatives wherein C—O is linked to the 1-nitrogen by the —CHR$_8$CHR$_9$ radical, and R$_8$ and R$_9$ are each hydrogen or methyl.

Other preferred compounds of this invention are those wherein R$_1$ is hydrogen or a pharmaceutically acceptable base salt such as a metal or amine salt.

Other preferred compounds of this invention are those wherein R$_2$ is ethyl, vinyl, or 2-fluoroethyl.

Other preferred compounds of this invention are those wherein n" is one, R$_3$ is hydrogen, methyl, ethyl, or n-propyl, and R$_4$, R$_5$, and R$_6$ are hydrogen.

The most preferred compounds are those wherein X is N or CF, Z is

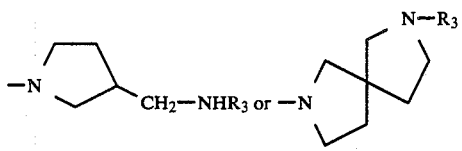

R$_1$ is hydrogen, R$_2$ is ethyl, vinyl, or 2-fluoroethyl, and R$_3$ is hydrogen, methyl, ethyl, 1- or 2-propyl, or a pharmaceutically acceptable acid addition or base salt thereof.

Additionally, most preferred compounds include those wherein Y is fluorine; X is CF; R$_2$ is cyclopropyl; Z is

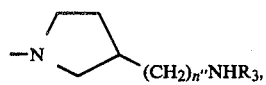

in which n" is 0 or 1 and R$_3$ is hydrogen, methyl, ethyl, 1- or 2-propyl, and R$_1$ is hydrogen or a pharmaceutically acceptable base salt thereof.

Most preferred compounds also include those wherein Y is fluorine; X is N; R$_2$ is cyclopropyl; Z is

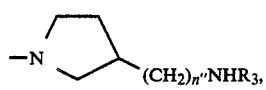

in which n" is 0 or 1 and R$_3$ is hydrogen, methyl, ethyl, 1- or 2-propyl, and R$_1$ is hydrogen or a pharmaceutically acceptable base salt thereof.

Particularly preferred species of the invention are the compounds having the names:
7-[3-(aminomethyl)-1-pyrrolidinyl]-1-ethyl-6-fluoro-1,4-dihydro-4-oxo-1,8-naphthyridine-3-carboxylic acid;
7-[3-(aminomethyl)-1-pyrrolidinyl]-1-ethyl-6,8-difluoro-1,4-dihydro-4-oxo-3-quinolinecarboxylic acid;

7-[3-(aminomethyl)-1-pyrrolidinyl]-6,8-difluoro-1-(2-fluoroethyl)-1,4-dihydro-4-oxo-3-quinolinecarboxylic acid;

7-[3-(aminomethyl)-1-pyrrolidinyl]-6,8-difluoro-1-ethenyl-1,4-dihydro-4-oxo-3-quinolinecarboxylic acid;

1-ethyl-7-[3-[(ethylamino)methyl]-1-pyrrolidinyl]-6-fluoro-1,4-dihydro-4-oxo-1,8-naphthyridine-3-carboxylic acid;

1-ethyl-7-[3-[(ethylamino)methyl]-1-pyrrolidinyl]-6,8-difluoro-1,4-dihydro-4-oxo-3-quinolinecarboxylic acid;

7-[3-[(ethylamino)methyl]-1-pyrrolidinyl]-6,8-difluoro-1-(2-fluoroethyl)-1,4-dihydro-4-oxo-3-quinolinecarboxylic acid;

7-[3-[(ethylamino)methyl]-1-pyrrolidinyl]-6,8-difluoro-1-ethenyl-1,4-dihydro-4-oxo-3-quinolinecarboxylic acid;

1-ethyl-6-fluoro-1,4-dihydro-7-[3-[[(1-methylethyl)amino]methyl]-1-pyrrolidinyl]-4-oxo-1,8-naphthyridine-3-carboxylic acid;

1-ethyl-7-[3-[[(1-methylethyl)amino]methyl]-1-pyrrolidinyl]-6,8-difluoro-1,4-dihydro-4-oxo-3-quinolinecarboxylic acid;

9-fluoro-2,3-dihydro-3-methyl-10-(7-methyl-2,7-diazaspiro[4.4]non-2-yl)-7-oxo-7H-pyrido[1,2,3-de]-1,4-benzoxazine-6-carboxylic acid;

1-ethyl-6-fluoro-1,4-dihydro-7-(7-methyl-2,7-diazaspiro[4.4]non-2-yl)-4-oxo-1,8-naphthyridine-3-carboxylic acid;

1-ethyl-6,8-difluoro-1,4-dihydro-7-(7-ethyl-2,7-diazaspiro[4.4]non-2-yl)-4-oxo-3-quinolinecarboxylic acid;

1-ethyl-6,8-difluoro-1,4-dihydro-7-(7-methyl-2,7-diazaspiro[4.4]non-2-yl)-4-oxo-3-quinolinecarboxylic acid;

7-(3-amino-1-pyrrolidinyl)-1-ethyl-6,8-difluoro-1,4-dihydro-4-oxo-3-quinolinecarboxylic acid;

7-(3-amino-1-azetidinyl)-1-ethyl-6-fluoro-1,4-dihydro-4-oxo-1,8-naphthyridine-3-carboxylic acid;

7-[3-(aminomethyl)-1-pyrrolidinyl]-1-cyclopropyl-6,8-difluoro-1,4-dihydro-4-oxo-3-quinolinecarboxylic acid;

1-cyclopropyl-7-[3-[(ethylamino)methyl]-1-pyrrolidinyl]-6,8-difluoro-1,4-dihydro-4-oxo-3-quinolinecarboxylic acid;

7-[3-amino-1-pyrrolidinyl]-1-cyclopropyl-6,8-difluoro-1,4-dihydro-4-oxo-3-quinolinecarboxylic acid;

1-cyclopropyl-7-[3-[(methylamino)methyl]-1-pyrrolidinyl]-6,8-difluoro-1,4-dihydro-4-oxo-3-quinolinecarboxylic acid;

1-cyclopropyl-7-[3-(ethylamino)-1-pyrrolidinyl]-6,8-difluoro-1,4-dihydro-4-oxo-3-quinolinecarboxylic acid;

1-cyclopropyl-6,8-difluoro-1,4-dihydro-7-[3-[[(1-methylethyl)amino]methyl]-1-pyrrolidinyl]-4-oxo-3-quinolinecarboxylic acid;

7-[3-(aminomethyl)-1-pyrrolidinyl]-1-cyclopropyl-1,4-dihydro-6-fluoro-4-oxo-1,8-naphthyridine-3-carboxylic acid;

1-cyclopropyl-7-[3-[(ethylamino)methyl]-1-pyrrolidinyl]-1,4-dihydro-6-fluoro-4-oxo-1,8-naphthyridine-3-carboxylic acid;

7-[3-amino-1-pyrrolidinyl]-1-cyclopropyl-1,4-dihydro-6-fluoro-4-oxo-1,8-naphthyridine-3-carboxylic acid;

and the pharmaceutically acceptable acid addition or base salts thereof.

The invention also includes in a second generic chemical compound aspect compounds having the following structural formulae

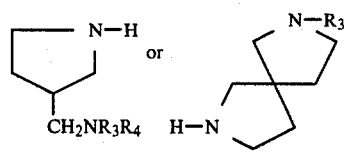

II     IIa wherein $R_3$ and $R_4$ are defined hereinabove, with the proviso that $R_3$ cannot be hydrogen; and the acid addition salts thereof.

The invention further includes as particular species of its second generic chemical compound aspect the intermediate compounds having the names ethyl [(3-pyrrolidinyl)methyl]carbamate, N-ethyl- and N-methyl-3-pyrrolidinemethanamine, 2-methyl- and 2-ethyl-2,7-diazaspiro[4.4]nonane and the acid addition salts thereof.

The following process for preparing compounds of the formula $$\underset{R_2}{\underset{|}{\text{III}}}$$

wherein $R_1$, $R_2$, X, Y, and Z are as defined for formula I which comprises reacting a compound having the following structural formula

IV

V with an amine corresponding to the group Z wherein Z is the compound having the structural formula

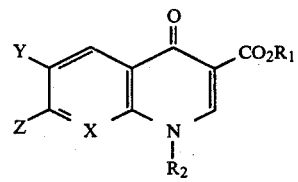

VIa

VIb

-continued

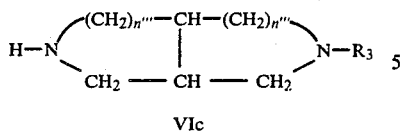

VIc wherein all of the above terms are as defined in formula I and L is a leaving group which is preferably fluorine or chlorine.

The invention also includes a pharmaceutical composition which comprises an antibacterially effective amount of a compound having structural formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural formula III may be readily prepared by treating a corresponding compound having the structural formula IV or V with the desired cyclic amine VIa, VIb, or VIc. For purposes of this reaction, the alkylamine substituent of Compound VIa, VIb, or VIc may, if desired, be protected by a group which renders it substantially inert to the reaction conditions. Thus, for example, protecting groups such as the following may be utilized:

carboxylic acyl groups such as formyl, acetyl, trifluoroacetyl;

alkoxycarbonyl groups such as ethoxycarbonyl, t-butoxycarbonyl, $\beta,\beta,\beta$-trichloroethoxycarbonyl, $\beta$-iodoethoxycarbonyl;

aryloxycarbonyl groups such as benzyloxycarbonyl, p-methoxybenzyloxycarbonyl, phenoxycarbonyl;

silyl groups such trimethylsilyl;

and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound IV or V and Compound VIa, VIb, or VIc if desired, by procedures known to those skilled in tne art. For example, the ethoxycarbonyl group may be removed by acid or base hydrolysis and the trityl group may be removed by hydrogenolysis.

The reaction between the compound of structural formula IV or V and a suitably protected compound of formula VIa, VIb, and VIc may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of formula VI may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, III. Alternatively, the protecting group $R_4$ need not be removed.

The starting compounds having structural formulae IV and V are known in the art or, if new, may be prepared from known starting materials by standard procedures or by variations thereof. Thus the following compounds are disclosed in the noted references:

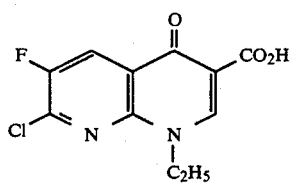

European Patent Application 80 40 1369

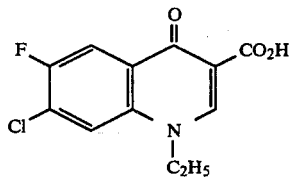

J. Med. Chem., 23, 1358 (1980)

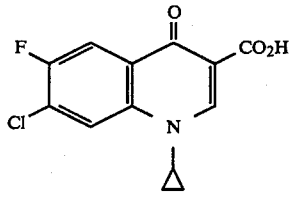

European Patent Application 0078362

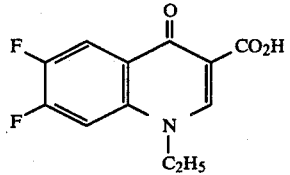

European Patent 0 000 203 (1979)

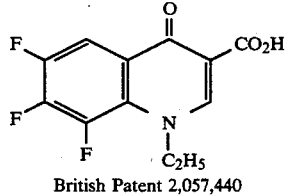

British Patent 2,057,440

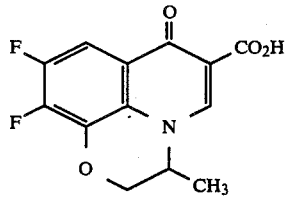

European Patent Application 81 10 6747

1-Cyclopropyl-6,7,8-trifluoro-1,4-dihydro-4-oxo-3-quinolinecarboxylic acid may be prepared by a series of reactions starting from 2,3,4,5-tetrafluorobenzoic acid. The sodium salt of 2,3,4,5-tetrafluorobenzoic acid is reacted with oxalyl chloride and the product condensed with diethyl malonate in the presence of magnesium turnings to afford after hydrolysis 2,3,4,5-tetrafluorobenzoylacetic acid, ethyl ester. This compound is, in turn, treated with triethylorthoformate and acetic anhydride, followed by cyclopropylamine to afford 2-(2,3,4,5-tetrafluorobenzoyl)-2-cyclopropylaminoacrylic acid, ethyl ester, which is then ring closed and hydrolysed with sodium hydride to give the desired intermediate.

7-Chloro-1-cyclopropyl-6-fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3-carboxylic acid can be converted to the 7-hydroxy derivative with a mixture of nitric and sulfuric acids which is then replaced by chlorine by treatment with phosphorus oxychloride to give the desired intermediate. The synthesis of both of the above N-cyclopropyl intermediates is described in the Preparative Examples.

The compounds of the invention having structural formula VIa, VIb, or VIc are either known compounds or they may be prepared from known starting materials by standard procedures or by variations thereof. For example, 3-pyrrolidinemethanamines having the structural formula D

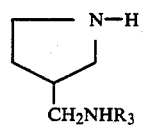

may be readily prepared from the known starting material methyl 5-oxo-1-(phenylmethyl)-3-pyrrolidinecarboxylate, A, [J. Org. Chem., 26, 1519 (1961)] by the following reaction sequence.

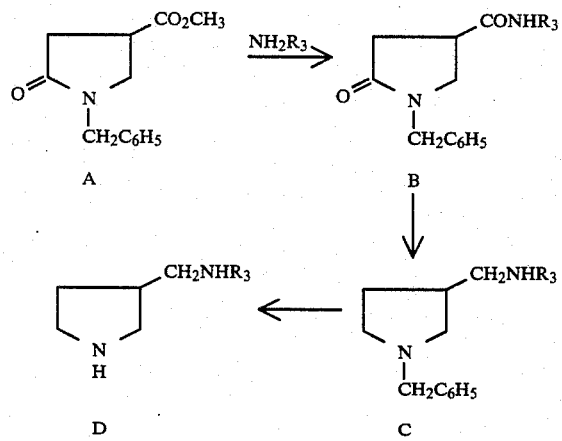

The compound wherein $R_3$ is hydrogen, namely 3-pyrrolidinemethanamine, has been reported in J. Org. Chem., 26, 4955 (1961).

Thus Compound A may be converted to the corresponding amide B by treatment with $R_3NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R=H in C, the primary amine function may be protected with a group $R_4$ as defined, hereinabove. For example, the primary amine function may be acylated with an acyl halide such as acetyl chloride by well known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example as described above for Compound C, thereby producing Compound D where R is $-CO_2Et$, which after conversion to a compound of the type VIa or VIb may be reacted with a compound having the structural formula IV or V to thereby produce a corresponding compound having the structural formulae I or Ia. The $-CO_2Et$ group may be removed by standard procedures.

Likewise spiroamino compounds represented by structural formula VIb may be readily prepared from the known starting material 3-ethoxycarbonyl-5-oxo-3-pyrrolidineacetic acid ethyl ester [J. Org. Chem., 46, 2757 (1981)] by the following reaction sequence.

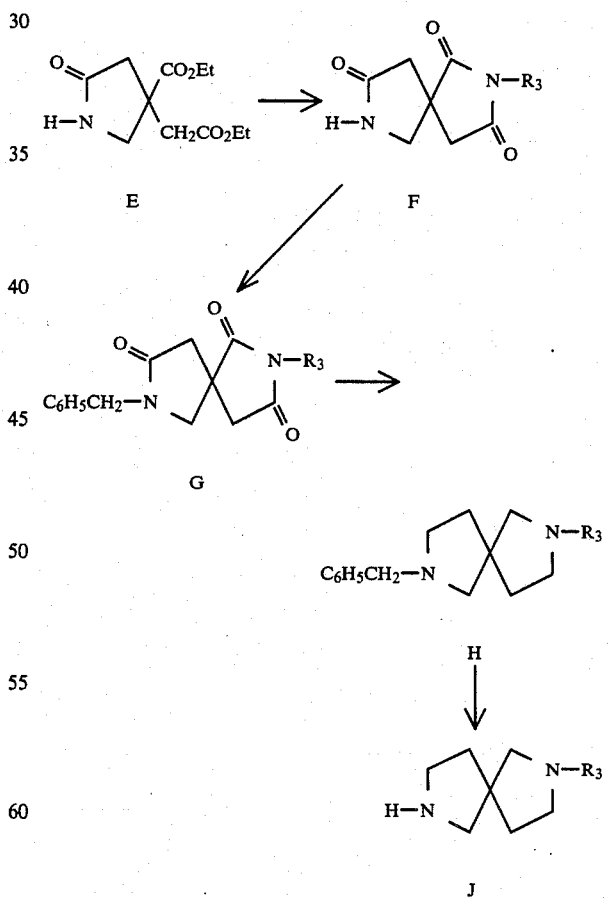

The compound 2,7-diazaspiro [4.4]nonane where $R_3$ is H is described in the above reference. Thus Compound E may be converted to the corresponding amide F by treatment with $R_3NH_2$, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The invention also relates to a process for preparing compounds of the invention of the formula

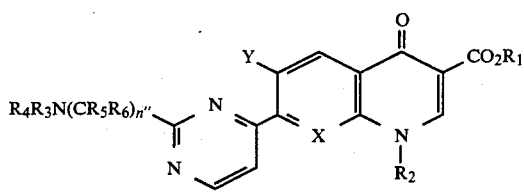

Ib which comprises reacting a compound having structural formula

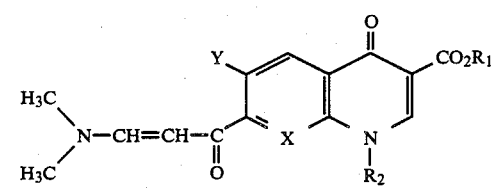

VII with an amidine having structural formula

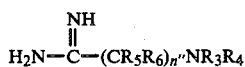

VIII wherein X, Y, $R_1$–$R_6$, and $n''$ are defined for formula I.

In addition, the invention also relates to a process for preparing a compound having structural formula

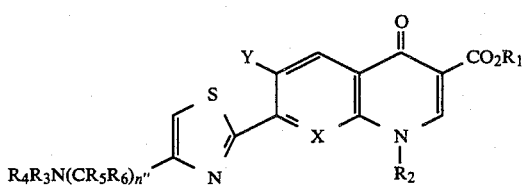

Ic which comprises: (a) reacting a compound having the structural formula

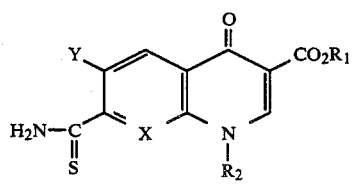

IX with a dihalo ketone of the formula

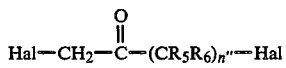

wherein X, Y, R, $R_2$, $R_5$, and $R_6$ are defined for formula I; $n''$ is 1 or 2, and Hal is any convenient halogen, preferably chlorine, to produce the halomethylthiazole;

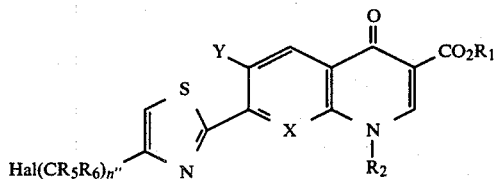

X (b) displacing the halogen atom of X with an amino group of the formula $R_3R_4N$— or with axide ion; (c) reducing the azide group to produce the compound Ic wherein $R_3$ and $R_4$ are hydrogen; and (d) optionally alkylating the primary amino function to produce compounds Ic wherein $R_3$ and/or $R_4$ are alkyl of from one to three carbon atoms.

The final process of this invention is for preparing compounds of the structural formula

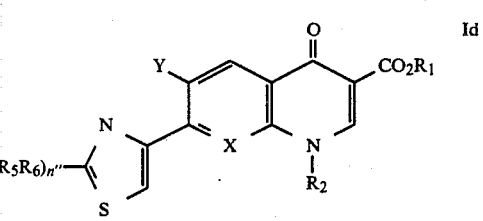

Id which comprises reacting a compound having the structural formula

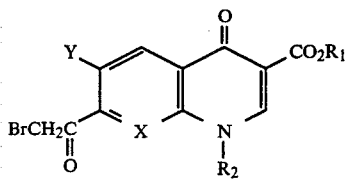

XI with a thioamide having structural formula XII

XII wherein X, Y, $R_1$–$R_6$, and $n''$ are defined as in formula I.

The compound of the invention having structural formula I wherein Z is

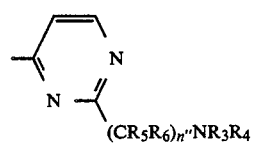

may be prepared from the correspondingly substituted methyl ketone

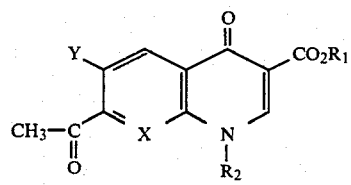

wherein X, Y, $R_1-R_6$, and n" are defined above. Thus compound XIII may be treated with t-butoxy-bisdimethylaminomethane to give a compound having the structural formula XIV

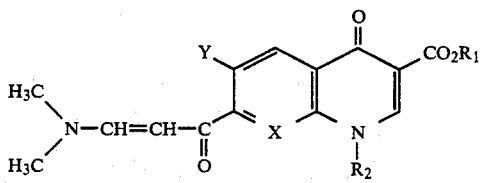

This reaction may be carried out by mixing the two reactants in a nonreactive solvent such as dimethylformamide at an elevated temperature.

Compound XIV may then be reacted with any of a variety of substituted amidines having the structural formula

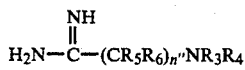

wherein $R_1-R_6$ and n" are defined as in formula I to produce the correspondingly substituted pyrimidines. This reaction may be carried out by mixing the two reactants in an inert solvent such as t-butanol in the presence of a base such as potassium t-butoxide at elevated temperature. Variations in these reactions, for example to maximize a particular yield is within the skill of the art.

The compounds of the invention having structural formula I wherein Z is

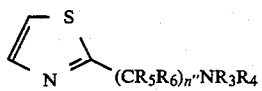

may also be prepared from the correspondingly substituted methyl ketone XIII. Thus, compound XIII is first brominated to produce the α-bromoketone, XVI.

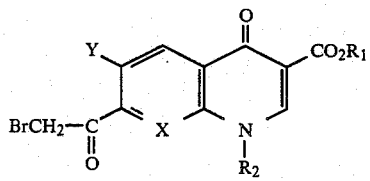

This reaction may be carried out by treating compound XIII with potassium bromate and hydrobromic acid in a nonreactive solvent such as acetic acid. Compound XVI is then reacted with any of a variety of thioamides having structural formula

wherein $R_1-R_6$ and n" are defined above to produce the correspondingly substituted 2-(substituted)-thiazol-4-yl compounds. This reaction may be carried out by mixing Compounds XVI and XVII in a nonreactive solvent such as ethanol or dimethylformamide usually at room temperature. Variations in these reactions, for example, to maximize a particular yield is within the skill of the art.

The compounds of the invention having structural formula I wherein Z is

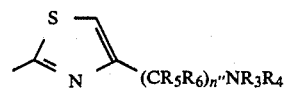

may be prepared from the correspondingly substituted thioamide

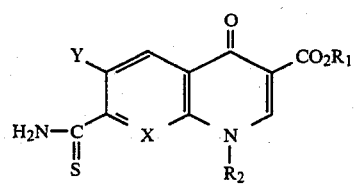

by first reacting XVIII with a dihaloketone

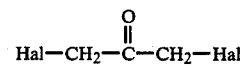

to produce the halomethylthiazole

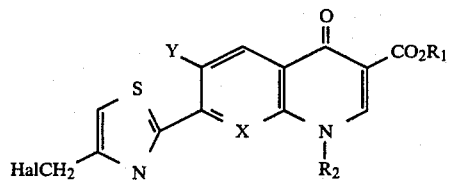

In the preferred procedure, 1,3-dichloroacetone is mixed with XVIII in a nonreactive solvent such as N,N-dimethylformamide and heated to about 100° C. for approximately four hours. The product XIX wherein Hal represents chlorine, may be isolated and purified by standard procedures. This compound is then treated with azide ion, preferably sodium azide, in a convenient nonreactive solvent such as N,N-dimethylformamide by heating at about 100° C. for about four hours. The thus produced azido compound

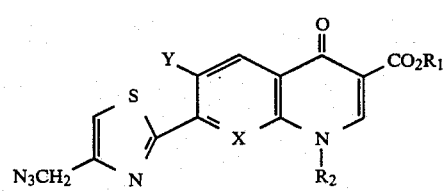

may then be reduced to produce the corresponding primary amine Ic where $R_3$, $R_4$, $R_5$, and $R_6$ are hydrogen. In the preferred procedure, the azide is dissolved in acetic acid and treated with hydrogen gas at atmospheric pressure using a 10% palladium on carbon catalyst. The corresponding secondary and tertiary amines may be produced by reacting XIX with the appropriate amine. When Z is VIa, VIb, or VIc in formula I, compounds where $R_2$ is cycloalkyl may be prepared by methods outlined in U.S. Pat. No. 4,359,578 or by the method described in European Patent Publication No. 00078362.

Compounds of formulae Ia where Z is

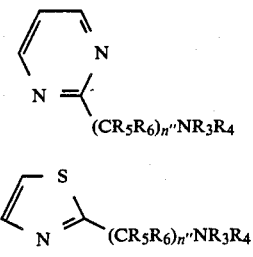

may be prepared by methods described above for compounds of the formula Ib and Id starting with a methyl ketone of the formula

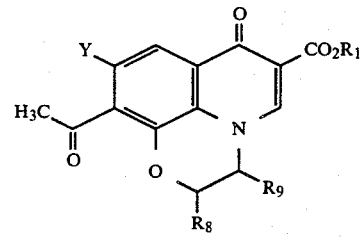

wherein $R_1$, $R_8$, $R_9$, and Y have been defined above.

The compounds of the invention display antibacterial activity when tested by the microtitration dilution method as described in Heifetz, et al, Antimicr. Agents & Chemoth., 6, 124 (1974), which is incorporated herein by reference.

By use of the above referenced method, the followed minimum inhibitory concentration values (MICs in μg/ml) were obtained for representative compounds of the invention and the prior art compound 7-(3-amino-1-pyrrolidinyl)-1-ethyl-6-fluoro-1,4-dihydro-4-oxo-1,8-naphthyridine-3-carboxylic acid designated as ** in the table.

IN VITRO ANTIBACTERIAL ACTIVITY
Minimal Inhibitory Concentration
MIC (μg/ml)

| Organisms | ** | Compound Ex. 1 | Compound Ex. 2 | Compound Ex. 3 | Compound Ex. 4 | Compound Ex. 5 |
|---|---|---|---|---|---|---|
| Enterobacter cloacae MA 2646 | 0.05 | 0.05 | 0.2 | 0.2 | 0.4 | 0.8 |
| Escherichia coli Vogel | 0.013 | 0.05 | 0.025 | 0.025 | ≦0.1 | 0.2 |
| Klebsiella pneumoniae MGH-2 | 0.05 | 0.1 | 0.2 | 0.2 | 0.8 | 0.8 |
| Proteus rettgeri M 1771 | 0.05 | 0.2 | 1.6 | 1.6 | 3.1 | 3.1 |
| Pseudomonas aeruginosa UI-18 | 0.05 | 0.1 | 0.4 | 1.6 | 6.3 | 6.3 |
| Staphylococcus aureus H 228 | 0.8 | 0.1 | 0.2 | 0.2 | 1.6 | 0.4 |
| Staphylococcus aureus UC-76 | 0.025 | 0.003 | 0.025 | 0.003 | 0.1 | ≦0.1 |
| Streptococcus faecalis MGH-2 | 1.6 | 0.025 | 0.4 | 0.2 | 1.6 | 0.8 |
| Streptococcus pneumoniae SV-1 | 0.4 | 0.013 | 0.2 | 0.1 | 0.4 | 0.2 |
| Streptococcus pyogenes C-203 | 0.4 | 0.013 | 0.2 | 0.05 | 1.6 | 0.4 |

| Organisms | Compound Ex. 6 | Compound Ex. 7 | Compound Ex. 8 | Compound Ex. 9 | Compound Ex. 10 | Compound Ex. 10a |
|---|---|---|---|---|---|---|
| Enterobacter cloacae MA 2646 | 0.2 | 1.6 | 1.6 | 0.4 | ≦0.1 | 0.2 |
| Escherichia coli Vogel | 0.2 | 0.4 | 0.2 | 0.1 | ≦0.1 | 0.2 |
| Klebsiella pneumoniae MGH-2 | 0.8 | 1.6 | 1.6 | 0.8 | 0.4 | 0.8 |
| Proteus rettgeri M 1771 | 3.1 | 3.1 | 6.3 | 1.6 | 0.4 | 0.8 |
| Pseudomonas aeruginosa UI-18 | 6.3 | 0.8 | 1.6 | 3.1 | 0.2 | 0.8 |
| Staphylococcus aureus H 228 | 1.6 | 0.8 | 0.8 | 0.4 | ≦0.1 | 0.4 |
| Staphylococcus aureus UC-76 | 0.8 | 0.05 | 0.013 | 0.05 | ≦0.1 | ≦0.1 |
| Streptococcus faecalis MGH-2 | 3.1 | 0.4 | 1.6 | 0.2 | ≦0.1 | ≦0.1 |
| Streptococcus pneumoniae SV-1 | 0.4 | 0.2 | 0.4 | 0.2 | ≦0.1 | 0.4 |
| Streptococcus pyogenes C-203 | 1.6 | 0.05 | 0.1 | 0.1 | ≦0.1 | ≦0.1 |

| Organisms | Compound Ex. 11 | Compound Ex. 11a | Compound Ex. 12 | Compound Ex. 12a | Compound Ex. 12b | Compound Ex. 13 |
|---|---|---|---|---|---|---|
| Enterobacter cloacae MA 2646 | 0.1 | 0.2 | 0.4 | 3.1 | 0.8 | 3.1 |
| Escherichia coli Vogel | 0.05 | ≦0.1 | 0.2 | 1.6 | 0.2 | 0.8 |
| Klebsiella pneumoniae MGH-2 | 0.1 | 0.4 | 0.4 | 6.3 | 0.4 | 3.1 |
| Proteus rettgeri M 1771 | 0.2 | 0.8 | 0.8 | 6.3 | 0.8 | 12.5 |
| Pseudomonas aeruginosa UI-18 | 0.8 | 1.6 | 1.6 | 12.5 | 1.6 | 3.1 |
| Staphylococcus aureus H 228 | 0.013 | 0.4 | 0.4 | ≦0.1 | ≦0.1 | 3.1 |
| Staphylococcus aureus UC-76 | 0.003 | ≦0.1 | ≦0.1 | ≦0.1 | ≦0.1 | 0.8 |
| Streptococcus faecalis MGH-2 | 0.013 | 0.2 | ≦0.1 | 0.8 | ≦0.1 | 1.6 |
| Streptococcus pneumoniae SV-1 | 0.013 | ≦0.1 | ≦0.1 | 1.6 | ≦0.1 | 3.1 |
| Streptococcus pyogenes C-203 | 0.013 | ≦0.1 | ≦0.1 | 0.8 | ≦0.1 | 0.4 |

| Organisms | Compound Ex. 14 | Compound Ex. 16 | Compound Ex. 17 | Compound Ex. 17a | Compound Ex. 17b | Compound Ex. 18 |
|---|---|---|---|---|---|---|
| Enterobacter cloacae MA 2646 | 3.1 | ≦0.1 | 1.6 | 0.4 | 1.6 | 0.1 |
| Escherichia coli Vogel | 0.8 | ≦0.1 | 0.8 | 0.8 | 0.4 | 0.2 |
| Klebsiella pneumoniae MGH-2 | 3.1 | 0.4 | 1.6 | 1.6 | 3.1 | 0.4 |

IN VITRO ANTIBACTERIAL ACTIVITY
Minimal Inhibitory Concentration
MIC (μg/ml)

-continued

| Organisms | | | | | | |
|---|---|---|---|---|---|---|
| Proteus rettgeri M 1771 | 6.3 | 1.6 | 6.3 | 6.3 | 3.1 | 0.8 |
| Pseudomonas aeruginosa UI-18 | 6.3 | 0.4 | 1.6 | 3.1 | 6.3 | 0.8 |
| Staphylococcus aureus H 228 | 1.6 | 0.4 | 0.2 | 1.6 | 1.6 | 0.2 |
| Staphylococcus aureus UC-76 | 0.05 | 0.2 | ≦0.1 | 0.2 | 0.2 | 0.006 |
| Streptococcus faecalis MGH-2 | 0.8 | 1.6 | 0.2 | 3.1 | 3.1 | 0.1 |
| Streptococcus pneumoniae SV-1 | 0.4 | 3.1 | 1.6 | 3.1 | 6.3 | 0.025 |
| Streptococcus pyogenes C-203 | 0.4 | 3.1 | 0.8 | 1.6 | 3.1 | 0.006 |

| Organisms | Compound Ex. 19 | Compound Ex. 20 | Compound Ex. 22 | Compound Ex. 23 | Compound Ex. 24 | Compound Ex. 24a |
|---|---|---|---|---|---|---|
| Enterobacter cloacae MA 2646 | 0.2 | 0.2 | 0.8 | 0.2 | 0.4 | 25 |
| Escherichia coli Vogel | 0.1 | 0.1 | 0.8 | ≦0.1 | 0.1 | 12.5 |
| Klebsiella pneumoniae MGH-2 | 0.4 | 0.4 | 3.1 | 0.2 | 0.4 | 25 |
| Proteus rettgeri M 1771 | 3.1 | 0.4 | 12.5 | 1.6 | 1.6 | 100 |
| Pseudomonas aeruginosa UI-18 | 0.8 | 0.8 | 0.8 | 0.8 | 1.6 | 50 |
| Staphylococcus aureus H 228 | 0.4 | 0.2 | 3.1 | ≦0.1 | 0.1 | 6.3 |
| Staphylococcus aureus UC-76 | 0.006 | 0.006 | 0.4 | ≦0.1 | 0.025 | 3.1 |
| Streptococcus faecalis MGH-2 | 0.1 | 0.05 | 1.6 | 0.2 | 0.2 | 12.5 |
| Streptococcus pneumoniae SV-1 | 0.1 | 0.025 | 0.8 | 0.2 | 0.8 | 12.5 |
| Streptococcus pyogenes C-203 | 0.05 | 0.006 | 0.2 | ≦0.1 | 0.4 | 50 |

| Organisms | Compound Ex. 25 | Compound Ex. 26 | Compound Ex. 26a | Compound Ex. 27 | Compound Ex. 28 | Compound Ex. 29 |
|---|---|---|---|---|---|---|
| Enterobacter cloacae MA 2646 | 0.2 | 0.1 | 6.3 | 0.2 | 1.6 | 0.4 |
| Escherichia coli Vogel | 0.2 | 0.006 | 3.1 | 0.025 | 0.4 | 0.2 |
| Klebsiella pneumoniae MGH-2 | 0.8 | 0.1 | 6.3 | 0.1 | 0.4 | 0.2 |
| Proteus rettgeri M 1771 | 3.1 | 0.8 | 25 | 0.4 | 6.3 | 1.6 |
| Pseudomonas aeruginosa UI-18 | 3.1 | 0.8 | 12.5 | 0.8 | 3.1 | 3.1 |
| Staphylococcus aureus H 228 | 0.8 | 0.1 | 3.1 | 0.1 | 0.4 | 0.2 |
| Staphylococcus aureus UC-76 | ≦0.1 | 0.006 | 0.4 | 0.006 | 0.2 | 0.1 |
| Streptococcus faecalis MGH-2 | 0.4 | 0.1 | 3.1 | 0.1 | 0.8 | 0.2 |
| Streptococcus pneumoniae SV-1 | 0.4 | 0.4 | 6.3 | 0.2 | 1.6 | 0.8 |
| Streptococcus pyogenes C-203 | 0.4 | 0.2 | 3.1 | 0.1 | 1.6 | 0.4 |

| Organisms | Compound Ex. 30 | Compound Ex. 31 | Compound Ex. 32 | Compound Ex. 33 | Compound Ex. 34 | Compound Ex. 35 |
|---|---|---|---|---|---|---|
| Enterobacter cloacae MA 2646 | 0.1 | 0.4 | 1.6 | 6.3 | 1.6 | 0.1 |
| Escherichia coli Vogel | 0.05 | 0.2 | 0.2 | 1.6 | 0.8 | 0.013 |
| Klebsiella pneumoniae MGH-2 | 0.05 | 0.4 | 0.4 | 3.1 | 0.8 | 0.1 |
| Proteus rettgeri M 1771 | 0.2 | 0.4 | 1.6 | 12.5 | 3.1 | 0.2 |
| Pseudomonas aeruginosa UI-18 | 1.6 | 6.3 | 12.5 | 100 | 25 | 0.8 |
| Staphylococcus aureus H 228 | 0.1 | 0.4 | 0.05 | 0.8 | 1.6 | 0.1 |
| Staphylococcus aureus UC-76 | 0.013 | 0.1 | 0.025 | 0.2 | 0.2 | 0.025 |
| Streptococcus faecalis MGH-2 | 0.2 | 0.8 | 0.4 | 0.8 | 1.6 | 0.2 |
| Streptococcus pneumoniae SV-1 | 0.4 | 0.8 | 0.4 | 0.4 | 3.1 | 1.6 |
| Streptococcus pyogenes C-203 | 3.1 | 1.6 | 0.8 | 0.4 | 6.3 | 3.1 |

| Organisms | Compound Ex. 35a | Compound Ex. 35b | Compound Ex. 35c | Compound Ex. 35d | Compound Ex. 35e | Compound Ex. 35f |
|---|---|---|---|---|---|---|
| Enterobacter cloacae MA 2646 | 0.2 | 0.1 | 0.8 | 0.2 | 0.2 | 0.8 |
| Escherichia coli Vogel | 0.013 | 0.05 | 0.4 | 0.05 | 0.2 | 0.4 |
| Klebsiella pneumoniae MGH-2 | 0.1 | 0.1 | 0.4 | 0.1 | 0.8 | 0.8 |
| Proteus rettgeri M 1771 | 0.8 | 0.4 | 0.4 | 0.2 | 0.8 | 1.6 |
| Pseudomonas aeruginosa UI-18 | 3.1 | 6.3 | 6.3 | 3.1 | 6.3 | 6.3 |
| Staphylococcus aureus H 228 | 0.2 | 0.1 | 0.8 | 0.2 | 0.4 | 0.4 |
| Staphylococcus aureus UC-76 | 0.05 | 0.05 | ≦0.1 | 0.025 | ≦0.05 | ≦0.1 |
| Streptococcus faecalis MGH-2 | 0.8 | 0.4 | 0.4 | 0.2 | 0.4 | 1.6 |
| Streptococcus pneumoniae SV-1 | 3.1 | 1.6 | 6.3 | 3.1 | 1.6 | 6.3 |
| Streptococcus pyogenes C-203 | 3.1 | 1.6 | 3.1 | 1.6 | 3.1 | 1.6 |

| Organisms | Compound Ex. 36 | Compound Ex. 37 | Compound Ex. 37a | Compound Ex. 38 | Compound Ex. 38a | Compound Ex. 39 |
|---|---|---|---|---|---|---|
| Enterobacter cloacae MA 2646 | 0.1 | 0.8 | 0.8 | 3.1 | 3.1 | 0.8 |
| Escherichia coli Vogel | 0.025 | 0.2 | ≦0.1 | 0.8 | ≦0.1 | 0.2 |
| Klebsiella pneumoniae MGH-2 | 0.2 | 0.8 | 0.4 | 3.1 | 0.4 | 0.8 |
| Proteus rettgeri M 1771 | 0.2 | 6.3 | 1.6 | 3.1 | 6.3 | 1.6 |
| Pseudomonas aeruginosa UI-18 | 3.1 | 50 | 6.3 | 12.5 | 25 | 1.6 |
| Staphylococcus aureus H 228 | 0.4 | 0.4 | 0.8 | ≦0.05 | ≦0.1 | 1.6 |
| Staphylococcus aureus UC-76 | 0.1 | 0.2 | ≦0.1 | ≦0.05 | ≦0.1 | 0.05 |
| Streptococcus faecalis MGH-2 | 0.4 | 3.1 | 1.6 | 0.2 | ≦0.1 | 0.8 |
| Streptococcus pneumoniae SV-1 | 3.1 | 6.3 | 6.3 | 0.8 | 0.8 | 0.2 |
| Streptococcus pyogenes C-203 | 3.1 | 6.3 | 6.3 | 1.6 | 1.6 | 0.2 |

| Organisms | Compound Ex. 40 | Compound Ex. 41 | Compound Ex. 42 | Compound Ex. 42a | Compound Ex. 42b | Compound Ex. 42c |
|---|---|---|---|---|---|---|
| Enterobacter cloacae MA 2646 | 0.8 | 0.8 | 0.2 | 0.4 | 0.4 | 0.8 |
| Escherichia coli Vogel | 0.2 | 0.4 | 0.2 | ≦0.1 | 0.05 | 0.2 |
| Klebsiella pneumoniae MGH-2 | 0.8 | 1.6 | 0.4 | 0.2 | 0.2 | 0.4 |
| Proteus rettgeri M 1771 | 0.8 | 1.6 | 0.4 | 0.2 | 0.1 | 0.8 |

IN VITRO ANTIBACTERIAL ACTIVITY
Minimal Inhibitory Concentration
MIC (μg/ml)

-continued

| | | | | | | |
|---|---|---|---|---|---|---|
| Pseudomonas aeruginosa UI-18 | 6.3 | 12.5 | 1.6 | 3.1 | 0.8 | 1.6 |
| Staphylococcus aureus H 228 | 0.8 | 0.8 | 0.4 | 0.8 | 6.3 | 50 |
| Staphylococcus aureus UC-76 | 0.025 | 0.2 | 0.025 | ≦0.1 | 0.4 | 1.6 |
| Streptococcus faecalis MGH-2 | 0.8 | 1.6 | 0.2 | 0.8 | 1.6 | 12.5 |
| Streptococcus pneumoniae SV-1 | 0.8 | 0.8 | 3.1 | 12.5 | 1.6 | 25 |
| Streptococcus pyogenes C-203 | 0.4 | 1.6 | 0.2 | 12.5 | 0.8 | 25 |

| Organisms | Compound Ex. 43 | Compound Ex. 44 | Compound Ex. 45 | Compound Ex. 46 | Compound Ex. 47 | Compound Ex. |
|---|---|---|---|---|---|---|
| Enterobacter cloacae MA 2646 | ≦0.1 | ≦0.1 | ≦0.1 | ≦0.1 | ≦0.1 | |
| Escherichia coli Vogel | ≦0.1 | ≦0.1 | ≦0.1 | ≦0.1 | ≦0.1 | |
| Klebsiella pneumoniae MGH-2 | 0.2 | ≦0.1 | ≦0.1 | ≦0.1 | ≦0.1 | |
| Proteus rettgeri M 1771 | 0.1 | ≦0.1 | ≦0.1 | 0.8 | 0.2 | |
| Pseudomonas aeruginosa UI-18 | 0.4 | 0.4 | 0.1 | 0.2 | ≦0.1 | |
| Staphylococcus aureus H 228 | ≦0.1 | ≦0.1 | ≦0.1 | ≦0.1 | ≦0.1 | |
| Staphylococcus aureus UC-76 | ≦0.1 | ≦0.1 | ≦0.1 | ≦0.1 | ≦0.1 | |
| Streptococcus faecalis MGH-2 | ≦0.1 | ≦0.1 | ≦0.1 | ≦0.1 | 0.2 | |
| Streptococcus pneumoniae SV-1 | ≦0.1 | ≦0.1 | ≦0.1 | ≦0.1 | ≦0.1 | |
| Streptococcus pyogenes C-203 | ≦0.1 | ≦0.1 | ≦0.1 | ≦0.1 | 0.2 | |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about three carbon atoms except when specifically stated to be greater than three carbon atoms. Representative of such groups are methyl, ethyl, propyl, isopropyl, and the like.

The cycloalkyl groups contemplated by the invention comprise those having three to six carbons atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, γ-iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention can be prepared and administered in a wide variety of oral, parenteral and topical dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersable granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophlic carrier or base or ointment.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

7-[3-(Aminomethyl)-1-pyrrolidinyl]-1-ethyl-6-fluoro-1, 4-dihydro-4-oxo-1,8-naphthyridine-3-carboxylic acid A mixture of 2.00 g (7.39 mmole) of 7-chloro-1-ethyl-6-fluoro-1,4-dihydro-4-oxo-1,8-napthyridine-3-carboxylic acid, 250 ml acetonitrile and 2.22 g (22.17 mmole) 3-pyrrolidinemethanamine [J. Org. Chem., 26, 4955 (1961)], was stirred at room temperature for four days. The reaction was filtered and the precipitate dissolved in 500 ml ammonium hydroxide at pH 10.5. This solution was filtered and the solvent removed at reduced pressure. The product was washed 2×10 ml of water, then with ethanol/ether (1:1) until dry to give 1.65 g of 7-[3-(aminomethyl)-1-pyrrolidinyl]-1-ethyl-6-fluoro-1,4-dihydro-4-oxo-1,6-naphthyridine-3-carboxylic acid, mp 217°–218.5° C.

Analysis calculated for $C_{16}H_{19}FN_4O_3 \cdot \frac{1}{2}H_2O$: C, 55.97; H, 5.87; N, 16.32. Found: C, 55.89; H, 5.66; N, 16.33.

EXAMPLE 2

1-Ethyl-6-fluoro-1,4-dihydro-7-[3-[(methylamino)methyl]-1-pyrrolidinyl]-4-oxo-1,8-naphthyridine-3-carboxylic acid 1.00 g (3.69 mmole) 7-chloro-1-ethyl-6-fluoro-1,4-dihydro-4-oxo-1,8-napthyridine-3-carboxylic acid, 40 ml acetonitrile, and 1.27 g (11.08 mmole) N-methyl-3-pyrrolidinemethanamine are stirred at room temperature for three days. The reaction was filtered and the precipitate dissolved in aqueous ammonium hydroxide at pH 11. The solution was filtered and the solvent removed at reduced pressure. The product was washed with 5 ml of water, 10 ml ethanol/ether (1:1), and finally with ether until dry to give 0.571 g of 1-ethyl-6-fluoro-1,4-dihydro-7-[3-[(methylamino)methyl]-1-pyrrolidinyl]-4-oxo-1,8-naphthyridine-3-carboxylic acid, mp 251°–253° C.

Analysis calculated for $C_{17}H_{21}FN_4O_3 \cdot \frac{1}{2}H_2O$: C, 57.13; H, 6.20; N, 15.68. Found: C, 57.19; H, 6.03; N, 15.85.

EXAMPLE 3

1-Ethyl-7-[3-[(ethylamino)methyl]-1-pyrrolidinyl]6-fluoro-1,4-dihydro-4-oxo-1,8-napthyridine-3-carboxylic acid 1.00 g (3.69 mmole) of 7-chloro-1-ethyl-6-fluoro-1,4-dihydro-4-oxo-1,8-naphthyridine-3-carboxylic acid, 100 ml acetonitrile and 1.42 g (11.08 mmole) of N-ethyl-3-pyrrolidinemethanamine were stirred for three days at room temperature. The reaction mixture was then filtered, and the precipitate washed with water, ethanol/ether (1:3), and finally with ether until dry to give 0.715 g of 1-ethyl-7-[3-[(ethylamino)methyl]-1-pyrrolidinyl]-6-fluoro-1,4-dihydro-4-oxo-1,8-napthyridine-3-carboxylic acid, mp 229.5°–231.5° C.

The analysis was calculated for $C_{18}H_{23}FN_4O_3.0.24$-$H_2O$: C, 58.94; H, 6.45; N, 15.27; $H_2O$, 1.20. Found: C, 58.28; H, 6.85; N, 14.90; $H_2O$, 0.80.

EXAMPLE 4

1-Ethyl-6-fluoro-1,4-dihydro-4-oxo-7-[3-[(propylamino)methyl]-1-pyrrolidinyl]-1,8-propy-naphthyridine-3-carboxylic acid A near solution of 0.82 g (3.0 mmole) of 7-chloro-1-ethyl-6-fluoro-1,4-dihydro-4-oxo-1,8-naphthyridine-3-carboxylic acid and 1.4 g (10 mmole) of N-propyl-3-pyrrolidinemethanamine in 50 ml of acetonitrile was heated at reflux for four hours. The solvent was removed in vacuo, the residue dissolved in water, filtered through a fiber glass pad to clarify and the filtrate adjusted to pH 1.8 with 6M hydrochloric acid. The resulting clear solution was lyophilized and the residue recrystallized from ethanol to give 400 mg 1-ethyl-6-fluoro-1,4-dihydro-4-oxo-7-[3-[(propylamino)methyl]-1-pyrrolidinyl]-1,8-propy-naphthyridine-3-carboxylic acid, mp 281°–283° C. as the hydrochloride.

EXAMPLE 5

1-Ethyl-6-fluoro-1,4-dihydro-7-[3-[[(1-methylethyl)amino]methyl]-1-pyrrolidinyl]-4-oxo-1,8-naphthyridine-3-carboxylic acid A near solution of 0.82 g (3.0 mmole) of 7-chloro-1-ethyl-6-fluoro-1,4-dihydro-4-oxo-1,8-naphthyridine-3-carboxylic acid and 1.4 g (10 mmole) of N-(2-propyl)-3-pyrrolidinemethanamine in 50 ml of acetonitrile was heated at reflux for one hour. The solvent was removed in vacuo, the residue dissolved in water, filtered through a fiber glass pad to clarify and the filtrate adjusted to pH 2.0 with 6M hydrochloric acid. The resulting clear solution was lyophilized and the residue recrystallized from ethanol to give 200 mg of 1-ethyl-6-fluoro-1,4-dihydro-7-[3-[[(1-methylethyl)amino]methyl]-1-pyrrolidinyl]-4-oxo-1,8-naphthyridine-3-carboxylic acid, mp 302°–304° C. as the hydrochloride.

EXAMPLE 6

7-[3-[(Cyclopropylamino)methyl]-1-pyrrolidinyl]-1-ethyl-6-fluoro-1,4-dihydro-4-oxo-1,8-naphthyridine-3-carboxylic acid A near solution of 0.82 g (3.0 mmole) of 7-chloro-1-ethyl-6-fluoro-1,4-dihydro-4-oxo-1,8-naphthyridine-3-carboxylic acid and 1.4 g (10 mmole) of cyclopropyl-3-pyrrolidinemethanamine in 50 ml of acetonitrile was heated at reflux for two hours. The solvent was removed in vacuo, the residue dissolved in water, filtered through a fiber glass pad to clarify and the filtrate adjusted to pH 2.0 with 6M hydrochloric acid. The resulting clear solution was lyophilized and the residue recrystallized from ethanol to give 600 mg of 7-[3-[(cyclopropylamino)methyl]-1-pyrrolidinyl]-1-ethyl-6-fluoro-1,4-dihydro-4-oxo-1,8-naphthyridine-3-carboxylic acid, mp 271°–274° C. as the hydrochloride.

EXAMPLE 7

7-[3-(Aminomethyl)-1-pyrrolidinyl]-1-ethyl-6-fluoro-1,4-dihydro-4-oxo-3-quinolinecarboxylic acid A mixture of 1.00 g (3.95 mmole) of 6,7-difluoro-1-ethyl-1,4-dihydro-4-oxo-3-quinolinecarboxylic acid, 40 ml acetonitrile and 1.28 g (12.75 mmole) of 3-pyrrolidinemethanamine were stirred at room temperature overnight. The reaction was filtered, the precipitate washed with 10 ml of water, ethanol/ether (1:1) and finally with ether until dry to give 1.13 g of 7-[3-(aminomethyl)-1-pyrrodinyl]-1-ethyl-6-fluoro-1,4-dihydro-4-oxo-3-quinolinecarboxylic acid, mp 234°–236° C.

Analysis was calculated for $C_{17}H_{20}FN_3O_3..3H_2O$: C, 60.27; H, 6.13, N, 12.40. Found: C, 60.63; H, 5.85; N, 12.01.

EXAMPLE 8

1-Ethyl-6-fluoro-1,4-dihydro-7-[3-[(methylamino)methyl]-1-pyrrolidinyl]-4-oxo-3-quinolinecarboxylic acid A mixture of 1.00 g (3.95 mmole) 1-ethyl-6,7-difluoro-1,4-dihydro-4-oxo-3-quinolinecarboxylic acid, 10 ml N,N-dimethylformamide, 75 ml acetonitrile, and 1.35 g (11.85 mmole) of N-methyl-3-pyrrolidinemethanamine were refluxed overnight. The reaction was cooled to room temperature and filtered The precipitate was washed with water, ethanol/ether (1:3), and finally with ether until dry to give 1.17 g of 1-ethyl-6-fluoro-1,4-dihydro-7-[3-[(methylamino)methyl]-1-pyrrolidinyl]-4-oxo-3-quinolinecarboxylic acid, mp 247°–250° C.

Analysis for $C_{18}H_{22}FN_3O_3.\frac{1}{2}H_2O$: C, 60.66; H; 6.50; N, 11.79. Found: C, 60.69, H; 6.30; N, 11.82.

EXAMPLE 9

1-Ethyl-7-[3-[(ethylamino)methyl]-1-pyrrolidinyl]-6-fluoro-1,4-dihydro-4-oxo-3-quinolinecarboxylic acid A mixture of 2.70 g (10.0 mmole) of 7-chloro-1-ethyl-6-fluoro-1,4-dihydro-4-oxo-3-quinolinecarboxylic acid, 60 ml of β-picoline and 3.85 g (30.0 mmole) of N-ethyl-3-pyrrolidinemethanamine were refluxed overnight. Reaction mixture was cooled to room temperature, 100 ml concentrated ammonium hydroxide added, and the solvents removed at reduced pressure. A solution of 200 ml dichloromethane/ether (1:3) was added. The resulting precipitate was filtered, washed with ethanol/ether (1:3) and finally with ether until dry to give 1.87 g of 1-ethyl-7-[3-[(ethylamino)methyl]-1-pyrrolidinyl]-6-fluoro-1,4-dihydro-4-oxo-3-quinolinecarboxylic acid, mp 248°–252° C.

Analysis calculated for $C_{19}H_{24}FN_3O_3.1.48H_2O$: C, 58.81; H, 7.00; N, 10.83. Found: C, 58.70; H, 6.53; N, 10.85.

EXAMPLE 10

7-[3-(Aminomethyl)-1-pyrrolidinyl]-1-ethyl-6,8-difluoro-1,4-dihydro-4-oxo-3-quinolinecarboxylic acid A mixture of 0.50 g (1.84 mmole) of 1-ethyl-6,7,8-trifluoro-1,4-dihydro-4-oxo-3-quinolinecarboxylic acid, 5 ml of acetonitrile, 0.28 g (1.84 mmole) of 1,8-diazabicyclo[5.4.0]undec-7-ene and 0.19 g (1.94 mmole) of 3-pyrrolidinemethanamine was refluxed for one hour; then stirred at room temperature overnight. The reaction was filtered and the precipitate washed with ethyl ether to give 0.56 g of 7-[3-(aminomethyl)-1-pyrrolidinyl]-1-ethyl-6,8-difluoro-1,4-dihydro-4-oxo-3-quinolinecarboxylic acid, mp 219°–221° C.

The following compounds were also prepared by the above procedure:
7-[3-(aminomethyl)-1-pyrrolidinyl]-6,8-difluoro-1-(2-fluoroethyl)-1,4-dihydro-4-oxo-3-quinolinecarboxylic acid, mp 224°–226° C. (10a) and 7-[3-(aminomethyl)-1- pyrrolidinyl]-6,8-difluoro-1-ethenyl-1,4-dihydro-4-oxo-3-quinolinecarboxylic acid, mp 204°–208° C. (10b).

EXAMPLE 11

1-Ethyl-7-[3-[(ethylamino)methyl]-1-pyrrolidinyl]-6,8-difluoro-1,4-dihydro-4-oxo-3-quinolinecarboxylic acid A mixture of 22.50 g (83.03 mmole) 1-ethyl-1,4-dihydro-4-oxo-6,7,8-trifluoro-3-quinolinecarboxylic acid, 225 ml acetonitrile, 11.25 g (87.08 mmole) N-ethyl-3-pyrrolidinemethanamine and 12.6 g (83.03 mmole) 1,8-diazabicyclo[5.4.0]undec-7-ene was refluxed 1 hour then was stirred at room temperature overnight. The solid was filtered and washed with ether to give 26.33 g of 1-ethyl-7-[3-[(ethylamino)methyl]-1-pyrrolidinyl]-6,8-difluoro-1,4-dihydro-4-oxo-3-quinolinecarboxylic acid, mp 208°–210° C.

Analysis calculated for $C_{19}H_{23}F_2N_3O_3$: C, 60.15; H, 6.11; N, 11.08. Found: C, 59.85; H, 6.17; N, 11.08.

The following compounds were also prepared by the above procedure: 7-[3-[(ethylamino)methyl]-1-pyrrolidinyl]-6,8-difluoro-1-(2-fluoroethyl)-1,4-dihydro-4-oxo-3-quinolinecarboxylic acid, mp 221°–223° C. (11a), 7-[3-[(ethylamino)methyl]-1-pyrrolidinyl-6,8-difluoro-1-ethenyl-1,4-dihydro-4-oxo-3-quinolinecarboxylic acid, mp 217°–220° C. (11b), and 1-methyl-7-[3-[(ethylamino)methyl]-1-pyrrolidinyl]-6,8-difluoro-1,4-dihydro-4-oxo-3-quinolinecarboxylic acid, mp 238°–240° C. (11c).

EXAMPLE 12

1-Ethyl-6,8-difluoro-1,4-dihydro-7-[3-[[(2-hydroxyethyl)amino]methyl]-1-pyrrolidinyl]-4-oxo-3-quinolinecarboxylic acid A mixture of 0.50 g (1.84 mmole) of 1-ethyl-6,7,8-trifluoro-4-oxo-quinoline-3-carboxylic acid, 5 ml acetonitrile, 0.28 g (1.84 mmole) 1,8-diazabicyclo[5.4.0]undec-7-ene and 0.28 g (1.94 mmole) of 2-[(3-pyrrolidinylmethyl)amino]ethanol was refluxed one hour and then stirred at room temperature overnight. The reaction was filtered and the precipitate washed with ether until dry to give 0.58 g of 1-ethyl-6,8-difluoro-1,4-dihydro-7-[3-[[(2-hydroxyethyl)amino]methyl]-1-pyrrolidinyl]-4-oxo-3-quinolinecarboxylic acid, mp 215°–216° C.

Using N-(2,2,2-trifluoroethyl)-3-pyrrolidinemethanamine in the above procedure gave 1-ethyl-6,8-difluoro-1,4-dihydro-4-oxo-7-[3-[[(2,2,2-trifluoroethyl)amino]methyl]-1-pyrrolidinyl]-3-quinolinecarboxylic acid, mp 182°–183° C. (12a).

Using three equivalents of N-(2-propyl)-3-pyrrolidinemethanamine and no 1,8-diazabicyclo[5.4.0]undec-7-ene in the above procedure gave 1-ethyl-7-[3-[[(1-methylethyl)amino]methyl]-1-pyrrolidinyl]-6,8-difluoro-1,4-dihydro-4-oxo-3-quinolinecarboxylic acid, mp 198°–200° C. (12b).

EXAMPLE 13

7-[4-(Aminomethyl)-1-piperidinyl]-1-ethyl-6-fluoro-1,4-dihydro-4-oxo-1,8-naphthyridine-3-carboxylic acid A mixture of 0.52 g (0.19 mmole) of 7-chloro-1-ethyl-6-fluoro-1,4-dihydro-4-oxo-1,8-naphthyridine-3-carboxylic acid, 150 ml acetonitrile, and 0.66 g (5.76 mmole) 4-aminomethylpiperidine [J. Med. Chem., 9 441 (1966)] were stirred at room temperature for four days. The reaction was filtered and the precipitate dissolved in 500 ml of aqueous ammonium hydroxide at pH 10.5. The solution was filtered and the solvent was removed at reduced pressure. The precipitate was washed with 5 ml of water, then ether until dry to give 0.42 g of 7-[4-(aminomethy)-1-piperidinyl]-1-ethyl-6-fluoro-1,4-dihydro-4-oxo-1,8-naphthyridine-3-carboxylic acid, mp 203°–206° C.

Analysis for $C_{17}H_{21}FN_4O_3.H_2O$: C, 55.73; H, 6.33; N, 15.29. Found: C, 55.30; H, 6.03; N, 15.30.

EXAMPLE 14

7-[3-(Aminomethyl)-1-piperidinyl]-1-ethyl-6-fluoro-1,4-dihydro-4-oxo-1,8-naphthyridine-3-carboxylic acid A mixture of 1.04 g (3.84 mmole) of 7-chloro-1-ethyl-6-fluoro-1,4-dihydro-4-oxo-1,8-naphthyridine-3-carboxylic acid, 100 ml of acetonitrile and 1.32 g (11.5 mmole) of 3-aminomethylpiperidine [J. Org. Chem., 44, 4536 (1979)] were stirred at room temperature for four days. The reaction was filtered and the precipitate dissolved in aqueous ammonia, pH 10.5. The solution was filtered and the solvent removed at reduced pressure. The product was washed with water, then ether until dry to give 1.23 g of 7-[3-(aminomethyl)-1-piperidinyl]-1-ethyl-6-fluoro-1,4-dihydro-4-oxo-1,8-naphthyridine-3-carboxylic acid, mp 120°–122° C.

Analysis for $C_{17}H_{21}FN_4O_3.3H_2O$: C, 57.72; H, 6.15; N, 16.08. Found: C, 57.72; H, 6.00; N, 15.80.

EXAMPLE 15

7-(3-Amino-1-pyrrolidinyl)-1-ethyl-6,8-difluoro-1,4-dihydro-4-oxo-3-quinolinecarboxylic acid A suspension of 0.81 g (3.0 mmole) of 1-ethyl-1,4-dihydro-6,7,8-trifluoro-4-oxo-3-quinolinecarboxylic acid, 1.28 g (10 mmole) of 3-acetylamminopyrrolidine [U.S. Pat. No. 4,341,784] and 1.5 g (15 mmole) of triethylamine in 50 ml of acetonitrile was refluxed for four hours. The solvent was removed in vacuo and the residue was dissolved in 50 ml of 6.0 M hydrochloric acid-/ethanol (1:1). The mixture was refluxed for four hours and the ethanol was removed in vacuo. The residue was diluted to 100 ml with water and adjusted to pH 7.3 with 1.0 N sodium hydroxide. After cooling to 5° C., the precipitate was removed by filtration, washed successively with water, ethanol, ether, and dried in vacuo to give 0.6 g of 7-(3-amino-1-pyrrolidinyl)-1-ethyl-6,8-difluoro-1,4-dihydro-4-oxo-3-quinolinecarboxylic acid, mp 240°–242° C.

EXAMPLE 16

7-(3-Amino-1-azetidinyl)-1-ethyl-6-fluoro-1,4-dihydro-4-oxo-1,8-naphthyridine-3-carboxylic acid A suspension of 0.81 g (3.0 mmole) of 7-chloro-1-ethyl-6-fluoro-1,4-dihydro-4-oxo-1,8-naphthyridine-3-carboxylic acid, 1.0 g (6.0 mmole) of 1,1-dimethylethyl-(3-azetidinyl)carbamate, 1.0 g (10 mmole) triethylamine and 50 ml of acetonitrile was heated at reflux 35 for four hours. The solvent was removed in vacuo and the residue was dissolved in 10 ml of trifluoroacetic acid. The solution was stirred at room temperature for one hour, the solvent was removed in vacuo and the residue dissolved in water. The turbid solution was clarified by filtration and the filtrate adjusted to pH 7.3 with 1.0 N sodium hydroxide. The resulting precipitate was removed by filtration, washed successively with water, ethanol and ether. Drying in vacuo gave 0.2 g of 7-(3-amino-1-azetidinyl)-1-ethyl-6-fluoro-1,4-dihydro-4-oxo-1,8-naphthyridine-3-carboxylic acid, mp 260°–262° C.

Using 1,1-dimethyl(3-azetidinylmethyl)carbamate in the above procedure gave 7-[(3-aminomethyl)-1-

EXAMPLE 17

1-Ethyl-6-fluoro-1,4-dihydro-7-[3-[(methylamino)methyl]-4-oxo-1,8-naphthyridine-3-carboxylic acid A suspension of 0.81 g (3.0 mmole) of 7-chloro-1-ethyl-6-fluoro-1,4-dihydro-4-oxo-1,8-naphthyridine-3-carboxylic acid, 0.9 g (9.0 mmole) of N-methyl-3-azetidinemethanamine and 30 ml of acetonitrile was refluxed for six hours. The reaction was cooled to 5° C. The filtered solids were washed with acetonitrile, ether, and dried in vacuo. The dried solid was suspended in 70 ml of water and made basic to pH 11.0 after filtering through a fiber glass pad to clarify, the filtrate was acidified to pH 7.4 with 1.0 M hydrochloric acid. The resulting precipitate was removed by filtration, washed successively with water, 2-propanol, ether and dried in vacuo to give 270 mg of 1-ethyl-6-fluoro-1,4-dihydro-7-[3-[(methylamino)-methyl]-4-oxo-1,8-naphthyridine-3-carboxylic acid, mp 180°–182° C.

Using N-ethyl-3-azetidinemethanamine in the above procedure gave 1-ethyl-7[(3-ethylaminomethyl)-1-azetindyl]-6-fluoro-1,4-dihydro-4-oxo-1,8-naphthyridine-3-carboxylic acid, mp 208°–210° C. (17a).

In similar fashion reaction of N-ethyl-3-azetidinemethanamine with 1-ethyl-1,4-dihydro-4-oxo-6,7,8-trifluoro-3-quinoline carboxylic acid using the above procedure gave 1-ethyl-7[(3-ethylaminomethyl)-1-azetidinyl]-6,8-difluoro-1,4-dihydro-4-oxo-3-quinolinecarboxylic acid, mp 208°–210° C. (17b).

EXAMPLE 18

10-[3-(Aminomethyl)-1-pyrrolidinyl]-9-fluoro-2,3-dihydro-3-methyl-7-oxo-7H-pyrido[1,2,3-de]-1,4-benzoxazine-6-carboxylic acid 0.75 g (0.27 mmole) of 9,10-difluoro-2,3-dihydro-3-methyl-7-oxo-7H-pyrido[1,2,3-de]-1,4-benzoxazine-6-carboxylic acid, 40 ml acetonitrile, and 0.80 g (8.0 mmole) of. 3-pyrrolidinemethanamine were refluxed overnight. The solvent was removed at reduced pressure and the residue titurated with 40 ml of ethanol/ether (1:1), to give 0.90 g of 10-[3-(aminomethyl)-1-pyrrolidinyl]-9-fluoro-2,3-dihydro-3-methyl-7-oxo-7H-pyrido[1,2,3-de]-1,4-benzoxazine-6-carboxylic acid, mp 213°–216° C.

EXAMPLE 19

9-Fluoro-2,3-dihydro-3-methyl-10-[3-[(methylamino)-methyl]-1-pyrrolidinyl]-7-oxo-7H-pyrido[1,2,3-de]-1,4-benzoxazine-6-carboxylic acid 0.75 g (2.7 mmole) of 9,10-difluoro-2,3-dihydro-3-methyl-7-oxo-7H-pyrido[1,2,3-de]-1,4-benzoxazine-6-carboxylic acid, 40 ml acetonitrile, and 0.91 g (0.80 mmole) of N-methyl-3-pyrrolidinemethanamine were refluxed overnight. The solvent was removed at reduced pressure and the residue tititrated with 40 ml of methanol. The precipitate was filtered, washed repeatedly with 95% ethanol and finally with ether until dry to give 0.68 g of 9-fluoro-2,3-dihydro-3-methyl-10-[3-[(methylamino)methyl]-1-pyrrolidinyl]-7-oxo-7H-pyrido[1,2,3-de]-1,4-benzoxazine-6-carboxylic acid, mp 235°–237.5° C.

Analysis for $C_{19}H_{22}FN_3O_4 \cdot \frac{1}{2}H_2O$: C, 59.37; H, 6.03; N, 10.93. Found: C, 59.34, H, 5.78; N, 10.95.

EXAMPLE 20

10-[2-[(Ethylamino)methyl]-1-pyrrolidinyl]-9-fluoro-2,3-dihydro-3-methyl-7-oxo-7H-pyrido[1,2,3-de]-1,4-benzoxazine-6-carboxylic acid 0.75 g (2.7 mmole) of 9,10-difluoro-2,3-dihydro-3-methyl-7-oxo-7H-pyrido[1,2,3-de]-1,4-benzoxazine-6-carboxylic acid, 40 ml acetonitrile and 1.03 g (8.00 mmole) of N-ethyl-3-pyrrolidinemethanamine were refluxed overnight. The reaction mixture was cooled in an ice bath and then filtered. The precipitate was washed with ethanol/ether (4:1), and then with ether until dry to give 0.86 g of 10-[3-[(ethylamino)-methyl]-1-pyrrolidinyl]-9-fluoro-2,3-dihydro-3-ethyl-7-oxo-7H-pyrido[1,2,3-de]-1,4-benzoxazine-6-carboxylic acid, mp 221°–224° C.

Analysis for $C_{20}H_{21}FN_3O_4 \cdot \frac{1}{2}H_2O$: C, 60.29; H, 6.33, N, 10.55. Found: C, 60.45, H, 6.21, N, 10.80.

EXAMPLE 21

A general procedure for the compounds listed below is as follows: A mixture of 1 g of the appropriate halogenated quinoline or naphthyridine carboxylic acid, 10 ml of an appropriate solvent (acetonitrile or β-picoline), one equivalent of 1,8-diazabicyclo[5.4.0]unde-7-ene and 1.05 equivalents of the amine are refluxed for a given amount of time, then stirred at room temperature overnight. The product is filtered off and washed with ethyl ether until dry.

The requisite amines may also be prepared according to the methods described in J. Heterocyclic Chem., 20, 321, 439 (1983).

1-ethyl-6-fluoro-1,4-dihydro-7-(5-methyloctahydropyrrolo[3,4-c]pyrrol-2-yl)-4-oxo-1,8-naphthyridine-3-carboxylic acid, (21).

1-ethyl-6-fluoro-1,4-dihydro-7-(octahydropyrrolo[3,4c-]pyrrol-2-yl)-4-oxo-1,8-naphthyridine-3-carboxylic acid, (21a).

1-ethyl-6-fluoro-1,4-dihydro-7-(octahydro-1H-pyrrolo[3,4-c]pyridin-2-yl)-4-oxo-1,8-naphthyridine-3-carboxylic acid (21b).

1-ethyl-6-fluoro-1,4-dihydro-7-(5-methyloctahydropyrrolo-[3,4-c]pyrrol-2-yl)-4-oxo-3-quinolinecarboxylic acid, (21c).

1-ethyl-6-fluoro-1,4-dihydro-7-(octahydropyrrolo[3,4-c]-pyrrol-2-yl)-4-oxo-3-quinolinecarboxylic acid, (21d).

1-ethyl-6-fluoro-1,4-dihydro-7-(octahydro-1H-pyrrolo[3,4-c]pyridin-2-yl)-4-oxo-3-quinolinecarboxylic acid, (21e).

1-ethyl-6,8-difluoro-1,4-dihydro-7-(5-methyloctahydropyrrolo[3,4-c]pyrrol-2-yl)-4-oxo-3-quinolinecarboxylic acid, mp 213°–214° C. (21f).

1-ethyl-6,8-difluoro-1,4-dihydro-7-(octahydropyrrolo[3,4-c]pyrrol-2-yl)-4-oxo-3-quinolinecarboxylic acid, (21g).

1-ethyl-6,8-difluoro-1,4-dihydro-7-(octahydro-1H-pyrrolo[3,4-c]pyridin-2-yl)-4-oxo-3-quinolinecarboxylic acid (21h).

EXAMPLE 22

1-Ethyl-6-fluoro-1,4-dihydro-7-(2,7-diazaspiro[4.4]-non-2-yl)-4-oxo-1,8-naphthyridine-3-carboxylic acid Hydrochloride A suspension of of 1.10 g (4.00 mmol) 1-ethyl-6-fluoro-7-chloro-4-oxo-1,4-dihydro-1,8-naphthyridine-3-carboxylic acid in 40 ml acetonitrile was treated with 1.10 g (8.7 mmol) 2,7-diazaspiro[4.4]nonane and the mixture was stirred at room temperature 4.5 hours. A crude solid was filtered, stirred with 10 ml water, filtered, dissolved in 100 ml 6 M ammonium hydroxide and lyophilized to afford 0.53 g of solid. This was dissolved in dilute hydrochloric acid, filtered, lyophilized and crystallized from ethanol-water to give 0.26 g of the title compound, mp >300° C.

Analysis calcualted for $C_{18}H_{22}N_4ClFO_3$: C, 54,47; H, 5.59; N, 14.12; Cl, 8.94. Found: C, 54.14; H, 5.60, N, 13.85; Cl, 8.68.

EXAMPLE 23

1-Ethyl-6,8-difluoro-1,4-dihydro-7-(2,7-diazaspiro[4.4]-non-2-yl)-4-oxo-3-quinolinecarboxylic acid A suspension of 0.81 g (3.0 mmol) 1-ethyl-6,7,8-trifluoro-4-oxo-1,4-dihydroquinoline-3-carboxylic acid in 40 ml acetonitrile was treated with 0.80 g (6.3 mmol) 2,7-diazaspiro[4.4]nonane [J. Org. Chem. 46, 2757 (1981)] and the mixture stirred two days at room temperature, refluxed 1.5 hours, cooled, and filtered to afford 1.17 g of the title compound, mp 234°–240° C. (dec).

Analysis calculated for $C_{19}H_{21}N_3F_2O_3$; C, 60.47; H, 5.61; N, 11.13. Found: C, 60.17; H, 5.46; N, 11.11.

EXAMPLE 24

1-Ethyl-6-fluoro-1,4-dihydro-7-(7-methyl-2,7-diazaspiro[4.4]non-2-yl)-4-oxo-1,8-naphthyridine-3-carboxylic acid A stirred suspension of 4.40 g (20.7 mmol) of 2-methyl-2,7-diazaspiro[4.4]nonane dihydrochloride in 200 ml acetonitrile was treated with 9.42 g (62 mmol) 1,8-diazabicyclo[5.4.0]undec-7-ene and 5.42 g (20 mmol) 1-ethyl-6-fluoro-7-chloro-4-oxo-1,4-dihydro-1,8-naphthyridine-3-carboxylic acid was added. After stirring 23 hours at room temperature the precipitated product was filtered, washed with acetonitrile and ether, and recrystallized from ethanol to afford 3.99 g of the title compound, mp 252°–254° C. (dec).

Using the above procedure with 2,8-diazaspiro[5.5]undecane dihydrochloride [Helv. Chim. Acta, 36, 1815 (1953)] gave 1-ethyl-6-fluoro-1,4-dihydro-7-(2,8-diazaspiro[5.5]undec-2-yl)-4-oxo-1,8-naphthyridine-3-carboxylic acid, mp 188°–192° C. (dec). (24a).

EXAMPLE 25

1-Ethyl-6-fluoro-1,4-dihydro-7-(7-methyl-2,7-diazaspiro[4.4]-non-2-yl)-4-oxo-3-quinolinecarboxylic acid A suspension of 0.65 g (3.05 mmol) 2-methyl-2,7-diaspiro[4.4]nonane dihydrochloride in 40 ml acetonitrile was treated with 1.33 g (9.0 mmol) 1,8-diazabicyclo[5.4.0]undec-7-ene and 0.76 g (3.0 mmol) 1-ethyl-6,7-difluoro-1,4-dihydro-4-oxo-3-quinolinecarboxylic acid was added. The mixture was refluxed overnight and the hot solution was filtered. After crystallizing at room temperature the product was filtered and washed with acetonitrile to afford 0.72 g of the title compound, mp 239°–241° C. (dec).

Analysis calculated for $C_{20}H_{24}N_3FO_3$; C, 64.33; H, 6.48; N, 11.25; Found: C, 64.25; H, 6.50; N, 11.27.

EXAMPLE 26

1-Ethyl-6,8-difluoro-1,4-dihydro-7-(7-methyl-2,7-diazaspiro[4.4]non-2-yl)-4-oxo-3-quinolinecarboxylic acid A suspension of 0.64 g (3.0 mmol) 2-methyl-2,7-diazaspiro[4.4]nonane dihydrochloride in 40 ml acetonitrile was treated with 1.33 g (9.0 mmol) 1,8-diazabicyclo[5.4.0]undec-7-ene and 0.81 g (3.0 mmol) 1-ethyl-6,7,8-trifluoro-1,4-dihydro-4-oxo-3-quinolinecarboxylic acid was added. The mixture was stirred 45 minutes at room temperature, refluxed 1.5 hours, and stirred at room temperature overnight. The precipitate was filtered and washed with acetonitrile and ether to afford 0.87 g of the title compound, mp 229°–231° C. (dec).

Analysis calculated for $C_{20}H_{23}N_3F_2O_3$: C, 61.37; H, 5.92; N, 10.74; Found: C, 61.20; H, 5.88; N, 10.75.

Using the above procedure with 2,8-diazaspiro[5.5]undecane dihydrochloride gave 1-ethyl-6,8-difluoro-1,4-dihydro-7-(2,8-diazaspiro[5.5]undec-2-yl)-4-oxo-3-quinolinecarboxylic acid, mp 267°–268° C. dec. (26a).

EXAMPLE 27

9-Fluoro-2,3-dihydro-3-methyl-10-(7-methyl-2,7-diazaspiro[4.4]non-2-yl)-7-oxo-7H-pyrido[1,2,3-de]1,4-benzoxazine-6-carboxylic acid A suspension of 0.42 g (1.97 mmol) 2-methyl-2,7-diazaspiro[4.4]nonane dihydrochloride in 25 ml acetonitrile was treated with 0.85 g (5.80 mmol) 1,8-diazabicyclo[5.4.0]undec-7-ene and 0.52 g (1.85 mmol) 9,10-difluoro-2,3-dihydro-3-methyl-7-oxo-7H-pyrido[1,2,3-de]1,4-benzoxazine-6-carboxylic acid was added. The mixture was stirred two hours at room temperature and then refluxed overnight. The product which crystallized on cooling was filtered, washed with acetonitrile and recrystallized from acetonitrile to afford 0.45 g of the title compound, mp 227°–230° C. (dec).

Analysis calculated for $C_{21}H_{22}N_3FO_4$: C, 63.15; H, 5.55; N, 10.52; Found: C, 63.13; H, 5.73; N, 10.51.

EXAMPLE 28

1-Ethyl-6-fluoro-1,4-dihydro-7-(7-ethyl-2,7-diazaspiro[4.4]non-2-yl)-4-oxo-1,8-naphthyridine-3-carboxylic acid The title compound was prepared according to example 24 by reacting 1-ethyl-6-fluoro-7-chloro-4-oxo-1,4-dihydro-1,8-naphthyridine-3-carboxylic acid with 2-ethyl-2,7diazaspiro[4.4]nonane dihydrochloride; mp 215°–217° C. (dec).

Analysis calculated for $C_{20}H_{25}N_4FO_3$: C, 61.84; H, 6.49; N, 14.42. Found: C, 61.68; H, 6.17; N, 14.20.

EXAMPLE 29

1-Ethyl-6,8-difluoro-1,4-dihydro-7-(7-ethyl-2,7-diazaspiro[4.4]non-2-yl)-4-oxo-3-quinolinecarboxylic acid The title compound was prepared according to example 26 by reacting 1-ethyl-6,7,8-trifluoro-4-oxo-1,4-dihydroquinoline-3-carboxylic acid with 2-ethyl-2,7-diazaspiro[4.4]nonane dihydrochloride, mp 199°–202° C. (dec).

Analysis calculated for $C_{21}H_{25}N_3F_2O_3$: C, 6.21; H, 6.22; N, 10.36. Found: C, 62.24; H, 6.15; N, 10.36.

EXAMPLE 30

7-[2-(Aminomethyl)-4-thiazolyl]-1-ethyl-6-fluoro-1,4-dihydro-4-oxo-3-quinolinecarboxylic acid A suspension of 0.59 g (1.54 mmol) ethyl 7-bromoacetyl-1-ethyl-6-fluoro-1,4-dihydro-4-oxo-3-quinolinecarboxylate in 4 ml N,N-dimethylformamide was treated with 0.22 g (1.67 mol) acetamidothioacetamide [prepared according to J. Am. Chem. Soc. 51, 1817 (1929)]. After stirring three hours the mixture was treated with 0.22 ml (1.58 mmol) triethylamine, stirred one hour more and poured into 40 ml ice water. The precipitate was filtered, washed with water and dried to afford 0.45 g crude solid. Chromatography on a column of 20 g silica gel with chloroform-methanol (9:1) and crystallization from ethanol gave 0.37 g ethyl 7-[2-(acetamidomethyl)-4-thiazolyl]-1-ethyl-6-fluoro-1,4-dihydro-4-oxo-3-quinolinecarboxylate, mp 230°–233° C. (dec).

A solution of 0.32 g (0.76 mmol) ethyl 7-[2-(acetamidomethyl)-4-thiazolyl]-1-ethyl-6-fluoro-1,4-dihydro-4-oxo-3-quinolinecarboxylate in 3 ml 6N hydrochloric acid was stirred at reflux three hours. The mixture was evaporated to dryness and the resulting solid was suspended in 5 ml water and dissolved by addition of 1N sodium hydroxide to pH 11. After filtration the product was precipitated by addition of 1N hydrochloric acid to pH 6.2, filtered, washed with water and dried to afford 0.22 g 7-[2-aminomethyl)-4-thiazolyl]-1-ethyl-6-fluoro-1,4-dihydro-4-oxo-3-quinolinecarboxylic acid, mp 249°–254° C. (dec).

EXAMPLE 31

7-[2-(Methylaminomethyl)-4-thiazolyl]-1-ethyl-6-fluoro-1,4-dihydro-4-oxo-3-quinolinecarboxylic acid According to example 30, reacting 7-bromoacetyl-1-ethyl-6-fluoro-1,4-dihydro-4-oxo-3-quinolinecarboxylic acid ethyl ester with 2-(N-acetyl-N-methylamino)thioacetamide in ethanol gave 1-ethyl-6-fluoro-7-[2-(N-acetyl-N-methylaminomethyl)-4-thiazolyl]-1,4-dihydro-4-oxo-3-quinolinecarboxylic acid ethyl ester, mp 173°–175° C. which was then hydrolyzed in refluxing 6N hydrochloric acid to give the title compound, mp 230°–234° C. (dec).

Analysis calculated for $C_{17}H_{16}N_3FO_3S$: C, 56.50; H, 4.46; N, 11.63. Found: C, 56.26; H, 4.56; N, 11.40.

EXAMPLE 32

7-[2-Ethylaminomethyl)-4-thiazolyl]-1-ethyl-6-fluoro-1,4-dihydro-4-oxo-3-quinolinecarboxylic acid hydrochloride According to example 30, reacting 7-bromoacetyl-1-ethyl-6-fluoro-1,4-dihydro-4-oxo-3-quinolinecarboxylic acid ethyl ester with 2-(N-acetyl-N-ethylamino)thioacetamide in ethanol gave 1-ethyl-7-[2-[(N-acetyl-N-ethylamino)methyl]-4-thiazolyl]-6-fluoro-1,4-dihydro-4-oxo-3-quinolinecarboxylic acid ethyl ester, mp 160°–161° C. which was then hydrolyzed in refluxing 6N hydrochloric acid to afford the title compound, mp 289°–300° C. (dec).

Analysis calculated for $C_{18}H_{19}N_3ClFO_3S.0.3H_2O$: C, 51.81; H, 4.73; N, 10.07; Cl, 8.50. Found: C, 51.81; H, 4.79; N, 10.09; CL, 8.49.

EXAMPLE 33

1-Ethyl-6-fluoro-1,4-dihydro-7-[2-[[(2-hydroxyethyl)amino]methyl]-4-thiazolyl]-4-oxo-3-quinolinecarboxylic acid hydrochloride According to example 30, by reacting 7-bromoacetyl-1-ethyl-6-fluoro-1,4-dihydro-4-oxo-3-quinolinecarboxylic acid ethyl ester with 2-[N-(2-acetoxyethyl)-N-acetylamino]thioacetamide in ethanol gave 1-ethyl-6-fluoro-1,4-dihydro-7-[2-[[N-(2-acetoxyethyl)-N-acetylamino]methyl]-4-thiazolyl]-4-oxo-3-quinolinecarboxylic acid ethyl ester, mp 148°–152° C., resolidified and melted 164°–165° C., which was hydrolyzed with refluxing 6 N hydrochloric acid to afford the titled compound, mp 290° C. (dec).

Analysis calculated for $C_{18}H_{17}N_3FClO_4S$: C, 50.76; H, 4.02; N, 9.87. Found: C, 50.36; H, 4.50; N, 9.66.

EXAMPLE 34

7-[2-(1-aminoethyl)-4-thiazolyl]-1-ethyl-6-fluoro-1,4-dihydro-4-oxo-3-quinolinecarboxylic acid According to example 30, reacting 7-bromoacetyl-1-ethyl-6-fluoro-1,4-dihydro-4-oxo-3-quinolinecarboxylic acid ethyl ester with 2-(acetylamino)thiopropionamide in ethanol gave 7-[2-[1-(N-acetylamino)ethyl]-4-thiazolyl]-1-ethyl-6-fluoro-1,4-dihydro-4-oxo-3-quinolinecarboxylic acid ethyl ester, mp 236°–238° C., which was hydrolyzed with refluxing 6N hydrochloric acid to afford the title compound, mp 246°–250° C. (dec).

Analysis calculated for $C_{17}H_{16}N_3FO_3S.0.2H_2O$: C, 55.94; H, 4.53; N, 11.51. Found: C, 55.92; H, 4.51; N, 11.68.

EXAMPLE 35

7-[2-(aminomethyl)-4-thiazolyl]-1-ethyl-6,8-difluoro-1,4-dihydro-4-oxo-3-quinolinecarboxylic acid To 800 mg (1.99 mmol) of the 7-bromoacetyl-1-ethyl-6,8-difluoro-1,4-dihydro-4-oxo-3-quinolinecarboxylic acid in a mixture of N,N-dimethylformamide and ethanol was added 446 mg (1.0 eq) of 2-(N-benzyloxycarbonyl) aminothioacetamide. The mixture was stirred for 72 hours at room temperature. The mixture was added to water and ice and the solids were filtered to give 0.92 g of the 1-ethyl-6,8-difluoro-1,4-dihydro-4-oxo-7-[2-[[(phenylmethoxy)carbonyl]aminomethyl]-4-thiazoyl]-3-quinolinecarboxylic acid, mp 185°–190° C. Without further purification, the solids were treated with hydrobromic acid in acetic acid overnight and poured into ether:ethyl acetate. Filtration gave a solid that was dissolved in aqueous ammonia at pH 10.8. Concentration of this mixture to one third volume and filtration gave 0.46 g of 7-[2-(aminomethyl)-4-thiazolyl]-1-ethyl-6,8-difluoro-1,4-dihydro-4-oxo-3-quinolinecarboxylic acid, mp 199°–203° C.

In similar fashion the following compounds were prepared:

1-Ethyl-6,8-difluoro-1,4-dihydro-7-[2-[(methylamino)methyl]-4-thiazolyl]-4-oxo-3-quinolinecarboxylic acid, mp 172°–174° C. (35a);

7-[2-[(ethylamino)methyl]-4-thiazolyl]-1-ethyl-6,8-difluoro-1,4-dihydro-4-oxo-3-quinolinecarboxylic acid, mp 155°–157° C. (35b);

7-[2-(aminomethyl)-4-thiazolyl]-6,8-difluoro-1-(2-fluoroethyl)-1,4-dihydro-4-oxo-3-quinolinecarboxylic acid, mp 216°–218° C. (35c);

6,8-difluoro-1-(2-fluoroethyl)-1,4-dihydro-7-[2[(methylamino)methyl]-4-thiazolyl]-4-oxo-3-quinolinecarboxylic acid, mp 214°–215° C. (35d);

7-[2-[(ethylamino)methyl]-4-thiazolyl]-6,8-difluoro-1-(2-fluoroethyl)-1,4-dihydro-4-oxo-3-quinolinecarboxylic acid, mp 197°–201° C. (35e), and 10-[2-(aminomethyl)-4-thiazolyl]-9-fluoro-2,3-dihydro-3-methyl-7-oxo-7H-pyrido[1,2,3-de]-1,4-benzoxazine-6-carboxylic acid, mp 229°–231° C. (35f).

EXAMPLE 36

7-[2-(Aminomethyl)-4-thiazolyl]-1-ethyl-6-fluoro-1,4-dihydro-8-methylamino-4-oxo-3-quinolinecarboxylic acid To 500 mg (1.37 mmol) of the 7-[2-(aminomethyl)-4-thiazolyl]-1-ethyl-6,8-difluoro-1,4-dihydro-4-oxo-3-quinolinecarboxylic acid was added 15 ml of 40% aqueous methylamine. The mixture was heated at 50° C. for 72 hours. The solution was taken to pH 6.5 and was filtered to give 350 mg of 7-[2-(aminomethyl)-4-thiazolyl]-1-ethyl-6-fluoro-1,4-dihydro-8-methylamino-4-oxo-3-quinolinecarboxylic acid, mp 194°–195° C.

EXAMPLE 37

1-Ethyl-6-fluoro-1,4-dihydro-8-methoxy-7-[2-[(methylamino)methyl]-4-thiazoly]-4-oxo-3-quinolinecarboxylic acid To 500 mg (1.32 mmol) of 1-ethyl-6,8-difluoro-1,4-dihydro-7-[2-[(methylamino)methyl]-4-thiazoyl]-4-oxo-3-quinolinecarboxylic acid in 30 ml of dry methanol was added 300 mg (2 eq) of potassium t-butoxide. After 24 hours at reflux, the mixture was cooled, diluted with water, brought to pH 6.0, and filtered to give 310 mg of 1-ethyl-6-fluoro-1,4-dihydro-8-methoxy-7-[2-[(methylamino)methyl]-4-thiazoly]-4-oxo-3-quinolinecarboxylic acid, mp 164°–166° C.

In a similar manner 7-[2-(aminomethyl)-4-thiazolyl]-1-ethyl-6-fluoro-1,4-dihydro-8-methoxy-4-oxo-3-quinolinecarboxylic acid, mp 172°–175° C., was prepared; (37a).

EXAMPLE 38

1-Ethyl-6-fluoro-1,4-dihydro-8-hydroxy-7-[2-[(methylamino)methyl]-4-thiazolyl]-4-oxo-3-quinolinecarboxylic acid To 700 mg (1.79 mmol) of the 1-ethyl-6-fluoro-1,4-dihydro-8-methoxy-7-[2-[(methylamino)methyl]-4-thiazolyl]-4-oxo-3-quinolinecarboxylic acid was added 8 ml of hydrobromic acid in acetic acid and the mixture was heated to 70° C. After four hours 8 ml more hydrobromic acid was added and the mixture stirred overnight. The solids were collected, dissolved in aqueous ammonia and concentrated to one fourth volume. Filtration gave 580 mg of 1-ethyl-6-fluoro-1,4-dihydro-8-hydroxy-7-[2-[(methylamino)methyl]-4-thiazolyl]-4-oxo-3-quinolinecarboxylic acid, mp 242°–246° C.

In similar manner 7-[2-(aminomethyl)-4-thiazolyl]-1-ethyl-6-fluoro-1,4-dihydro-8-hydroxy-4-oxo-3-quinoline carboxylic acid, mp 275°–277° C., was prepared (38a).

EXAMPLE 39

7-[4-(Aminomethyl)-2-thiazolyl]-1-ethyl-6-fluoro-1,4-dihydro-4-oxo-3-quinolinecarboxylic acid A solution of 0.16 g (0.5 mmol) ethyl-1-ethyl-6-fluoro-7-thiocarbamoyl-1,4-dihydro-4-oxo-3-quinolinecarboxylate and 0.32 g (2.5 mmol) 1,3-dichloroacetone in 3 ml N,N-dimethylformamide was heated 3.5 hours on a steam bath. Dilution of the cooled reaction mixture with ethyl acetate afforded 0.12 g product which was recrystallized from chloroform:ethyl acetate to give 0.08 g of ethyl 7-[4-(chloromethyl)-2-thiazolyl]-1-ethyl-6-fluoro-1,4-dihydro-4-oxo-3-quinolinecarboxylate, mp 214°–215° (dec).

A mixture of 1.10 g (2.78 mmol) ethyl 7-[4-(chloromethyl)-2-thiazolyl]-1-ethyl-6-fluoro-1,4-dihydro-4-oxo-3-quinolinecarboxylate and 0.50 g (7.6 mmol) sodium azide in 50 ml N,N-dimethylformamide was heated on a steam bath four hours. After evaporation to near dryness 50 ml water was added to afford 1.01 g product which was crystallized from ethanol to give 0.91 g ethyl 7-[4-(azidomethyl)-2-thiazolyl]-1-ethyl-6-fluoro-1,4-dihydro-4-oxo-3-quinolinecarboxylate, mp 192°–194° (dec);

A solution of 0.87 g (2.17 mmol) ethyl 7-[4-(azidomethyl)-2-thiazolyl]-1-ethyl-6-fluoro-1,4-dihydro-4-oxo-3-quinolinecarboxylate in 125 ml acetic acid was stirred with 0.10 g 10% palladium on carbon catalyst and hydrogen gas bubbled through for 1.5 hours. After filtration, evaporation of solvent and trituration with ether gave 0.77 g of ethyl 7-[4-(aminomethyl)-2-thiazolyl]-1-ethyl-6-fluoro-1,4-dihydro-4-oxo-3-quinolinecarboxylate.

A solution of 0.70 g (1.87 mmol) ethyl 7-[4-(aminomethyl)-2-thiazolyl]-1-ethyl-6-fluoro-1,4-dihydro-4-oxo-3-quinolinecarboxylate in 15 ml 6N hydrochloric acid was heated on a steam bath 2.25 hours. After addition of 15 ml water the mixture was cooled to 0° and filtered. The collected solid was suspended in 8 ml water, dissolved at pH 11 with 2N sodium hydroxide and reprecipitated by addition of 2N hydrochloric acid to pH 6. The product (0.37 g) was twice crystallized from N,N-dimethylformamide to afford 0.19 g of 7-[4-(aminomethyl)-2-thiazolyl]-1-ethyl-6-fluoro-1,4-dichloro-4-oxo-3-quinolinecarboxylic acid, mp 224°–226° C. (dec).

EXAMPLE 40

1-Ethyl-6-fluoro-1,4-dihydro-7-[4-[(methylamino)methyl]-2-thiazolyl]-4-oxo-3-quinolinecarboxylic acid A solution of 0.61 g (1.54 mmol) 7-(4-chloromethyl-2-thiazolyl)-1-ethyl-6-fluoro-1,4-dihydro-4-oxo-3-quinolinecarboxylic acid ethyl ester in 20 ml 6 N hydrochloric acid was refluxed 2 hours and evaporated to dryness. The resulting solid was suspended in hot water, filtered and dried to afford 0.48 g crude product, 7-(4-chloro-methyl-2-thiazolyl)-1-ethyl-6-fluoro-1,4-dihydro-4-oxo-3-quinolinecarboxylic acid.

A solution of 0.40 g 7-(4-chloromethyl-2-thiazolyl)-1-ethyl-6-fluoro-1,4-dihydro-4-oxo-3-quinolinecarboxylic acid in 100 ml 40% aqueous methylamine was stirred at room temperature overnight and evaporated to dryness. The resulting solid was crystallized from water to afford 0.33 g of the title compound, mp 216°–218° C. (dec).

Analysis calculated for $C_{17}H_{16}N_3FO_3S.0.2H_2O$: C, 55.94; H, 4.53; N, 11.51. Found: C, 55.92; H, 4.41; N, 11.18.

EXAMPLE 41

7-(2-Amino-4-pyrimidinyl)-1-ethyl-6-fluoro-1,4-dihydro-4-oxo-3-quinolinecarboxylic acid To 900 mg (2.5 mmol) of the 7-(2′-dimethylaminoethenyl)carbonyl-1-ethyl-6-fluoro-1,4-dihydro-4-oxo-3-quinolinecarboxylic acid ethyl ester in 15 ml of t-butanol at 50° C. was added 580 mg (2.5 eq) of guanidine hydrochloride that had been previously treated with 1.35 g (5 eq) of potassium t-butoxide at 50° C. in t-butanol for 30 minutes. The final mixture was stirred for 24 hours at 60° C. It was poured into 8% aqueous acetic acid and extracted into chloroform. The chloroform was extracted three times with water. The chloroform was dried magnesium sulfate and concentrated. The residue was purified by column chromatography and gave 295 mg of 7-(2-amino-4-pryimidinyl-1-ethyl-6-fluoro-1,4-dihydro-4-oxo-3-quinolinecarboxylic acid, mp 245°–247° C.

EXAMPLE 42

7-[2-(aminomethyl)-4-pyrimidinyl]-1-ethyl-6,8-difluoro-1,4-dihydro-4-oxo-3-quinolinecarboxylic acid To 1.5 g (4.1 mmol) of the ethyl 7-(2′-dimethylaminoethenyl)carbonyl-1-ethyl-6,8-difluoro-1,4-dihydro-4-oxo-3-quinolinecarboxylate in 35 ml of t-butanol was added at 60° C. a mixture of 2.49 g 2.5 equivalents) of 2-N-(benzyloxycarbonyl)aminoacetamidine hydrochloride, and 1.15 g (2.5 eq) of potassium t-butoxide in 50 ml of t-butanol. After four hours, 452 mg more of potassium t-butoxide was added. The mixture was stirred overnight at 60° C. It was poured into dilute hydrochloric acid and extracted with dichloromethane. The dichloromethane was concentrated and the residue was purified by column chromatography to give 530 mg of 1-ethyl-6,8-difluoro-1,4-dihydro-4-oxo-7-[2-[[(phenylmethoxy)carbonyl]aminomethyl]-4-pyrimidinyl]-3-quinolinecarboxylic acid as a yellow solid, mp 195°–196° C. This material was then treated with hydrobromic acid in acetic acid, for three hours. The mixture was poured into ethylacetate:diethyl ether. The solids were filtered and then dissolved in aqueous ammonia pH 10.8° C. This mixture was concentrated to one fourth volume and the solids filtered to give 173 mg of 7-[2-(aminomethyl)-4-pyrimidinyl]-1-ethyl-6,8-difluoro-1,4-dihydro-4-oxo-3-quinolinecarboxylic acid, mp 285°–289° C.

In a similar fashion the 7-(2-amino-4-pyrimidinyl)-1-ethyl-6,8-difluoro-1,4-dihydro-4-oxo-3-quinolinecarboxylic acid, mp 285°–286° C. (42a) was prepared using guanidine hydrochloride and ethyl 7-(2′-dimethylaminoethenyl)carbonyl-1-ethyl-6,8-difluoro-1,4-dihydro-4-oxo-3-quinolinecarboxylate.

Also the 7-[2-(aminomethyl)-4-pyrimidinyl]-1-ethyl-6-fluoro-1,4-dihydro-4-oxo-3-quinolinecarboxylic acid, mp 206°–208° C. (42b), was prepared from 2-N-(benzyloxycarbonyl)aminoacetamidine hydrochloride and ethyl 7-(2′-dimethylaminoethenyl)carbonyl-1-ethyl-6-fluoro-1,4-dihydro-4-oxo-3-quinolinecarboxylate.

Similarly prepared was 7-[2-[(methylamino)methyl]-4-pyrimidinyl]-1-ethyl-6-fluoro-1,4-dihydro-4-oxo-3-quinolinecarboxylic acid, mp 238°–239° C. (42c) from 2-N-(benzyloxycarbonyl)methylaminoacetamidine hydrochloride and ethyl 7-(2′-dimethylaminoethenyl)carbonyl-1-ethyl-6-fluoro-1,4-dihydro-4-oxo-3-quinolinecarboxylate.

EXAMPLE 43

7-[3-(aminomethyl)-1-pyrrolidinyl]-1-cyclopropyl-6,8-difluoro-1,4-dihydro-4-oxo-3-quinolinecarboxylic acid A mixture of 1.00 g (3.53 mmole) of 1-cyclopropyl-6,7,8-trifluoro-1,4-dihydro-4-oxo-3-quinolinecarboxylic acid, 10 ml of acetonitrile, 0.54 g (3.5 mmole) 1,8-diazobicyclo[5.4.0]undec-7-ene, and 0.37 g (3.7 mmole) of 3-pyrrolidinemethanamine is refluxed one hour, then stirred at room temperature overnight. The reaction mixture is then filtered and the precipitate washed with ethyl ether until dry to yield 1.21 g (94.5%) of the title compound, mp 232°–235° C.

EXAMPLE 44

1-Cyclopropyl-7-[3-[(ethylamino)methyl]-1-pyrrolidinyl]-6,8-difluoro-1,4-dihydro-4-oxo-3-quinolinecarboxylic acid A mixture of 1.00 g (3.53 mmole) of 1-cyclopropyl-6,7,8-trifluoro-1,4-dihydro-4-oxo-3-quinolinecarboxylic acid, 10 ml of acetonitrile, 0.54 g (3.5 mmole) 1,8-diazobicyclo[5.4.0]undec-7-ene, and 0.48 g (3.7 mmole) of N-ethyl-3-pyrrolidinemethanamine is refluxed one hour, then stirred at room temperature overnight. The reaction mixture is then filtered and the precipitate washed with ethyl ether until dry to yield 1.22 g (88.4%) of the title compound, mp 256°–258° C.

EXAMPLE 45

7-[3-Amino-1-pyrrolidinyl]-1-cyclopropyl-6,8-difluoro-1,4-dihydro-4-oxo-3-quinolinecarboxylic Acid

7-[3-t-Butoxycarbonylamino-1-pyrrolidinyl]-1-cyclopropyl-6,8-difluoro-1,4-dihydro-4-oxo-3-quinolinecarboxylic Acid A suspension of 49.5 g (0.175 mole) of 1-cyclopropyl-1,4-dihydro-4-oxo-6,7,8-trifluoroquinoline-3-carboxylic acid, 37.3 g (0.2 mole) of 1,1dimethylethyl (3-pyrrolidinyl)carbamate, 40.4 g (0.4 mole) of triethylamine in 1.5 l of acetonitrile was refluxed for three hours. The precipitate was removed by filtration, washed with acetonitrile, then ethyl ether, and dried in vacuo to give 75.0 g of the title compound, mp 239°–240° C.

7-[3-Amino-1-pyrrolidinyl]-1-cyclopropyl-6,8-difluoro-1,4-dihydro-4-oxo-3-quinolinecarboxylic Acid A solution of 1.4 g (3.1 mmole) of 7[3-t-butoxycarbonylamino-1-pyrrolidinyl]-1-cyclopropyl-6,8-difluoro-1,4-dihydro-4-oxo-3-quinolinecarboxyic acid in 25 ml of trifluoroacetic acid was stirred at room temperature until gas evolution ceased. The solvent was removed in vacuo and the residue dissolved in 1 N sodium hydroxide. The solution was diluted to 100 ml with water and acidified to pH 5.5 with 6 N hydrochloric acid. The precipitate was removed by filtration, washed with water, ethanol, and ethyl ether. The residue was dried in vacuo to give 1.05 g (97%) of the title compound, mp 290°–292° C.

7-[3-amino-1-pyrrolidinyl]-1-cyclopropyl-6,8-difluoro-1,4-dihydro-4-oxo-3-quinolinecarboxylic Acid Hydrochloride A suspension of 72.4 g (0.16 mole) of 7-[3-t-butoxycarbonylamino-1-pyrrolidinyl]-1-cyclopropyl-6,8-difluoro-1,4-dihydro-4-oxo-3-quinolinecarboxylic acid, 375 ml of 6 M hydrochloric acid, and 750 ml of glacial acetic acid was heated at 60° C. for four hours and the resulting solution was stirred at room temperature for 18 hours. The reaction was filtered through a fiber glass pad to clarify and the filtrate was evaporated in vacuo. The residue was triturated with 600 ml of ethanol:ether (1:1), the solid removed by filtration, washed with ethanol:ether (1:1), ether and dried in vacuo to give 63.8 g (98%) of the title compound, mp 313°–315° C.

EXAMPLE 46

1-Cyclopropyl-7-[3-[(methylamino)methyl]-1-pyrrolidinyl]-6,8-difluoro-1,4-dihydro-4-oxo-3-quinolinecarboxlic acid To 0.80 g (2.8 mmol) of the 1-cyclopropyl-6,7,8-trifluoro-1,4-dihydro-4-oxo-3-quinolinecarboxylic acid in 10 ml of acetonitrile and 0.43 g (2.8 mmol) of 1,8-diazobicyclo [5.4.0]undec-7-ene, was added 0.35 g (3.1 mmol) of N-methyl-3-pyrrolidinemethanamine. The mixture was refluxed for one hour and stirred overnight. The solids were filtered and washed with acetonitrile: ether (1:6) to give 0.81 g of the title compound, mp 265°–267° C.

EXAMPLE 47

1-Cyclopropyl-7-[3-(ethylamino)-1-pyrrolidinyl]-6,8-difluoro-1,4-dihydro-4-oxo-3-quinolinecarboxylic acid To 0.80 g (2.8 mmol) of the 1-cyclopropyl-6,7,8-trifluoro-1,4-dihydro-4-oxo-3-quinolinecarboxylic acid in 10 ml of acetonitrile and 0.43 g (2.8 mmol) of 1,8-diazobicyclo [5.4.0]undec-7-ene was added 0.35 g (3.1 mmol) of the N-ethyl-3-aminopyrrolidine. The mixture was refluxed for one hour and stirred overnight. The solids were filtered and washed with ether: acetonitrile (6:1), to give 0.81 g of the title compound, mp 236°–238° C.

EXAMPLE 48

1-Cyclopropyl-6,8-difluoro-1,4-dihydro-7-[3-[[(1-methylethyl)amino]methyl]-1-pyrrolidinyl]-4-oxo-3-quinolinecarboxylic acid A suspension of 1.1 g (3.9 mmole) of 1-cyclopropyl-6,7,8-trifluoro-1,4-dihydro-4-oxo-3-quinolinecarboxylic acid, 1.4 g (10 mmole) of N-(2-propyl)-3-pyrrolidinemethanamine and 50 ml of acetonitrile was refluxed for 2 hours. The precipitate was removed by filtration, washed with acetonitrile, ether, and dried 221° C.

EXAMPLE 49

1-Cyclopropyl-7-[3-[(ethylamino)methyl]-1-pyrrolidinyl]-6-chloro-1,4-dihydro-4-oxo-3-quinolinecarboxylic acid A solution of 0.30 g (1.0 mmole) of 6,7-dichloro-1-cyclopropyl-1,4-dihydro-4-oxo-3-quinolinecarboxylic acid, 0.26 g (2.0 mol) of N-ethyl-3-pyrrolidinemethanamine and 10 ml of 3-picoline was heated under reflux for 16 hours. The reaction mixture was cooled to room temperature and the solid filtered off and washed with acetonitrile to give 0.33 g of the title compound, mp >310° C.

EXAMPLE 50

The following compounds may be prepared from 7-chloro-1-cyclopropyl-6-fluoro-1,4-dihydro-4-oxoquinoline-3-carboxylic acid (synthesized as described in European Patent Publication No. 78362) and the desired amine or protected amine using the method of Example 49:

7-[3-(aminomethyl)-1-pyrrolidinyl]-1-cyclopropyl-6-fluoro-1,4-dihydro-4-oxo-3-quinolinecarboxylic acid; and 7-[3-amino-1-pyrrolidinyl]-1-cyclopropyl-6-fluoro-1,4-dihydro-4-oxo-3-quinolinecarboxylic acid.

EXAMPLE 51

(S)-1-Ethyl-7-[3-[(ethylamino)methyl]-1-pyrrolidinyl]-6,8-difluoro-1,4-dihydro-4-oxo-3-quinolinecarboxylic Acid A solution of 2.17 g (8 mmol) 1-ethyl-6,7,8-trifluoro-1,4-dihydro-4-oxo-3-quinolinecarboxylic acid and 1.22 g (8 mmol), 1,8-diazabicyclo[5.4.0]undec-7-ene in 20 ml acetonitrile was treated with 1.07 g (8.4 mmol) (S)-N-ethyl-3-pyrrolidinemethanamine and refluxed one hour. After standing overnight at room temperature a white solid was filtered and washed with acetonitrile and ether to afford 2.25 g (74%) of the free base of the title compound after recrystallization from acetonitrile, mp 193°–195° C. The product was dissolved in dilute hydrochloric acid, lyophilized and stirred as a suspension in ethanol to afford the title compound, 2.11 g (70%), mp 280° C. (decomposition), $[\alpha]_D -99.1°$ C. (C, 1.00, 0.1N NaOH).

Anal. calcd. for $C_{19}H_{24}N_3ClF_2O_3$: C, 54.87; H, 5.82; N, 10.10; Cl, 8.53. Found: C, 55.02; H, 5.91; N, 10.11; Cl, 8.85.

(R)-1-Ethyl-7-[3-[(ethylamino)methyl]-1-pyrrolidinyl]-6,8-difluoro-1,4-dihydro-4-oxo-3-quinolinecarboxylic Acid In the same manner as described above (R)-1-ethyl-7-[3-[(ethylamino)methyl]-1-pyrrolidinyl]-6,8-difluoro-1,4-dihydro-4-oxo-3-quinolinecarboxylic acid hydrochloride, mp 285° C. (decomposition), $[\alpha]_D +92.8°$ C. (C, 1.03, 0.1N NaOH), was prepared by converting [3S-(R*,S*)]-methyl 5-oxo-1-(1-phenylethyl)-3-pyrrolidinecarboxylate (mp 69°–71° C., $[\alpha]_D +118.8°$ C. (C, 1.21, methanol) into (R)-N-ethyl-3-pyrrolidine methanamine dichloride, mp 181°–183° C., $[\alpha] -5.1°$ C. (C, 0.78, 0.1 N NaOH) (Example QQ) and subsequently reacting with 1-ethyl-6,7,8-trifluoro-1,4-dihydro-4-oxo-3-quinolinecarboxylic acid.

EXAMPLE 52

7-[3-[Dimethylamino)methyl]-1-pyrrolidinyl]1-ethyl-6,8-difluoro-1,4-dihydro-4-oxo-3-quinolinecarboxylic Acid A mixture of 0.6 g (2.2 mmole) of 1-ethyl-6,7,8-trifluoro-1,4-dihydro-4-oxo-3-quinolinecarboxylic acid, 5 ml acetonitrile, 0.33 g (2.2 mmole) 1,8-diazobicyclo[5.4.0]undec-7-ene and 0.31 g (2.4 mmole) of N,N-dimethyl-3-pyrrolidinemethamine was refluxed for 24 hours. The reaction was cooled to room temperature, and the formed precipitate was filtered. The precipitate was washed with pentane then ethyl ether until dry yielding 0.59 g (70%) of the title compound, mp 204°–206° C.

EXAMPLE 53

7-[3-[(Diethylamino)methyl]-1-pyrrolidinyl]-1-ethyl-6,8-difluoro-1,4-dihydro-4-oxo-3-quinolinecarboxylic Acid.

A mixture of 0.5 g (1.8 mmole) 1-ethyl-6,7,8-trifluoro-1,4-dihydro-4-oxo-3-quinolinecarboxylic acid, 5 ml acetonitrile, 0.27 g (1.8 mole) of 1,8-diazobicyclo[5.4.0]undec-7-ene, and 0.3 g (1.9 mmole) of N,N-diethyl-3-pyrrolidinemethanamine was stirred at room temperature overnight. The formed precipitate was filtered, washed with acetonitrile then ethyl ether until dry to yield 0.45 g (60%) of the title compound, mp 210°–211° C.

EXAMPLE 54

7-[3-Amino-1-pyrrolidinyl]-1-cyclopropyl-6-fluoro-1,4-dihydro-4-oxo-1,8-naphthyridine-3-carboxylic Acid A suspension of 5.65 g (20 mmole) of 7-chloro-1-cyclopropyl-6-fluoro-1,4-dihydro-4-oxo-1,8-naphthyridine-3-carboxylic acid, 4.65 g (25 mmole) of 3-t-butoxycarbonylaminopyrrolidine, 7.9 g (50 mmole) of 1,8-diazabicyclo[5.4.0]undec-7-ene and 150 ml of acetonitrile was stirred at 60° C. for one hour. The solvent was removed in vacuo and the residue was dissolved in 100 ml of trifluoroacetic acid. After stirring at room temperature for one hour, the solvent was removed in vacuo and the residue was suspended in water and the pH adjusted to 11.5 with 50% sodium hydroxide. After filtering through a fiber glass pad to clarify, the filtrate was acidified to 6.6 with 6 M hydrochloric acid. The resulting precipitate was removed by filtration, washed with water, 2-propanol, ether and dried in vacuo to give 6.5 g (98%) of the title compound, mp 284°–286° C.

EXAMPLE 55

7-[(3-Aminomethyl)-1-pyrrolidinyl]-1-cyclopropyl-6-fluoro-1,4-dihydro-4-oxo-1,8-naphthyridine-3-carboxylic Acid A suspension of 5.1 g (18 mmole) of 7-chloro-1-cyclopropyl-6-fluoro-1,4-dihydro-4-oxo-1,8-napthyridine-3-carboxylic acid, 2.0 g (20 mmole) of 3-aminomethylpyrrolidine, 5.5 g (36 mmole) of 1,8-diazabicyclo [5.4.0]undec-7-ene and 125 ml of acetonitrile was stirred at room temperature for three hours. The precipitate was removed by filtration, washed with acetonitrile, and dried in vacuo to give 4.35 g (70%) of the title compound, mp 210°–212° C.

EXAMPLE 56

7-[3-[(Ethylamino)methyl]-1-pyrrolidinyl]-1-cyclopropyl-6-fluoro-1,4-dihydro-4-oxo-1,8-naphthyridine-3-carboxylic Acid A suspension of 5.7 g (20 mmole) of 7-chloro-1-cyclopropyl-6-fluoro-1,4-dihydro-4-oxo-1,8-naphthyridine-3-carboxylic acid, 10.3 (80 mmole) of 3-ethylaminomethylpyrrolidine and 125 ml of acetonitrile was stirred at room temperature for 0.5 hours after an initial exotherm (60° C.). The solid was removed by filtration, washed with acetonitrile, and dried in vacuo to give 6.0 g (80%) of the title compound, mp 268°–270° C.

EXAMPLE 57

7-[3-[(2-Propylamino)methyl]-1-pyrrolidinyl]-1-cyclopropyl-6-fluoro-1,4-dihydro-4-oxo-1,8-napthyridine-3-carboxylic Acid A suspension of 1.13 g (3.0 mmole) of 7-chloro-1-cyclopropyl-6-fluoro-1,4-dihydro-4-oxo-1,8-naphthyridine-3-carboxylic acid, 0.63 g (4.4 mmole) of 3-[(2-propyl)aminomethyl]pyrrolidine, 1.22 g (8.0 mmole) of 1,8-diazabicyclo[5.4.0]undec-7-ene and 30 ml of acetonitrile was stirred at room temperature for two hours. The precipitate was removed by filtration, washed with acetonitrile, and dried in vacuo to give 1.3 g (84%) of the title compound, mp 240°–243° C.

EXAMPLE 58

7-[3-[(Propylamino)methyl]-1-pyrrolidinyl]-1-cyclopropyl-6-fluoro-1,4-dihydro-4-oxo-1,8-naphthyridine-3-carboxylic Acid A suspension of 1.13 g (4.0 mmole) of 7-chloro-1-cyclopropyl-6-fluoro-1,4-dihydro-4-oxo-1,8-naphthyridine-3-carboxylic acid, 0.63 g (4.4 mmole) of 3-[(propylamino)methyl]pyrrolidine, 1.22 g (8.0 mmole) of 1,8-diazabicyclo[5.4.0]undec-7-ene and 30 ml of acetonitrile was stirred at room temperature for 2.5 hours. The precipitate was removed by filtration, washed with acetonitrile and dried in vacuo to give 1.15 g (74%) of the title compound, mp 230°–233° C.

EXAMPLE 59

7-[2-(Aminomethyl)-1-azetidinyl]-1-ethyl-6-fluoro-1,4-dihydro-4-oxo-1,8-naphthyridine-3-carboxylic Acid A suspension of 1.08 g (4.0 mmol) of 7-chloro-1-ethyl-6-fluoro-1,4-dihydro-4-oxo-1,8-naphthyridine-3-carboxylic acid, 0.93 g (5.0 mmol) of 2-[(t-butoxycarbonylamino)methyl]azetidine, 1.01 g (10 mmol) of triethylamine and 50 ml of acetonitrile was stirred at reflux for two hours. The solvent was removed in vacuo and the residue was dissolved in 25 ml of trifluoroacetic acid. After stirring at room temperature for two hours, the solvent was removed in vacuo. The residue was suspended in water and the pH adjusted to 11 with 10% sodium hydroxide. The resulting solution was filtered through a fiber glass pad to clarify and the filtrate acidified to pH 7.2 with 1 M hydrochloric acid. The resulting precipitate was removed by filtration, washed successively with water, ethanol, ether and dried in vacuo to give 0.66 g (52%) of the title compound, mp 198°–200° C.

EXAMPLE 60

7-[3-[(Ethylamino)methyl]-1-pyrrolidinyl]-6,8-difluoro-1,4-dihydro-4-oxo-1-(2,2,2-trifluoroethyl)-3-quinolinecarboxylic Acid To 0.76 g (2.33 mmol) of 6,7,8-trifluoro-1-(2,2,2-trifluoroethyl)-1,4-dihydro-4-oxo-3-quinolinecarboxylic acid in 7.0 ml of acetonitrile was added 0.355 g (2.33 mmol) of 1,8-diazabicyclo [5.4.0]undec-7-ene in 5 ml of acetonitrile followed by 0.29 g (2.33 mmol) of 3-[(ethylamino)methyl]pyrrolidine. The mixture was refluxed for one hour and kept at room temperature overnight. The solids were collected and washed with ether to give 0.77 g of 7-[3-[(ethylamino)methyl]-1-pyrrolidinyl]-6,8-difluoro-1,4-dihydro-4-oxo-1-(2,2,2-trifluoroethyl)-3-quinolinecarboxylic acid, mp 222°–224° C.

EXAMPLE 61

7-[3-[(Ethylamino)methyl]-1-pyrrolidinyl]-6,8-difluoro-1,4-dihydro-1-(1-methylcyclopropyl)-4-oxo-3-quinolinecarboxylic Acid To 0.75 g (2.57 mmol) of 6,7,8-trifluoro-1,4-dihydro-1-(1-methylcyclopropyl)-4-oxo-3-quinolinecarboxylic acid in 15.0 ml of acetonitrile was added 0.38 g (2.57 mmol) of 1,8-diazobicyclo[5.4.0]undec-7-ene and 0.32 g (2.57 mmol) of 3-[(ethylamino)methyl]pyrrolidine. The mixture was refluxed for two hours and was cooled and filtered. The solids were washed with ether to afford 0.76 g of 7-[3-[(ethylamino)methyl]-1-pyrrolidinyl]-6,8- difluoro 1,4-dihydro-1-(1-methylcyclopropyl)-4-oxo-3-quinolinecarboxylic acid, mp 261°–263° C.

EXAMPLE 62

7-[3-[(Ethylamino)methyl]-1-pyrrolidinyl]-6,8-difluoro-1,4-dihydro-1-(2-methylcyclopropyl)4-oxo-3-quinolinecarboxylic Acid To 0.75 g (2.57 mmol) of 6,7,8-trifluoro-1,4-dihydro-1-(2-methylcyclopropyl)-4-oxo-3-quinolinecarboxylic acid in 15 ml of acetonitrile was added 0.38 g (2.57 mmol) of 1,8-diazobicyclo[5.4.0]undec-7-ene and 0.32 g (2.57 mmol) of 3-[(ethylamino)methyl]pyrrolidine. The mixture was refluxed for two hours, cooled, filtered, and the solids washed with ether to give 0.84 g of 7-[3-[(ethylamino)methyl]-1-pyrrolidinyl]-6,8-difluoro-1,4-dihydro-1-(2-methylcyclopropyl)4-oxo-3-quinolinecarboxylic acid, mp 225°–228° C.

EXAMPLE 63

7-(3-Amino-1-pyrrolidinyl)-6,8-difluoro-1,4-dihydro-1-(2-methylcyclopropyl)-4-oxo-3-quinolinecarboxylic Acid To 0.47 g (1.58 mmol) of 6,7,8-trifluoro-1,4-dihydro-1-(2-methylcyclopropyl)-4-oxo-3-quinolinecarboxylic acid in 10 ml of acetonitrile was added 0.24 g (1.58 mmol) of 1,8-diazobicyclo [5.4.0]undec-7-ene and 0.30 g (1.61 mmol) of 3-[(t-butoxycarbonyl)amino]pyrrolidine. The mixture was refluxed for two hours, filtered, and washed with ether to give 1.18 g of solid which was dissolved in 10 ml acetic acid. The mixture was heated to 100° and 4 ml of 3N hydrochloric acid was added. Concentration gave 0.14 g of 7-(3-amino-1-pyrrolidinyl)-6,8-difluoro-1,4-dihydro-1-(2-methylcyclopropyl)-4-oxo-3-quinolinecarboxylic acid as the hydrochloride salt, mp 267°–275° C.

EXAMPLE 64

1-(Cyclopropylmethyl)-7-[3-[(ethylamino)methyl]-1-pyrrolidinyl]-6,8-difluoro-1,4-dihydro-4-oxo-3-quinolinecrboxylic Acid To 1.0 g (3.36 mmol) of 1-(cyclopropylmethyl)-6,7,8-trifluoro-1,4-dihydro-4-oxo-3-quinolinecarboxylic acid in 8 ml of acetonitrile was added 0.51 g (3.36 mmol) of 1,8-diazobicyclo[5.4.0]undec-7-ene and 0.43 g (3.36 mmol) of 3-[(ethylamino)methyl]-1-pyrrolidine each in 1 ml of acetonitrile. The mixture was refluxed for two hours and stirred overnight at room temperature. The mixture was filtered, and washed with ether to give 0.935 g of 1-(cyclopropylmethyl)-7-[3-[(ethylamino)methyl]-1-pyrrolidinyl]-6,8-difluoro-1,4-dihydro-4-oxo-3-quinolinecrboxylic acid, mp 185°–188° C.

EXAMPLE 65

1-Cyclobutyl-7-[3-[(ethylamino)methyl]-1-pyrrolidinyl]-6,8-difluoro-1,4-dihydro-4-oxo-3-quinolinecarboxylic Acid To 0.76 g (2.7 mmol) of the 1-cyclobutyl-6,7,8-trifluoro-1,4-dihydro-4-oxo-3-quinolinecarboxylic acid in 10 ml of acetonitrile was added 0.4 g (2.7 mmol) of 1,8-diazobicyclo[5.4.0]undec-7-ene and 0.36 g (2.7 mmol and 0.36 g (2.7 mmol) of 3-[(ethylamino)methyl]-pyrrolidine. The mixture was refluxed for 3.5 hours, cooled, filtered, and washed with ether to give 0.74 g of 1-cyclobutyl-7-[3-[(ethylamino)methyl]-1-pyrrolidinyl]-6,8-difluoro-1,4-dihydro-4-oxo-3-quinolinecarboxylic acid, mp 223°–225° C.

EXAMPLE 66

1-Cyclopentyl-7-[3-[(ethylamino)methyl]-1-pyrrolidinyl]-6,8-difluoro-1,4-dihydro-4-oxo-3-quinolinecarboxylic Acid To 0.86 g (2.7 mmol) of the 1-cyclopentyl-6,7,8-trifluoro-1,4-dihydro-4-oxo-3-quinolinecarboxylic acid in 10 ml of acetonitrile was added 0.40 g (2.7 mmol) of 1,8-diazobicyclo [5.4.0]undec-7-ene and 0.36 g (2.7 mmol) of 3-[(ethylamino)methyl]pyrrolidine. The mixture was refluxed for seven hours, cooled, filtered, and the solids washed with ether to give 0.84 g of 1-cyclopentyl-7-[3-[(ethylamino)methyl]-1-pyrrolidinyl]-6,8-difluoro-1,4dihydro-4-oxo-3-quinolinecarboxylic acid, mp 214°–217° C.

EXAMPLE 67

1-Ethyl-7-[3-(ethylamino)-1-pyrrolidinyl]-6,8-difluoro-1,4-dihydro-4-oxo-3-quinolinecarboxylic Acid To 1.0 g (3.7 mmol) of 1-ethyl-6,7,8-trifluoro-1,4-dihydro-4-oxo-3-quinolinecarboxylic acid in 10 ml of acetonitrile was added 0.56 g (3.7 mmol) of 1,8-diazobicyclo[5.4.0]undec-7-ene and 0.44 g (3.7 mmol) of 3-(ethylamino)pyrrolidine. The mixture was refluxed for one hour, kept overnight at room temperature, filtered, and the solid washed with ether to give 0.81 g of 1-ethyl-7-[3-(ethylamino)-1-pyrrolidinyl]-6,8-difluoro-1,4-dihydro-4-oxo-3-quinoline carboxylic acid, mp 227°–229° C.

EXAMPLE 68

7-(3-Amino-1-pyrrolidinyl)-6,8-difluoro-1,4-dihydro-1-(1-methylcyclopropyl)-4-oxo-3-quinolinecarboxylic Acid To 1.24 g (4.27 mmol) of 6,7,8-trifluoro-1,4-dihydro-1-(1-methylcyclopropyl)-4-oxo-3-quinolinecarboxylic acid in 10 ml of acetonitrile was added 0.77 (4.27 mmol) of 3-[(t-butoxycarbonyl)amino]pyrrolidine and 0.63 g (4.27 mmol) of 1,8-diazobicyclo[5.4.0]undec-7-ene. The mixture was refluxed for one hour, cooled, filtered, and the solids washed with ether. The solids were dissolved in 10 ml of acetic acid at 100° C. and 2 ml of 3N hydrochloric acid was added. This mixture was heated at 100° for four hours, concentrated, triturated with 2-propanol, and the solid filtered, washed with ether, and dried (24 hours, 80° C., 125 mmHg) to give 0.90 g of 7-(3-amino-1-pyrrolidinyl)-6,8-difluoro-1,4-dihydro-1-(1-methylcyclopropyl)-4-oxo-3quinolinecarboxylic acid as the hydrochloride salt, mp >300° C.

EXAMPLE 69

1-Cyclohexyl-7-[3-[(ethylamino)methyl]-1-pyrrolidinyl]-6,8-difluoro-1,4-dihydro-4-oxo-3-quinolinecarboxylic Acid To 0.80 g (2.46 mmol) of 1-cyclohexyl-6,7,8-trifluoro-1,4-dihydro-4-oxo-3-quinolinecarboxylic acid in 15 ml of acetonitrile was added 0.37 g (2.46 mmol) of 1,8-diazobicyclo[5.4.0]undec7-ene and 0.33 g (2.58 mmol) of 3-[(ethylamino)methyl]pyrrolidine. The mixture was refluxed for one hour, cooled, filtered, and the solids washed with ether to give 0.86 g of 1-cyclohexyl-7-[3-[(ethylamino)methyl]-1-pyrrolidinyl]-6,8-difluoro-1,4-dihydro-4-oxo-3-quinolinecarboxylic acid, mp 194°–196° C.

EXAMPLE 70

7-[3-[(Ethylamino)methyl]-1-pyrrolidinyl]-6,8-difluoro-1,4-dihydro-1-(1-methylethyl)-4-oxo-3-quinolinecaroxylic Acid A solution of 0.57 g (2.0 mmol) of 6,7,8-trifluoro-1,4-dihydro-1-(1-methylethyl)-4-oxo-3-quinolinecarboxylic acid, 0.32 ml (2.2 mmol) of 3-[(ethylamino)methyl]pyrrolidine, 0.30 ml (2.0 mmol) of 1,8-diazabicyclo[5.4.0]undec-7-ene and 15 ml of acetonitrile was heated under reflux for one hour. After cooling to room temperature the mixture was filtered and the solid washed with acetonitrile and methanol to give 0.58 g of the title compound, mp 230°-231° C.

EXAMPLE 71

1-Cyclopropyl-7-[3-[(ethylamino)methyl]-1-pyrrolidinyl]-6-fluoro-1,4-dihydro-4-oxo-3-quinolinecarboxylic acid, Hydrochloride A solution of 0.57 g (2.0 mmol) of 7-chloro-1-cyclopropyl-6-fluoro-1,4-dihydro-4-oxo-3-quinolinecarboxylic acid, 0.58 ml (4.0 mmol) of 3-[(ethylamino)methyl]pyrrolidine and 10 ml of 3-picoline was heated under reflux for 17 hours. After cooling to room temperature the mixture was filtered and the solid washed with hot methanol to give 0.42 g of the title compound, mp >300° C.

PREPARATION OF STARTING MATERIALS

EXAMPLE A

Ethyl 7-acetyl-1-ethyl-6-fluoro-1,4-dihydro-4-oxo-3-quinolinecarboxylate

A solution of 26.4 g (0.17 mole) 3-acetyl-4-fluoroaniline and 34.6 ml (0.35 mole) 1,3propanedithiol in 2.5 l chloroform was cooled to 5° C. Hydrogen chloride gas was bubbled into the stirred solution for 15 minutes at 5°-10° C., and the reaction was warmed to room temperature with stirring overnight. The solvent was removed in vacuo at 60° C., and the solid residue twice taken into 800 ml toluene and stripped in vacuo at 60° C. The solid material was dissolved in 1.5 l chloroform, washed twice with 200 ml saturated sodium bicarbonate solution, twice with 200 ml water, and dried with magnesium sulfate. Removal of the solvent in vacuo gave a brown oil, containing 4-fluoro-3-(2-methyl-1,3-dithian-2-yl)benzenamine. This oil was dissolved in 1.2 l toluene, and 34.4 ml (0.17 mole) diethyl ethoxymethylenemalonate was added. The toluene was distilled off over two hours, until the head temperature reached 120°-125° C. The resulting brown oil, containing diethyl [[[4-fluoro-3-(2-methyl-1,3-dithian-2-yl)phenyl]amino]methylene]propanedioate, was poured directly into 500 ml Dowtherm A preheated to 250° C. The temperature of the mixture was raised back to 250° C., and heated 15 minutes. After cooling, the mixture was slowly poured into 2 l pentane and stirred vigorously overnight. The solid was collected, washed well with pentane, and dried, giving 40 g of a light brown solid, ethyl 6-fluoro-1,4-dihydro-7-(2-methyl-1,3-dithian-2-yl)-4-oxo-3-quinolinecarboxylate. Without further purification, this material was treated with 75.3 g, (0.55 mole) potassium carbonate and 43.6 ml (0.55 mole) ethyl iodide in 2.7 l N,N-dimethylformamide at 85° C. overnight. The solvent was removed in vacuo at 65° C., and the residue dissolved in 2 l chloroform, washed well with water, and dried with magnesium sulfate. Removal of solvent in vacuo gave 48.2 g of a light brown solid, ethyl 1-ethyl-6-fluoro-1,4-dihydro-7-(2-methyl-1,3-dithian-2-yl)-4-oxo-3-quinolinecarboxylate. Without further purification, this material was dissolved in 1 l 80% acetonitrile/water, and added over 30 minutes, at room temperature, under nitrogen, to a well-stirred suspension of 28.9 g (0.13 mole) mercuric oxide and 72.9 g (0.27 mole) mercuric chloride in 2 l 80% acetonitrile/water. The reaction was warmed to reflux for six hours under nitrogen, cooled to room temperature, and filtered through a pad of celite. The filter pad was washed with 3 l of 1:1 dichloromethane:hexane. The organic phase of the filtrate was separated, washed twice with 500 ml 5M ammonium acetate solution, twice with 500 ml water, and dried with magnesium sulfate. The solvent was removed in vacuo, and the solid residue was stirred overnight in 1.5 l diethylether. The solid was collected, washed well with diethyl ether, and dried to give 23.4 g of the title compound, ethyl 7-acetyl-1-ethyl-6-fluoro-1,4-dihydro-4-oxo-3-quinolinecarboxylate, mp 106°-108° C.

EXAMPLE B

Ethyl 7-bromoacetyl-1-ethyl-6-fluoro-1,4-dihydro-4-oxo-3-quinolinecarboxylic acid A solution of 2.45 g (8.0 mmol) ethyl 7-acetyl-1-ethyl-6-fluoro-1,4-dihydro-4-oxo-3-quinolinecarboxylate in 50 ml acetic acid was treated with 0.46 g potassium bromate, and then 3.8 ml 48% hydrobromic acid was added dropwise over one half hour. The mixture was stirred 24 hours at room temperature and poured into 200 ml ice water. The precipitate was filtered, washed with water and dried to afford 2.87 g ethyl 7-bromoacetyl-1-ethyl-6-fluoro-1,4-dihydro-4-oxo-3-quinolinecarboxylate.

EXAMPLE C 7-(2'-dimethylaminoethenyl)carbonyl-1-ethyl-6-fluoro-1,4-dihydro-4-oxo-3-quinolinecarboxylic acid ethyl ester To 2.0 (6.5 mmol) of ethyl 7-acetyl-1-ethyl-6-fluoro-1,4-dihydro-4-oxo-3-quinolinecarboxylate in 50 ml of dimethylformamide was added 1.71 ml (1.25 eq) of bis-t-butoxydimethylaminomethane. The mixture was heated at 70° C. for 18 hours. The mixture was then concentrated and the residue treated with ether and filtered to give 1.95 g of 7-(2'-dimethylaminoethenyl)carbonyl-1-ethyl-6-fluoro-1,4-dihydro-4-oxo-3-quinolinecarboxylic acid ethyl ester, mp 176°-179° C.

EXAMPLE D

Ethyl 7-(2'-dimethylaminoethenyl)carbonyl-1-ethyl-6,8-difluoro-1,4-dihydro-4-oxo-3-quinolinecarboxylate To 5.00 g (15.5 mmol) of the ethyl 7-acetyl-1-ethyl-6,8-difluoro-1,4-dihydro-4-oxo-3-quinolinecarboxylate in 65 ml of dimethylformamide was added 4.27 ml (1.3 eq) of bis t-butoxydimethylaminomethane. The mixture was taken to 55° C. overnight. The mixture was concentrated and the solids suspended in ethyl ether. Filtration gave 4.88 g of the ethyl 7-(2'-dimethylaminoethenyl)carbonyl-1-ethyl-6,8-difluoro-1,4-dihydro-4-oxo-3-quinolinecarboxylate, mp 175°-177° C.

EXAMPLE E

7-cyano-1,4-dihydro-1-ethyl-6-fluoro-3-quinolinecarboxylic acid ethyl ester

To a suspension of 2.78 g (10 mmole) of 7-amino-1,4-dihydro-1-ethyl-6-fluoro-3-quinolinecarboxylic acid ethyl ester in 40 ml of 1N HCl at 8° was added a solution of 0.72 g (10.5 mml) of sodium nitrite and 5 ml of water portionwise keeping the temperature at 8° C. The orange solution was stirred at 5° to 8° C. for 0.5 hours. To a solution of 1.07 g (12 mmol) of cuprous cyanide, 2.28 g (35 mmol) of potassium cyanide and 25 ml of water at 45°–50° C. was added the diazonium solution over 10 minutes. The foaming mixture was heated with stirring at 50°–60° C. for 1.25 hours, then treated with 10 ml of 29% ammonium hydroxide and stirred at 50° C. for 20 minutes. The solution was cooled with ice and the solid collected by filtration. The solid was recrystallized from acetonitrile to give acetonitrile filtrate was evaporated to dryness and the residue was triturated with ethers to yield an additional 0.63 g of product.

EXAMPLE F

1-Ethyl-6-fluoro-7-thiocarbamoyl-1,4-dihydro-4-oxo-3-quinolinecarboxylic acid ethyl ester Hydrogen sulfide was passed through a solution of 1.50 g (5.2 mmol) 7-cyano-1-ethyl-6-fluoro-4-oxo-3-quinolinecarboxylic acid ethyl ester in 25 ml pyridine and 1 ml triethylamine for five hours. After stirring overnight in a closed flask, the precipitated solid was filtered, washed with pyridine and ether, and dried to afford 1.28 g of yellowish solid of the title compound, mp 198°–199° C. (dec).

Analysis calculated for: $C_{15}H_{15}N_2O_3FS$: C, 55.88; H, 4.69; N, 8.69; S, 9.95. Found: C, 55.77; H, 4.78; N, 8.43, S, 10.15.

EXAMPLE G

7-Acetyl-1-ethyl-6,8-difluoro-1,4-dihydro-4-oxo-3-quinolinecarboxylic acid

2,6-Difluoroacetophenone

To 64.19 g (455 mmol) of the 2,6-difluorobenzonitrile in 300 ml of diethyl ester was added in one hour at $-78°$ C., 650 ml of 1.6 M methyl lithium (2.0 eq). The mixture was stirred at $-78°$ C. for 2.5 hours, and then treated with 250 ml of 6 N hydrochloric acid. The reaction was brought to 5° C. and allowed to attain room temperature overnight. The layers were separated, then the water layer washed with dichloromethane. The ether and dichloromethane layers were combined, dried, and concentrated to an oil which was purified by column chromatography on silica gel to give 61 g of 2,6-difluoroacetophenone as a light yellow liquid: IR (liquid film) 1709, 1622 cm$^{-1}$.

2,6-Difluoro-3-nitroacetophenone

To 100 ml of concentrated sulfuric acid at 0° was added 17.0 g (109 mmol) of the 2,6-difluoroacetophenone slowly over 20 minutes keeping the temperature at 0°–10° C. To this solution, at $-5°$ C., was added a mixture of 20 ml concentrated sulfuric acid and 6.5 ml of 70% nitric acid premixed at 0° C. before the addition. The nitrating agent was added at a sufficient rate to keep the reaction temperature at 5° C. The reaction was then stirred for 20 minutes and poured over ice. The mixture was extracted with dichloromethane two times. The dichloromethane was dried and concentrated to an oil which was purified by column chromatography to give 14.8 g of 2,6-difluoro-3-nitroacetophenone as a pale yellow oil: IR (liquid film) 1715, 1620, 1590, 1540, 1350 cm$^{-1}$.

Diethyl 3-acetyl-2,4-difluoroanilinomethylenemalonate

To 18.1 g (90.0 mmol) of the 2,6-difluoro-3-nitroacetophenone was added methanol, Raney Nickel, and hydrogen gas. When the mixture had taken up the theoretical amount of hydrogen, it was filtered into an excess of diethyl methylenemalonate. The methanol was removed, and the mixture was treated with toluene which was then distilled away to one half volume. The mixture was then concentrated under vacuum and the residue was stirred with ether:pentane to give 24.4 g of the 3-acetyl-2,4-difluoroanilinomethylene malonate, mp 82°–84° C.

Ethyl 7-acetyl-6,8-difluoro-1,4-dihydro-4-oxo-3-quinolinecarboxylate

To 380 ml of refluxing Dowtherm A was added 14.4 g (42.2 mmol) of 3-acetyl-2,4-difluoroanilinomethylenemalonate in three portions. The reaction was stirred for 30 minutes. After cooling, it was treated with 500 ml of pentane. The solids were filtered and washed with ether:pentane to give 7.9 g of ethyl 7-acetyl-6,8-difluoro-1,4-dihydro-4-oxo-3-quinolinecarboxylate, mp 267°–270° C. This material was used without further purification.

To 22.3 g (76.6 mmol) of the ethyl 7-acetyl-6,8-difluoro-1,4-dihydro-4-oxo-3-quinolinecarboxylate in 900 ml of dimethylformamide was added 25.6 g (2.5 eq) of potassium carbonate and 22 ml (3.6 eq) of ethyl iodide. The mixture was stirred at 45° C. overnight. The mixture was concentrated. The residue was dissolved in water and extracted into dichloromethane. The dichloromethane was concentrated and the residual oil was purified by column chromatography on silica gel to give 10.5 g of ethyl 7-acetyl-1-ethyl-6,8-difluoro-1,4-dihydro-4-oxo-3-quinoline carboxylate, mp 129°–130° C.

To 400 mg (1.23 mmol) of this material was added 5 ml of 6 N hydrochloric acid and the suspension was stirred at 85° C. overnight. Filtration gave 310 mg of 7-acetyl-1-ethyl-6,8-difluoro-1,4-dihydro-4-oxo-3-quinolinecarboxylic acid, mp 250°–251° C.

EXAMPLE H

1-Ethenyl-6,7,8-trifluoro-1,8-dihydro-4-oxo-3-quinolinecarboxylic acid

In similar fashion, when the 6,7,8-trifluoro-1,4-dihydro-4-oxo-3-quinolinecarboxylic acid ethyl ester is treated with dibromo ethane, the 1-ethenyl-6,7,8-trifluoro-1,4-dihydro-4-oxo-3-quinolinecarboxylic acid ester is obtained, mp 134°–135° C. Subsequent hydrolysis with hydrochloric acid gave 1-ethenyl-6,7,8-trifluoro-1,4-dihydro-4-oxo-3-quinolinecarboxylic acid, mp 186°–187° C.

EXAMPLE I

7-(Bromoacetyl)-1-ethyl-6,8-difluoro-1,4-dihydro-4-oxo-3-quinolinecarboxylic acid To 1.12 g (3.80 mmol) of the 7-acetyl-1-ethyl-6,8-difluoro-1,4-dihydro-4-oxo-3-quinolinecarboxylic acid in 30 ml of acetic acid was added 0.18 g of potassium bromate and 1.48 ml of 48% hydrobromic acid. The mixture was stirred at 50° C. for 24 hours. The mixture was concentrated to one-half volume and 20 ml of water was added. The solids were filtered to give 1.3 g of the 7-bromoacetyl-1-ethyl-6,8-difluoro-1,4-dihydro-4-oxo-3-quinolinecarboxylic acid, mp 213°–215° C.

In similar fashion the 7-(bromoacetyl)-6,8-difluoro-1-(2-fluoroethyl)-1,4-dihydro-4-oxo-3-quinolinecarboxylic acid, mp 173°–175° C., and the 10-(bromoacetyl)-9-fluoro-2,3-dihydro-3-methyl-7-oxo-7H-pyrido[1,2,3-de]-1,4-benzoxazine-6-carboxylic acid, mp 224°–225° C., were prepared

EXAMPLE J 7-acetyl-6,8-difluoro-1-(2-fluoroethyl)-1,4-dihydro-4-oxo-3-quinolinecarboxylic acid To 1.62 g (34.0 mmol) of sodium hydride (50% dispersion in oil, pentane washed) in 250 ml of dimethylformamide was added 10.0 g (34 mmol) of the ethyl 7-acetyl-6,8-difluoro-1,4-dihydro-4-oxo-3-quinolinecarboxylate dissolved in 100 ml of dimethylformamide at room temperature. The mixture was stirred for two hours, and 13.0 g (2.4 eq) of 1-bromo-2-fluoroethane was added. The mixture was stirred overnight at 50° C. It was concentrated, and partitioned between water and dichloromethane. The dichloromethane was then concentrated and the residue purified by column chromatography to give 3.75 g of ethyl 7-acetyl-6,8-difluoro-1-(2-fluoroethyl)-1,4-dihydro-4-oxo-3quinoline carboxylate, mp 155°–156° C. This material was hydrolyzed with 2 N hydrochloric acid and 2-propanol as co-solvent to give 2.95 g of the 7-acetyl-6,8-difluoro-1-(2-fluoroethyl)-1,4-dihydro-4-oxo-3-quinoline carboxylic acid, mp 215°–216° C.

EXAMPLE K 6,7,8-Trifluoro-1-(2-fluoroethyl)-1,4-dihydro-4-oxo-3-quinolinecarboxylic acid In identical fashion, 6,7,8-trifluoro-1,4-dihydro-4-oxo-3-quinoline carboxylic acid ethyl ester was converted to 6,7,8-trifluoro-1-(2-fluoroethyl)-1,4-dihydro-4-oxo-3-quinoline carboxylic acid, mp 207°–211° C.

EXAMPLE L

10-Acetyl-9-fluoro-2,3-dihydro-3-methyl-7-oxo-7H-pyrido[1,2,3-de]-1,4-benzoxazine-6-carboxylic acid 1-[6-fluoro-2-[2-(2-methyl-1,3-dioxalan-2-yl)-propoxy]-3-nitrophenyl]ethanone To 35.45 g (0.230 mole) of 2-hydroxymethyl-2-methyl-1,3-dioxolane 0.78 H₂O in 300 ml tetrahydrofuran at −78° C., was added 100 ml of 2.3 M n-butyl lithium. The solution was warmed to −40° C. and added to 46.35 g (0.230 mole) of 2,6-difluoro-3-nitroacetophenone in 200 ml tetrahydrofuran at 0° C. The reaction was stirred 30 minutes then poured into 1000 ml of aan ethyl acetate saturated ammonium chloride solution (1:1). The solution was filtered through celite. The layers separated, and the aqueous layer extracted 3×500 ml of ethyl acetate. The combined organic extracts were washed with brine, dried over magnesium sulfate and the solvent removed at reduced pressure. The product was chromatographed on silica, using hexane:ether (4:1) to give 41.2 g of 1-[6-fluoro-2-[2-methyl-1,3-dioxalan-2-yl)-propoxy]-3-nitrophenyl]ethanone.

1-(2-acetyl-3-ethanone-1-(2-acetyl-3-fluoro-6-nitrophenoxy)-2-propanone 2.2 g (7.35 mmole) of 1-[6-fluoro-2-[2-(2-methyl-1,3-dioxalan-2-yl)propoxy]-3-nitrophenyl]ethanone and 360 ml of water:hydrochloric acid:acetic acid (100:10:250) were stirred overnight. The solvents were removed at reduced pressure, the residue taken up in dichlormethane and washed repeatedly with water. The organic layer was dried over magnesium sulfate and the solvent removed at reduced pressure. The residue was titurated in pentane:Et₂O (3:1) to yield 1.78 g of 1-(2-acetyl-3-fluoro-6-nitrophenoxy)-2-propanone, mp 64°–65° C.

1-(7-Fluoro-2,3-dihydro-3-methyl-2H-1,4-benzoxazine-8-yl)ethanone

A mixture of 4.98 g (19.5 mmole) of 1-(2-acetyl-3-fluoro-6-nitrophenoxy)-2-propanone, 100 ml of 95% ethanol and 1 g of Raney nickel was shaken in an atmosphere of hydrogen at 4.5×10⁵ Pa at room temperature for 18 hours. The reaction was filtered and the solvent removed at reduced pressure. The residue was chromatographed on silica, with hexane:ether (1:1) to give 2.76 g of 1-(7-fluoro-3,4-dihydro-3-methyl-2H-1,4-benzoxazin-8-yl)ethanone.

4-[(8-Acetyl-7-fluoro-2,3-dihydro-2-methyl-4H-1,4-benzoxazin-4-yl)methylene]-2,2-dimethyl-1,3-dioxane-4,6-dione A mixture of 3.66 g (17.49 mmole) of 1-(7-fluoro-3,4-dihydro-3-methyl-2H-1,4-benzoxazine-8-yl)ethanone, 100 ml of methanol and 3.91 g (21.0 mmole) of 4-(methoxymethylene)-2,2-dimethyl-1,3-dioxane-4,6-dione was stirred at room temperature overnight. The reaction was filtered and the solvent removed at reduced pressure. The crystals were titurated with pentane to yield 4.30 g of 4-[(8-acetyl-7-fluoro-2,3-dihydro-3-methyl-4H-1,4-benzoxazine-4-yl)methylene]-2,2-dimethyl-1,3-dioxane-4,6-dione, mp 184°–185° C.

10-Acetyl-9-fluoro-2,3-dihydro-3-methyl-7-oxo-7H-pyrido[1,2,3-de]-1,4-benzoxazine-6-carboxylic acid A mixture of 7.22 g (19.87 mmole) of 4[(8-acetyl-7-fluoro-2,3-dihydro-3-methyl-2H-1,4-benzoxazin-4-yl)-methylene-2,2-dimethyl-1,3-dioxane-4,6-dione and 72.2 g of polyphosphoric acid was heated at 65° C. for two hours. The reaction mixture was cooled and poured onto ice, the crystals were filtered and titurated with ethyl ether to give 3.45 g of 10-acetyl-9-fluoro-2,3-dihydro-3-methyl-7-oxo-7H-pyrido (1,2,3-de)-1,4-benzoxazine-6-carboxylic acid, mp 258°–259° C.

EXAMPLE M

N-methyl-3-pyrrolidinemethanamine

N-methyl-5-oxo-1-(phenylmethyl)-3-pyrrolidinecarboxamide

A mixture of 100 g (0.43 mole) of methyl 5-oxo-1-(phenylmethyl)-pyrrolidinecarboxylate [J. Org. Chem., 26, 1519 (1961)], 500 ml methanol and 100 g (3.2 mole) of methylamine was heated at 100° C. in a pressure reactor for 16 hours. The reaction mixture was cooled and the ammonia and methanol were removed under reduced pressure. The residue was taken up in dichloromethane and washed 3×100 ml 1N sodium hydroxide. The organic layer was dried over magnesium sulfate and the solvent removed at reduced pressure to give 88.3 g of N-methyl-5-oxo-1-(phenylmethyl)-3-pyrrolidinecarboxamide as a white solid, mp 82.5°-83.0° C.

Analysis calculated for $C_{13}H_{16}N_2O_2$: C, 67.22; H, 6.94; N, 12.06. Found: C, 66.98; H, 6.69; N, 12.02.

This material was used in the next step.

N-methyl-1-(phenylmethyl)-3-pyrrolidinemethanamine

To a suspension of 37.40 g (1.00 mole) lithium aluminum hydride in 1000 ml tetrahydrofuran, is added a solution of 88.3 g (0.380 mole) of N-methyl-5-oxo-1-(phenylmethyl)-3-pyrrolidinecarboxamide in tetrafuran dropwise under nitrogen. The reaction was then refluxed overnight. The reaction flask was cooled in an ice bath and 37.4 ml of water, 37.4 ml of 15% sodium hydroxide and and 112.2 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 68.68 g of N-methyl-1-(phenylmethyl)-3-pyrrolidinemethanamine as an oil. This material was used without further purification in the step.

N-methyl-3-pyrrolidinemethanamine

A mixture of 67.28 g (0.32 mole) of N-methyl-1-(phenylmethyl)-3-pyrrolidinemethanamine, 3 g of 20% palladium on carbon, and 600 ml of methanol was shaken in an atmosphere of hydrogen at about $4.5 \times 10^5$ Pa and at room temperature for 18 hours. Another 3 g of 20% palladium on carbon was added and the hydrogenation continued for 6.5 hours. Another 3.0 g of 20% palladium on charcoal was added and the hydrogenation continued for another 4.5 hours. The catalyst was filtered and the filtrate evaporated under reduced pressure. The residue was distilled under vacuum (72°-76° C., 10.5 mm Hg) to give 8.32 g N-methyl-3-pyrrolidinemethanamine.

EXAMPLE N

N-Ethyl-3-pyrrolidinemethanamine

N-Ethyl-5-oxo-1-(phenylmethyl)-3-pyrrolidinecarboxamide

A mixture of 200 g (0.86 mole) of methyl 5-oxo-1-(phenylmethyl)-pyrrolidinecarboxylate [J. Org. Chem., 26, 1519 (1961)], 1000 ml methanol and 200 g (4.4 mole) of ethylamine was heated at 100° C. in a pressure reactor for 17.2 hours. The reaction mixture was cooled and the excess ethylamine and methanol were removed under reduced pressure. The residue was taken up in dichloromethane and washed 3×150 ml 1N sodium hydroxide. The organic layer was dried over magnesium sulfate and the solvent removed at reduced pressure to give 104.6 g of N-ethyl-5-oxo-1-(phenylmethyl)-3-pyrrolidinecarboxamide as a white solid, mp 97°-99° C.

This material was used in the next step.

N-ethyl-1-(phenylmethyl)-3-pyrrolidinemethanamine

To a suspension of 108.68 g (2.860 mole) lithium aluminum hydride in 800 ml tetrahydrofuran, is added a solution of 194.5 g (0.790 mole) of N-ethyl-5-oxo-1-(phenylmethyl)-3-pyrrolidinecarboxamide in 600 ml tetrahydrofuran dropwise under nitrogen. The reaction was then refluxed four hours. The reaction flask was cooled in an ice bath and 108 ml of water, 108 ml of 15% sodium hydroxide, and 324 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 151.9 g of N-ethyl-1-(phenylmethyl)-3-pyrrolidinemethanamine as an oil.

This material was used without further purification in the next step.

N-ethyl-3-pyrrolidinemethanamine

A mixture of 151.65 g (0.695 mole) of N-ethyl-1-(phenylmethyl)-3-pyrrolidinemethanamine, 5 g of 20% palladium on carbon, and 1100 ml of ethanol was shaken in an atmosphere of hydrogen at about $4.5 \times 10^5$ Pa and at room temperature for 21.6 hours. Another 5 g of 20% palladium on carbon was added and the hydrogenation continued for 24 hours. The catalyst was filtered and the filtrate evaporated under reduced pressure. The residue was distilled under vacuum (88°-91° C., 11.5 mm Hg) to give 66.0 g N-ethyl-3-pyrrolidinemethanamine.

EXAMPLE O

N-(2,2,2-Trifluoroethyl)-3-pyrrolidinemethanamine

5-Oxo-1-(phenylmethyl)-N-(2,2,2-trifluoroethyl)-3-pyrrolidine carboxamide

A mixture of 21.9 g (0.100 mole) methyl-5-oxo-1-(phenylmethyl)-3-pyrrodlidinecarboxylate in 150 ml tetrahydrofuran, was cooled to 0° C. in an ice bath under nitrogen and 24.32 g (0.150 mole) carbonyl diimidazole was added. The reaction was stirred at 0° C. for 30 minutes, then at room temperature for 30 minutes. A solution of 13.55 g (0.100 mole) of 2,2,2-triflouroethylamine hydrochloride, 15.22 g (0.100 mole) 1,8-diazabicyclo[5.4.0]undec-7-ene and 100 ml tetrahydrofuran was added. The reaction was stirred at room temperature overnight. The solvent was removed at reduced pressure. The residue was taken up in dichloromethane and washed 3×150 ml saturated sodium bicarbonate. The organic layer was dried over magnesium sulfate and the solvent removed under reduced pressure. The product was purified by column chromatography on silica with ethyl acetate to give 8.50 g of 5-oxo-1-(phenylmethyl)-N-(2,2,2-trifluoroethyl)-3-pyrrolidinecarboxamide mp 110°-112° C.

This material was used in the next step.

1-(Phenylmethyl)-N-(2,2,2-trifluoroethyl)-3-pyrrolidinemethanamine

A mixture of 8.50 g (28.3 mole) of 5-oxo-1-(phenylmethyl)-N-(2,2,2-trifluoroethyl)-3-pyrrolidinemethanamine in 100 ml tetrahydrofuran was added dropwise to 3.22 g (84.9 mmole) of lithium aluminum hydride in 50 ml tetrahydrofuran. The reaction was refluxed two hours, then stirred at room temperature overnight. The reaction was cooled in an ice bath and 3.2 ml of water, 3.2 ml of 15% sodium hydroxide, and 9.6 ml of water were added. The precipitated salts were filtered and washed with hot ethanol. The combined filtrates were concentrated under reduced pressure. The residue was taken up in dichloromethane, filtered, and dried over magnesium sulfate. The solvent was removed at reduced pressure to give 7.15 g of 1-(phenylmethyl-N-(2,2,2-trifluoroethyl)-3-pyrrolidinemethanamine.

This material was used without further purification in the next step.

N-(2,2,2-trifluoroethyl)-3-pyrrolidinemethanamine

A mixture of 7.15 g (26.3 mmole) 1-(phenylmethyl)-N-(2,2,2-trifluoromethyl)-3-pyrrolidinemethanamine 100 ml of methanol and 0.7 g of 20% palladium on carbon was shaken in an atmosphere of hydrogen at about $4.5 \times 10^5$ Pa and at room temperature for 24 hours. The catalyst was filtered and the filtrate evaporated under reduced pressure. The residue was distilled under vacuum (63°–65° C., 2.8 mm Hg) to give 2.55 g of N-(2,2,2-trifluoroethyl)-3-pyrrolidinemethanamine.

EXAMPLE P

N-Propyl-3-pyrrolidinemethanamine

5-Oxo-1-(phenylmethyl)-N-propyl-3-pyrrolidinecarboxamide

To a solution of 10.96 g (50 mmole) of 5-oxo-1-(phenylmethyl)-3-pyrrolidinecarboxylic acid in 150 ml of acetonitrile was added 9.73 g (60 mmole) of 1,1'-carbonyldiimidazole. The reaction was heated to 60° C. for one hour, cooled to room temperature and treated with 4.13 g (70 mmole) of n-propylamine. After stirring for two hours, the solvent was removed in vacuo and the residue partitioned between ether and water. The organic layer was washed with water, 1N hydrochloric acid, dried over magnesium sulfate, filtered, and evaporated invacuo to give 12.0 g of 5-oxo-1-(phenylmethyl)-N-propyl-3-pyrrolidinecarboxamide, mp 86°–87° C.

1-(Phenylmethyl)-N-propyl-3-pyrrolidinemethanamine

To a suspension of 8.2 g (0.2 mole) of lithium aluminum hydride in 150 ml of dry tetrahydrofuran was added portionwise, 12.0 g (45.6 mmole) of solid 5-oxo-1-(phenylmethyl)-N-propyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 9.6 g of 1-(phenylmethyl)-N-propyl-3-pyrrolidine methanamine, as a heavy syrup.

This material was used for the next step without further purification.

N-Propyl-3-pyrrolidinemethanamine

A mixture of 14.0 g (60.0 mmole) of 1-(phenylmethyl)-N-propyl-3-pyrrolidinemethanamine, 1.0 g of 20% palladium on carbon and 140 ml of methanol was shaken in an atmosphere of hydrogen at about $4.5 \times 10^5$ Pa and room temperature for 24 hours. The catalyst was removed by filtering through Celite, the filtrate concentrated and distilled in vacuo to give 7.1 g of N-propyl-3-pyrrolidinemethanamine, bp 49°–50° C./0.25 mm.

EXAMPLE Q

N-Cyclopropyl-3-pyrrolidinemethanamine

5-Oxo-1-(phenylmethyl)-N-cyclopropyl-3-pyrrolidinecarboxamide

To a solution of 16.4 g (75 mmole) of 5-oxo-1-(phenylmethyl)-3-pyrrolidinecarboxylic acid in 150 ml of acetonitrile was added 13.8 g (85 mmole) of 1,1'-carbonyldiimidazole. The reaction was heated to 60° C. for one hour, cooled to room temperature and treated with 4.85 g (85 mmole) of cyclopropylamine. The reaction was stirred at room temperature for 18 hours, the solvent removed in vacuo and the residue partitioned between chloroform and water. The organic layer was washed with water, 1 N hydrochloric acid, dried over magnesium sulfate, filtered, and evaporated in vacuo to give 18.3 g of 5-oxo-1-phenylmethyl-N-cyclopropyl-3-pyrrolidinecarboxamide, mp 94°–96° C.

1-(Phenylmethyl)-N-cyclopropyl-3-pyrrolidinemethanamine

To a suspension of 8.2 g (0.20 mole) of lithium aluminum hydride in 150 ml of dry tetrahydrofuran was added portionwise 18.0 g (70.0 mmole) of solid 5-oxo-1-(phenylmethyl)-N-cyclopropyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 16.0 g of 1-(phenylmethyl)-N-cyclopropyl-3-pyrrolidinemethanamine, as a heavy oil. This was used for the next step without further purification.

N-Cyclopropyl-3-pyrrolidinemethanamine

A mixture of 13.6 g (59.0 mmol) of 1-(phenylmethyl)-N-cyclopropyl-3-pyrrolidinemethanamine, 0.5 g of 20% palladium on carbon and 140 ml of methanol was shaken in an atmosphere of hydrogen at about $4.5 \times 10^5$ Pa and room temperature for 24 hours. The catalyst was removed by filtering through Celite, the filtrate concentrated and distilled in vacuo to give 6.3 g of N-cyclopropyl-3-pyrrolidinemethanamine, bp 88°–90°/13 mm.

EXAMPLE R

N-(2-Propyl)-3-pyrrolidinemethanamine

5-Oxo-1-(phenylmethyl)-N-(2-propyl)-3-pyrrolidinecarboxamide

To a solution of 16.4 g (75.0 mmole) of 5-oxo-1-(phenylmethyl)-3-pyrrolidinecarboxylic acid in 150 ml of acetonitrile was added 13.8 g (85.0 mmole) of 1,1'-carbonyldiimidazole. The reaction was heated to 60° C. for one hour, cooled to room temperature and treated with 5.0 g (85 mmole) of isopropylamine. The reaction was stirred at room temperature for 18 hours, the solvent removed in vacuo and the residue partitioned between chloroform and water. The organic layer was washed with water, 1N hydrochloric acid, dried over magnesium sulfate and evaporated in vacuo to give 18.6 g to give 18.6 g of 5-oxo-1-(phenylmethyl)-N-(2-propyl)-3-pyrrolidinecarboxamide, mp 122°–124° C.

1-(Phenylmethyl)-N-(2-propyl)-3-pyrrolidinemethanamine

To a suspension of 8.2 g (0.2 mole) of lithium aluminum hydride in 150 ml of dry tetrahydrofuran was added portionwise, 18.3 g (70.0 mmole) of solid 5-oxo-1-(phenylmethyl)-N-(2-propyl)-3-pyrrolidinecarboxamide. When the addition was compete, the reaction mixture was stirred at room temperature for 18 hours and then refluxed for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 15.6 g of 1-(phenylmethyl)-N-(2-propyl)-3-pyrrolidinemethanamine as a heavy syrup.

This material was used for the next step without further purification.

N-(2-Propyl)-3-pyrrolidinemethanamine

A mixture of 13.4 g (58.0 mmol) of 1-phenylmethyl-N-(2-propyl)-3-pyrrolidinemethanamine, 1.0 g of 20% palladium on carbon and 130 ml of methanol was shaken in an atmosphere of hydrogen at about $4.5 \times 10^5$ Pa and room temperature for 24 hours. The catalyst was removed by filtration through Celite; the filtrate concentrated and distilled in vacuo to give 6.3 g of N-(2-propyl)-3-pyrrolidinemethanamine, bp 58°–60° C./3.5 mm.

EXAMPLE S

2-[(3-pyrrolidinylmethyl)amino]ethanol

N-(2-hydroxyethyl)-5-oxo-1-(phenylmethyl)-3-pyrrolidinecarboxamide

A mixture of 46.7 g (1200 mole) of methyl-5-oxo-1-(phenylmethyl)-3-pyrrolidinecarboxylate (J. Org. Chem., 26, 1519 (1961)], 36.7 g (1600 mole) 2-aminoethanol and 500 ml methanol were refluxed overnight. The reaction was cooled to room temperature and the solvent removed at reduced pressure. The residue was taken up in dichloromethane and extracted $3 \times 100$ ml 1 N sodium hydroxide. The aqueous layer was taken to pH 5, extracted $3 \times 150$ ml dichloromethane, then taken to pH 8 and again extracted $3 \times 150$ ml dichloromethane. The aqueous layer was concentrated at reduced pressure and the resulting slurry stirred in dichloromethane. The salts were filtered off. The combined organic layers were dried over magnesium sulfate, the solvent removed at reduced pressure to yield 47.9 g of N-(2-hydroxyethyl)-5-oxo-1-phenylmethyl)-3-pyrrolidinecarboxamide as an oil. This was used in the next step without further purification.

2-[[[1-(phenylmethyl)-3-pyrrolidinyl]methyl]amino]ethanol

A mixture of 46.66 g (0.178 mole) of N-(2-hydroxyethyl)-5-oxo-2-(phenylmethyl)-3-pyrrolidinecarboxamide in 200 ml of tetrahydrofuran was added dropwise to a slurry of 20.25 g (0.534 mole) of lithium aluminum hydride in 150 ml tetrahydrofuran. The reaction was refluxed three hours, then cooled in an ice bath. The work up consisted of sequential addition of 20 ml water, 20 ml 15% sodium hydroxide then 60 ml water. The reaction was filtered and the precipitate washed with ethanol. The filtrate was concentrated at reduced pressure, the residue taken up in dichloromethane, dried over magnesium sulfate, and the solvent removed at reduced pressure to give 32.31 g of 2-[[[1-(phenylmethyl)-3-pyrrolidinyl]methyl]amine]ethanol as an oil. This material was used in the next step without further purification.

2-[(3-pyrrolidinylmethyl)amino]ethanol

A mixture of 32.32 g of 2-[[[1-(phenylmethyl)-3-pyrrolidinyl]-methyl]amino]ethanol, 330 ml of methanol and 3 g of 20% palladium on charcoal was shaken in an atmosphere of hydrogen at about $4.5 \times 10^5$ Pa and at room temperature for 18 hours. The solvents were then removed at reduced pressure. The residue was distilled under vacuum (bp 129°–131° C., 1.5 mm Hg) to give 11.43 g of 2-[(3-pyrrolidinylmethyl)amino] ethanol.

EXAMPLE T

1,1-Dimethylethyl[1-(diphenylmethyl)-3-azetidinyl]carbamate

A solution of 12.2 g (51.2 mmole) of 1-(diphenylmethyl)-3-azetidinamine in a mixture of 34 ml of water and 100 ml of t-butanol was treated dropwise with 11.4 g (52 mmol) of ditertiarybutyldicarbonate. After the addition was complete, the reaction was heated at 60° C. for 1 hour, then at room temperature for 18 hours. The reaction mixture was diluted with water and extracted with chloroform. The chloroform layer was washed with water, dried over magnesium sulfate, filtered, and evaporated in vacuo to give 14.3 g of 1,1-dimethylethyl-1-(diphenylmethyl)-3-azetidinyl]carbamate, mp 148°–153° C.

EXAMPLE U

1,1-Dimethylethyl(3-azetidinyl)carbamate

A solution of 14.2 g (42.0 mmole) of 1,1-dimethylethyl-[1-(diphenylmethyl)-3-azetidinyl]carbamate in 100 ml of tetrahydrofuran was shaken with 2 g of 20% palladium on carbon in a hydrogen atmosphere at $4.5 \times 10^5$ Pa for 24 hours. The reaction was filtered through Celite and the solvent was removed in vacuo. The residue was triturated several times with hexane to give, as the insoluble residue, 6.5 g of 1,1-dimethylethyl-(3-azetidinyl)carbamate, mp 138°–140° C.

EXAMPLE V

1-(Diphenylmethyl)-3-azetidinemethanamine

A suspension of 5.7 g (0.15 mole) of lithium aluminum hydride in 200 ml of dry tetrahydrofuran was treated portionwise with 18.6 g (75 mmole) of solid 3-cyano-1-(diphenylmethyl)azetidine. When the addition was complete, the reaction was stirred at room temperature for two hours, refluxed for four hours, and stirred at room temperature for 18 hours. The reaction was decomposed by the successive addition of 6 ml of water, 6 ml of 15% sodium hydroxide, and 18 ml of water, titrating the final water addition to give a granular precipitate. The inorganic precipitate was removed by filtration, washed with tetra hydrofuran and evaporated in vacuo to give 16.9 g of 1-(diphenylmethyl)-3-azetidinemethanamine as a heavy oil.

EXAMPLE X

1,1-Dimethylethyl[[1-(diphenylmethyl)-3-azetidinyl]methyl]carbamate

To a solution of 12.0 g (47 mmole) of 1-(diphenylmethyl)-3-azetidinemethanamine, 2.08 g (52 mmole) of sodium hydroxide in 34 ml of water and 100 ml of t-butanol was added dropwise 11.4 g (52 mmole) of ditertiarybutyl-dicarbonate. The reaction was heated at 60° C. for one hour, then at room temperature for 18 hours. The reaction was then diluted with water and extracted with chloroform. The organic layer was washed with water, dried over magnesium sulfate, filtered and evaporated in vacuo to give 14.2 g of 1,1-dimethylethyl[[1-(diphenylmethyl)3-azetidinyl]methyl]carbamate.

EXAMPLE Y 1,1-Dimethyl(3-azetidinylmethyl)carbamate

A solution of 13.7 g (38.9 mmole) of 1,1-dimethylethyl[[1-diphenylmethyl)-3-azetidinyl]methyl]carbamate in 150 ml of tetrahydrofuran was shaken with 2g of 20% palladium on carbon in a hydrogen atmosphere 4.5×10⁵ Pa for 24 hours. The reaction was filtered through Celite and the solvent removed in vacuo. The residue was triturated several times with hexane to give, as an insoluble residue, 6.8 g of 1,1-dimethyl(3-azetidinylmethyl)carbamate as a viscous oil. This was used without further purification.

EXAMPLE Z 1-(Diphenylmethyl)-N-methyl-3-azetidinecarboxamide

To a solution of 7.5 g (28 mmole) of 1-(diphenylmethyl)azetidine-3-carboxylic acid in 75 ml of acetonitrile was added 6.0 g (37 mmole) of 1,1'-carbonyldiimidazole. The reaction was heated at 60° C. for two hours and successively treated with 3.11 g (30.8 mmole) of triethylamine and 2.08 g (30.8 mmole) of methylamine hydrochloride. The reaction was stirred at 60° C. for an additional hour, the solvent evaporated in vacuo, and the residue dissolved in chloroform. After washing with water and drying over magnesium sulfate, the chloroform layer was evaporated in vacuo to give 9.0 g of 1-(diphenylmethyl)-N-methyl-3-azetidinecarboxamide, mp 103-107° C.

EXAMPLE AA 1-(Diphenylmethyl)-N-methyl-3-azetidinemethanamine

To a suspension of 3.2 g (85 mmole) of lithium aluminum hydride in 50 ml of dry tetrahydrofuran was added dropwise, a solution of 8.5 g (28 mmole) of 1-diphenylmethyl-N-methyl-3-azetidinecarboxamide in 50 ml of dry tetrahydrofuran. After the addition was complete, the reaction was refluxed for two hours, cooled to room temperature, and decomposed by the successive addition of 3.4 ml of water, 3.4 ml of 15% aqueous sodium hydroxide and 10.2 ml of water, titrating the final water addition to give a granular precipitate. The inorganic precipitate was removed by filtration, washed with tetrahydrofuran, and evaporated in vacuo. The residue was dissolved in chloroform, dried over magnesium sulfate, filtered, and evaporated in vacuo to give 7.0 g of 1-(diphenylmethyl)-N-methyl-3-azetidinemethanamine as a heavy syrup. This was used without further purification.

EXAMPLE BB

N-Methyl-3-azetidininemethanamine

A solution of 6.7 g (25 mmole) of 1-diphenylmethyl-N-methyl-3-azetidinemethanamine in 100 ml of methanol was shaken with 2.0 g of 20% palladium on carbon in a hydrogen atmosphere at 4.5×10⁵ Pa for 18 hours. The reaction was filtered through Celite and the solvent removed in vacuo. The residue was triturated several times with hexane to give, as the insoluble residue, 2.3 g of N-methyl-3-azetidinemethanamine as a heavy syrup. This was used without further purification.

EXAMPLE CC 1-(Diphenylmethyl)-N-ethyl-3-azetidinecarboxamide

To a solution of 7.5 g (28 mmole) of 1-(diphenylmethyl)azetidine-3-carboxylic acid in 75 ml of acetonitrile was added 6.0 g (37 mmole) of 1,1'-carbonyldiimidazole. The reaction was heated at 60° C. for two hours and successively treated with 3.1 g (30.8 mmole) of triethylamine and 2.52 g (30.8 mmole) of ethylamine hydrochloride. The reaction was stirred at 60° C. for an additional hour, the solvent evaporated in vacuo and the residue dissolved in chloroform. After washing with water and drying over magnesium sulfate, the chloroform layer was evaporated in vacuo to give 9.4 g of 1-(diphenylmethyl)-N-ethyl-3-azetidinecarboxamide, mp 91°–93° C.

EXAMPLE DD 1-(Diphenylmethyl)-N-ethyl-3-azetidinemethanamine

To a suspension of 3.2 g (85 mmole) of lithium aluminum hydride in 50 ml of dry tetrahydrofuran was added dropwise, a solution of 8.5 g (28.0 mmole) of 1-(diphenylmethyl)-N-ethyl-3-azetidinecarboxamide in 50 ml of dry tetrahydrofuran. After the addition was complete, the reaction was refluxed for two hours, cooled to room temperature, and decomposed by the successive addition of 3.4 ml of water, 3.4 ml of 15% aqueous sodium hydroxide and 10.2 ml of water, titrating the final water addition to give a granular precipitate. The inorganic precipitate was removed by filtration, washed with tetrahydrofuran and evaporated in vacuo to give 6.7 g of 1-(diphenylmethyl)-N-ethyl-3-azetidinemethanamine as a heavy syrup. This was used without further purification.

EXAMPLE EE

N-Ethyl-3-azetidinemethanamine

A solution of 6.4 g (23 mmole) of 1-(diphenylmethyl)-N-ethyl-3-azetidinemethanamine in 00 ml of methanol was shaken with 2.0 g of 20% palladium on carbon in a hydrogen atmosphere at 4.5×10⁵ Pa for 18 hours. The reaction was filtered through Celite and the solvent removed in vacuo. The residue was triturated several times with hexane to give, as the insoluble residue, 1.6 g of N-ethyl-3-azetidinemethanamine as a heavy syrup. This was used without further purification.

EXAMPLE FF

2-Methyl-2,7-diazaspiro[4.4]nonane-1,3,8-trione

A solution of 20.3 g (0.084 mole) 3-ethoxycarbonyl-5-oxo-3-pyrrolidineacetic acid ethyl ester [J. Org. Chem. 46, 2757 (1981)]in 40 ml of 40% aqueous methylamine was stirred at room temperature overnight, then placed in an oil bath and gradually heated to 220° C. over 30 minutes allowing volatiles to distill from the open flask. The crude product was crystallized from ethanol to afford 12.56 g of the title compound, mp 201°–204° C. Analysis calculated for $C_8H_{10}N_2O_3$: C, 52.74; H, 5.53; N, 15.38. Found: C, 52.87; H, 5.60; N, 15.25.

EXAMPLE GG

7-Benzyl-2-methyl-2,7-diazaspiro[4.4]nonane-1,3,8-trione

A solution of 1.82 g (10 mmol) 2-methyl-2,7-diazaspiro[4.4]nonane-1,3,8-trione in 20 ml N,N-dimethylformamide was added gradually under a nitrogen atmosphere to 0.050 g (10.4 mmol) of 50% oil suspension of sodium hydride which had been previously washed twice with toluene and covered with 10 ml N,N-dimethylformamide. After stirring one hour there was added 1.40 g (11 mmol) of benzyl chloride and stirring was continued overnight at room temperature. After concentrating to a small volume in vacuo, the residue was diluted with 40 ml water and extracted twice with dichloromethane. The combined organic phase was washed with water, dried over magnesium sulfate, and evaporated to give a solid. Crystallization from toluene:hexane to affore 1.74 g of the title compound, mp 157°–158° C.

Analysis calculated for $C_{15}H_{16}N_2O_3$: C, 66.16; H, 5.92; N, 10.27. Found: C, 66.45; H, 5.79; N, 10.09.

EXAMPLE HH

2-Benzyl-7-methyl-2,7-diazaspiro[4.4]nonane Dihydrohloride

A solution of 1.36 g (5.0 mmol) 7-benzyl-2-methyl-2,7-diazaspiro[4.4]nonane-1,3,8-trione in 50 ml tetrahydrofuran was added dropwise to a suspension of 0.95 g (25 mmol) lithium aluminum hydride in 30 ml tetrahydrofuran. The mixture was stirred overnight at room temperature, refluxed one hour, cooled, and treated dropwise with 0.95 ml water, 0.95 ml 15% sodium hydroxide solution and 2.8 ml water. After removal of the inorganic solids by filtration, the filtrate was concentrated in vacuo to give a syrup which was dissolved in isopropanol and treated with excess 6N hydrogen chloride in isopropanol. Crystallization afforded 0.97 g of the title compound, mp 233°–234° C.

Analysis calculated for $C_{15}H_{24}N_2Cl_2$: C, 59.40; H, 7.98; N, 9.24; Cl, 23.38. Found: C, 59.37; H, 7.98; N, 9.03; Cl, 23.09.

EXAMPLE II

2-Methyl-2,7-diazaspiro[4.4]nonane Dihydrochloride

A solution of 7-benzyl-2-methyl-2,7-diazaspiro[4.4]nonane dihydrochloride in 150 ml of methanol with 1.0 g 20% palladium on carbon catalyst was hydrogenated at $4.5 \times 10^5$ Pa for two days. After filtration, the filtrate was concentrated to a thick syrup which crystallized on addition of acetonitrile to give 11.50 g of the title compound, softened at 164° C. and melted at 168°–170° C. Analysis calculated for $C_8H_{18}N_2Cl_2$: C, 45.08; H, 8.51; N, 13.15; Cl, 33.27; Found: C, 45.24; H, 8.77; N, 13.18; Cl, 33.26.

EXAMPLE JJ

2-Ethyl-2,7-diazaspiro[4.4]nonane-1,3,8-trione

A suspension of 24.33 g (0.100 mmole) 3-ethoxycarbonyl-5-oxo-3-pyrrolidineacetic acid ethyl ester in an excess of 2 N sodium hydroxide, was stirred three hours at room temperature, acidified with dilute hydrochloric acid, and evaporated to dryness in vacuo. The product, 3-carboxy-5-oxo-3-pyrrolidineacetic acid, was taken up in isopropyl alcohol, separated from insoluble sodium chloride by filtration, concentrated to a syrup and dissolved in 100 ml 70% ethylamine. The solution was gradually heated in an oil bath up to 230°–° C. allowing volates to distill and then maintained at 230-240° C. for ten minutes. After cooling, the product was crystallized from isopropyl alcohol to afford 10.12 g of the title compound, mp 168°–169° C.

Analysis calculated for $C_9H_{12}N_2O_3$: C, 55.09; H, 6.17; N, 14.28; Found: C, 55.03; H, 5.84; N, 14.01.

EXAMPLE KK

2-Ethyl-7-benzyl-2-7-diazaspiro[4.4]nonane-1,3,8-trione

A suspension of sodium hydride (2.20 g of 60% oil suspension (0.055 mole) washed with toluene) in 50 ml N,N-dimethylformamide was treated gradually with a solution of 10.0 g (0.051 mole) 2-ethyl-2,7-diazaspiro[4.4]nonane-1,3,8-trione in 100 ml N,N-dimethylformamide. After stirring 15 minutes, there was added dropwise 6.4 ml (0.055 mole) benzyl chloride and the mixture was stirred overnight, concentrated in vacuo and shaken with water-methylene chloride. The organic layer was dried, evaporated, and the product crystallized from toluene-hexane to afford 11.11 g of the title compound, mp 125°–126.5° C.

Analysis calculated for $C_{16}H_{18}N_2O_3$: C, 67.11; H, 6.34; N, 9.79. Found: C, 67.41; H, 6.33; N, 9.79.

EXAMPLE LL

2-Benzyl-7-ethyl-2,7-diazaspiro[4.4]nonane Dihydrochloride

A solution of 11.00 g (0.0385 mole) 2-ethyl-7-benzyl-2,7-diazaspiro[4.4]nonane-1,3,8-trione in 100 ml tetrahydrofuran was added dropwise to a suspension of 6.00 g (0.158 mole) lithium aluminium hydride in 250 ml tetrahydrofuran. After stirring overnight, the mixture was refluxed one hour, cooled, and treated dropwise with 6 ml water, 6 ml 15% sodium hydroxide, and 18 ml water. Inorganic solids were separated by filtration and the filtrate was concentrated, taken up in ether, dried with magnesium sulfate, and reevaporated. The resulting syrup was dissolved in isopropyl alcohol and treated with excess hydrogen chloride in isopropyl alcohol to afford 9.63 g of the title compound, mp 196°–198° C. (dec).

Analysis calculated for $C_{16}H_{26}N_2Cl_2$: C, 60.56; H, 8.26; N, 8.83; Cl, 22.35. Found: C, 60.51; H, 8.08; N, 8.69; Cl, 22.26.

EXAMPLE MM

2-Ethyl-2,7-diazaspiro[4.4]nonane Dihydrochloride

A solution of 9.50 g (0.030 mole) 2-benzyl-7-ethyl-2,7-diazaspiro[4.4]nonane dihydrochloride in 100 ml methanol was hydrogenated with 1.0 g 20% palladium on carbon catalyst at $4.5 \times 10^5$ Pa for 22 hours. After filtration, the solution was concentrated to a syrup and crystallized from acetonitrile to afford 6.66 g of the title compound, mp 168°–172° C.

Analysis calculated for $C_9H_{20}N_2Cl_2$: C, 47.58; H, 8.86; N, 12.33; Cl, 31.21. Found: C, 47.70; H, 8.58; N, 12.39; Cl, 30.92.

EXAMPLE NN

1-Cyclopropyl-6,7,8-trifluoro-1,4-dihydro-4-oxo-3-quinolinecarboxylic Acid 2,3,4,5-Tetrafluoro-β-oxo-benzenepropanoic Acid, Ethyl Ester To 30.0 g (155 mmol) of 2,3,4,5-tetrafluorobenzoic acid in 75 ml of dichloromethane was added 14.8 ml (1.1 equivalents) of oxalyl chloride. The mixture was then treated with three drops of dry N,N-dimethylformamide and the vigorous reaction was stirred at room temperature overnight. The mixture was then concentrated to an oil, taken up in toluene, and reconcentrated to afford 2,3,4,5-tetrafluorobenzoyl chloride which was used in the next step.

To 40.92 g (310 mmol) of malonic acid half ethyl ester in 700 ml of dry tetrahydrofuran at −35° C. was added a stream of n-butyllithium until one equivalent was delivered. The mixture was maintained at −15 to −30° during the addition, then warmed to −5° C. treated with 10 mg of bipyridyl. The remainder of the n-butyllithium was added at this temperature until the indicator turned pink. A total of 282 ml of 2.2 N n-butyllithium was added. The mixture was recooled to -78° C. and a solution of 2,3,4,5-tetrafluorobenzoyl chloride in 100 ml of dry tetrahydrofuran was added keeping the temperature constant. The reaction mixture was stirred for 45 minutes after the acid chloride addition. It was warmed to −35° C. and poured into 155 ml of 2 N hydrochloric acid. To this mixture was added one liter of water and 1.5 liters of dichloromethane. The aqueous phase was separated and extracted with an additional 1.5 liters of dichloromethane. The combined organic phases were washed with sodium bicarbonate and then 1 N hydrochloric acid. The dichloromethane was dried (magnesium sulfate) and concentrated to a solid which was triturated with cold pentane to give 37.8 g of 2,3,4,5-tetrafluoro$\beta$-oxo-benzenepropanoic acid, ethyl ester, mp 63°–65° C.

1-Cyclopropyl-6,7,8-trifluoro-1,4-dihydro-4-oxo-3-quinolinecarboxylic Acid

To 17.6 g (66.6 mmol) of the 2,3,4,5-tetrafluoro$\beta$-oxo-benzenepropanoic acid was added 14.6 g (~1.5 equivalents) of triethylorthoformate and 16.19 g (2.38 equivalents) of acetic anhydride. The mixture was refluxed for two hours at 120° (and was then cooled to 80° C. and concentrated in vacuo. The mixture was diluted with t-butanol, cooled to 10° C., and 3.8 g (1.05 equivalents) of cyclopropylamine in 120 ml of t-butanol was added. The mixture was stirred at 20° C. for 30 minutes and then warmed to 50° C. overnight. At this temperature 7.5 g of potassium t-butoxide was added in 50 ml of t-butanol and the mixture was stirred for four hours. It was filtered and the solids dissolved in 250 ml of hot acetic acid 200 ml of 3N hydrochloric acid was added in portions over four hours at 100° C. The mixture was cooled and the solids collected to give 15.44 g (82%) of the 1-cyclopropyl-6,7,8-trifluoro-1,4-dihydro-4-oxo-3-quinolinecarboxylic acid, mp 226°–228° C.

EXAMPLE OO 1,1-Dimethylethyl (3-Pyrrolidinyl)carbamate 1,1-Dimethylethyl [1-(Phenylmethyl)-3-pyrrolidinyl]-carbamate A solution of 77.0 g (0.44 mole) of 3-amino-1-(phenylmethyl)pyrrolidine [J. Med. Chem., 24, 1229 (1981)], 440 ml (0.44 mole) 1.0 N sodium hydroxide and 600 ml of tertiary butyl alcohol was treated dropwise with 98.2 g (0.45 mole) of di-tertiarybutyl dicarbomate. The reaction was stirred at room temperature for 18 hours and the solvent removed in vacuo. The residue was partitioned between ether and water. The aqueous layer was reextracted with ether, the combined ether layers were washed with water, dried (MgSO₄), filtered and evaporated on a steam bath replacing the ether with petroleum ether. The crystals which formed were removed by filtration, washed with ether/petroleum ether (1:1), and dried in vacuo to give 84.8 g of 1,1-dimethylethyl [1-(phenylmethyl)-3-pyrrolidinyl]carbamate, mp 114°–115° . A second crop (16.7 g) was obtained by concentrating the filtrate.

1,1-Dimethylethyl (3-Pyrrolidinyl)carbamate

A mixture of 27.6 g (0.1 mole) of 1,1-dimethylethyl[1-(phenylmethyl)-3-pyrrolidinyl]carbamate, 1.0 g of 20% Palladium on carbon and 140 ml of methanol was shaken in an atmosphere of hydrogen at about 50 psi and room temperature for 24 hours. The catalyst was removed by filtering through Celite, and the filtrate was concentrated in vacuo to give 18.4 g of 1,1-dimethylethyl (3-pyrrolidinyl)carbamate which solidified upon standing.

EXAMPLE PP

4-[6-(Cyclopropylamino)-3-nitro-2-pyridinyl]-1-piperazinecarboxylic acid, ethyl ester A solution of 126.0 g (0.4 mole) of 4-(6-chloro-3-nitro-2-pyridinyl)-1-piperazinecarboxylic acid, ethyl ester (prepared as described in European Patent Publication No. 9425), 76.1 g (0.5 mole) of 1,8-diazabicyclo[5.4.0]undec-7-ene (DBU), 28.6 g (0.5 mole) of cyclopropylamine and 500 ml of absolute ethanol was stirred at room temperature for 48 hours. The solution was then heated at reflux for four hours and concentrated in vacuo. The residue was partitioned between chloroform and water. The chloroform layer was dried over magnesium sulfate and concentrated in vacuo. The residue was triturated with ether to give 64.0 g of the title compound, mp 100°–103° C.

4-[6-(Acetylcyclopropylamino)-3-nitro-2-pyridinyl]-1-piperazinecarboxylic acid, ethyl ester A solution of 64.0 g (0.19 mole) of 4-[6-(cyclopropylamino)-3-nitro-2-pyridinyl]-1-piperazinecarboxylic acid, ethyl ester, 115 ml of acetic anhydride and 115 ml of acetic acid was heated on a steam bath for 36 hours. The solvents were removed in vacuo, the residue was triturated with a mixture of ethanol and toluene which was also evaporated in vacuo to give 68.3 g of the title compound, mp 90°–93° C.

4-[6-(Acetylcyclopropylamino)-3-amino-2-pyridinyl]-1-piperazinecarboxylic acid, ethyl ester A mixture of 17.0 g (45 mmole) of 4-[6-(acetylcyclopropylamino)-3-nitro-2-pyridinyl-1-piperazinecarboxylic acid, ethyl ester, 1.5 g of Raney nickel and 180 ml of absolute ethanol was shaken in a atmosphere of hydrogen at about 50 psi and room temperature for approximately 24 hours. The catalyst was removed by filtering through Celite and the solvent removed in vacuo to give 15.2 g of the title compound, mp 149°–150° C.

2-[4-(Ethoxycarbonyl)-1-piperazinyl]-6-(acetylcyclopropylamino)-3-pyridinediazonium tetrafluoroborate A solution of 20.8 g (60 mmole) of 4-(6-acetylcyclopropylamino)-3-amino-2-pyridinyl]-1-piperazinecarboxylic acid, ethyl ester, 44 ml of ethanol and 27 ml of 48% tetrafluoroboric acid was cooled to 0° C. and treated dropwise with a solution of 4.56 g (66 mmol) of sodium nitrite in 8 ml of water under a nitrogen atmosphere keeping the temperature 0°-5° C. After the addition was complete, the reaction was stirred at 0°-5° C. for one hour and treated with 150 ml of anhydrous ether keeping the temperature below 10° C. The solid was removed by filtration, the precipitate was washed with ethanol/ether (1:1), ether and dried in vacuo to give 24.5 g of the title compound, mp 100°–105° C. (dec.).

4-[6-(Acetylcyclopropylamino)-3-fluoro-2-pyridinyl]1-piperazinecarboxylic acid, ethyl ester To 800 ml of refluxing toluene was added in portions, as a solid, 46.2 g (0.1 mole) of 2-[4-(ethoxycarbonyl)-1- piperazinyl]-6-(acetylcyclopropylamino)-3-pyridinediazonium tetrafluoroborate. After the addition was complete, the reaction was refluxed for ten minutes and the toluene was decanted from the insoluble precipitate. The toluene was evaporated in vacuo and the residue was partitioned between chloroform and water. The chloroform layer was washed with 5% aqueous sodium bicarbonate, water, dried over magnesium sulfate and evaporated in vacuo to give 13.7 g of the title compound, as a viscous oil. An additional 10.2 g could be obtained by partitioning the original toluene insoluble material in chloroform and water. The organic layer was washed with 5% aqueous sodium bicarbonate, dried over magnesium sulfate, evaporated in vacuo and the residue was chromatographed on silica gel eluting with chloroform/ethyl acetate (6:4). This fraction was also a viscous oil which did not crystallize upon standing. Both fractions were of sufficient purity to be used as is in the ensuing steps.

4-[6-(Cyclopropylamino)-3-fluoro-2-pyridinyl]-1-piperazinecarboxylic acid, ethyl ester A solution of 21.9 g (63 mmole) of 4-[6-(acetyl-cyclopropylamino)-3-fluoro-2-pyridinyl]-1-piperazinecarboxylic acid, ethyl ester, 170 ml of 15% hydrochloric acid and 235 ml of methanol was refluxed for one hour and allowed to stir at room temperature for 18 hours. The methanol was removed in vacuo and the aqueous acid was made basic with 1.0 N sodium hydroxide to pH 10.5. The mixture was extracted with chloroform, the chloroform layer washed with water, dried over magnesium sulfate, and evaporated in vacuo to give 17.6 g of the title compound, mp 68°–70° C.

1-Cyclopropyl-6-fluoro-1,4-dihydro-4-oxo-7-(1-piperazinyl)-1,8-naphthyridine-3-carboxylic acid Route A 1-[Cyclopropyl[6-[4-(ethoxycarbonyl)-1-piperazinyl]5-fluoro-2-pyridinyl]amino]methylene]propanedioic acid, diethyl ester A solution of 3.8 g (12.3 mmole) of 4-[6-(cyclopropylamino)-3-fluoro-2-pyridinyl]-1-piperazinecarboxylic acid, ethyl ester, 2.7 g (12.3 mmole) of diethyl (ethoxymethylene)malonate and 50 ml of xylene was refluxed for 24 hours. The solvent was removed in vacuo and the residue was chromatographed over silica gel eluting with chloroform/ethyl acetate (80/20) to give 2.3 g of the title compound as a viscous oil which was used without further purification.

Ethyl 1-Cyclopropyl-6-fluoro-1,4-dihydro-4-oxo-7-[4-(ethoxycarbonyl)-1-piperazinyl]-1,8-naphthyridine-3-carboxylate A solution of 2.3 g (4.8 mmole) of [[cyclopropyl[6-[4-(ethoxycarbonyl)-1-piperazinyl]-5-fluoro-2-pyridinyl]amino]methylene]propanedioic acid, diethyl ester, in 15 ml of acetic anhydride was treated dropwise with 5 ml of 98% sulfuric acid keeping the temperature 55°–60° C. When the addition was complete, the reaction was stirred for one hour and poured onto 50 g of ice. The aqueous suspension was extracted with chloroform, the chloroform layer washed with water, dried over magnesium sulfate, filtered, and evaporated in vacuo. The residue was triturated with several portions of ethanol/toluene which were also removed in vacuo to give 0.4 g of the title compound, mp 184°–186° C. An additional 0.5 g of product could be obtained by concentrating the original aqueous fraction, mp 184°–186° C.

1-Cyclopropyl-6-fluoro-1,4-dihydro-4-oxo-7-(1-piperazinyl)-1,8-naphthyridine-3-carboxylic acid A suspension of 0.7 g (1.6 mmole) of ethyl 1-cyclopropyl-6-fluoro-1,4-dihydro-4-oxo-7-[4-(ethoxycarbonyl)-1-piperazinyl]-1,8-naphthyridine-3-carboxylate, 6 ml of 10% aqueous sodium hydroxide and 2 ml of ethanol was refluxed for three hours. The reaction was filtered through a fiber glass pad to and acidified to pH 1.5 with 6.0 M hydrochloric acid and lyophilized. The residue was dissolved in 10 ml of ammonium hydroxide and the solution concentrated in vacuo. The precipitate which formed was removed by filtration, washed with aqueous ethanol, ether and dried in vacuo to give 0.04 g, mp 274°–276° C.

Route B

4-[6-[Cyclopropyl(2,2-dimethyl-4,6-dioxo-1,3-dioxan-5-ylidine)amino]-3-fluoro-2-pyridinyl]-1-piperazinecarboxylic acid, ethyl ester A solution of 17.6 g (57 mmole) of 4-[6-(cyclopropylamino)-3-fluoro-2-pyridinyl]-1-piperazinecarboxylic acid, ethyl ester, 11.6 g (63 mmole) of 5-(methoxymethylene)-2,2-dimethyl-1,3-dioxane-4,6-dione and 250 ml of methanol was stirred at room temperature for four hours. The solid was removed by filtration, washed with methanol, ether and dried in vacuo to give 7.6 g of the title compound, mp 177°–178° C.

1-Cyclopropyl-6-fluoro-1,4-dihydro-4-oxo-7-[4-(ethoxycarbonyl)-1-piperazinyl]-3-carboxylic acid A solution of 17.0 g (37.0 mmole) of 4-[6-(cyclopropyl(2,2-dimethyl-4,6-dioxo-1,3-dioxan-5-ylidene)amino]-3-fluoro-2-pyridinyl]-1-piperazinecarboxylic acid, ethyl ester in 125 ml of acetic anhydride was treated dropwise with 35 ml of 98% sulfuric acid keeping the temperature 50°–60° C. When the addition was complete, the reaction was stirred for two hours and poured onto 600 g of ice. The mixture was stirred was stirred for one hour and the resulting precipitate was removed by filtration, washed with water and dried in vacuo to give 10.2 g of the title compound, mp 277°–279° C.

1-Cyclopropyl-6-fluoro-1,4-dihydro-4-oxo-7-(1-piperazinyl)-1,8-naphthyridine-3-carboxylic acid A solution of 10.2 g (25 mmole) of 1-cyclopropyl-6-fluoro-1,4-dihydro-4-oxo-7-[4-(ethoxycarbonyl)-1-piperazinyl]-1,8-naphthyridine-3-carboxylic acid, 100 ml of 10% aqueous sodium hydroxide and 40 ml of ethanol was refluxed for three hours. The solution was concentrated to 125 ml and acidified to pH 7.3 with glacial acetic acid. The resulting precipitate was removed by filtration, washed with 50% aqueous ethanol, ether and dried in vacuo to give 7.2 g of the title compound, mp 274°–276°.

1-Cyclopropyl-6-fluoro-1,4-dihydro-7-hydroxy-4-oxo-1,8-naphthyridine-3-carboxylic acid To a solution of 2 ml of 70% nitric acid in 10 ml of 98% sulfuric acid was added in portions 1.0 g (3.0 mmole) of 1-cyclopropyl-6-fluoro-1,4-dihydro-4-oxo-7-(1-piperazinyl)-1,8-naphthyridine-3-carboxylic acid, keeping the temperature between 25°–30° C. The resulting solution was stirred at room temperature for 18 hours and poured onto 40 g of ice. The mixture was stirred at room temperature for 24 hours, concentrated in vacuo, the pH adjusted to 12 with aqueous sodium hydroxide, and filtered through a fiber glass pad. The filtrate was acidified to pH 3.5 with 6.0M hydrochloric acid, the resulting precipitate removed by filtration, washed with water then ether and dried in vacuo to give 0.23 g of the title compound, mp 325°–327° C.

7-Chloro-1-cyclopropyl-6-fluoro-1,4-dihydro-4-oxo-1,8-naphthyridine-3-carboxylic acid A suspension of 0.19 g (0.72 mmole) of 1-cyclopropyl-6-fluoro-1,4-dihydro-7-hydroxy-4-oxo-1,8-naphthyridine-3-carboxylic acid in 2 ml of phosphorus oxychloride was heated at reflux for ½ hour. The resulting solution was cooled to room temperature and the solvent was removed in vacuo. The residue was triturated with ice-water and the resulting solid was removed by filtration, washed with water, then ether and dried in vacuo to give 0.11 g of the title compound, mp 209°–212° C.

EXAMPLE QQ (S)-N-Ethyl-3-pyrrolidinemethanamine dihydrochloride

[3R-(R*,R*)] and [3S-(R*,S*)]-5-Oxo-1-(1-phenylethyl)-3-pyrrolidinecarboxylic Acid A mixture of 13.10 g (0.1 mole) itaconic acid and 12.12 g (0.1 mole) R(+)-α-methylbenzylamine in 100 ml xylene was refluxed overnight, cooled to room temperature, and filtered to afford 14.76 g (63%) colorless crystals of the title compound as a mixture of diastereomers; $[\alpha]_D+113.6°$ C. (C, 1.16, ethanol).

Anal. calcd. for $C_{13}H_{15}NO_3$: C, 66.93; H, 6.48; N, 6.00. Found: C, 67.30; H, 6.24; N, 5.92.

[3R-(R*,R*)] and [3S-(R*,S*)]-methyl-5-oxo-1-(1-phenylethyl)-3-pyrrolidinecarboxylate A solution of 126.6 g (0.543 mole) [3R-(R*,R*)]- and [3S-(R*,S*)]-5-oxo-1-(1-phenylethyl)-3-pyrrolidine-carboxylic acid and 0.50 g p-toluenesulfonic acid in 1300 ml methanol was refluxed overnight. The solvent was evaporated and the residue taken up in dichloromethane, washed with 3×300 ml 1N NaOH solution, dried (MgSO4) and evaporated to afford 131.7 g of a mixture of diastereomeric esters. Chromatography on a column of silica gel with ethyl acetate-pentane (3:2) afforded 74.9 g (56%) of [3R-(R*,R*)]-methyl 5-oxo-1-(1-phenylethyl)-3-pyrrolidinecarboxylate as a liquid, $[\alpha]_D+84.1°$ (C, 1.06 methanol).

Anal. calcd. for $C_{14}H_{17}NO_3$: C, 68.00; H, 6.93; N, 5.66. Found: C, 67.74; H, 7.27; N 5.48.

Evaporation of later fractions afforded 38.3 g (29%) of [3S-(R*,S*)]-methyl 5-oxo-1-(1-phenylethyl)-3-pyrrolidinecarboxylic acid as colorless crystals, mp 69°–71° C., $[\alpha]_D+116.2°$ C. (C, 1.03, methanol).

Anal. calcd. for $C_{14}H_{17}NO_3$: C, 68.00; H, 6.93; N, 5.66. Found: C, 66.69; H, 6.94; N, 5.34.

[3R-(R*,R*)]-1-(1-Phenylethyl)-3-pyrrolidinemethanol

A solution of 10.0 g (0.5 mmol) [3R-(R*, R*)]-methyl 5-oxo-1-(-1-phenylethyl)-3-pyrrolidinecarboxylate in 75 ml dry tetrahydrofuran was added dropwise to a mixture of 6.50 g (171 mmol) lithium aluminum hydride in 100 ml tetrahydrofuran. The mixture was refluxed overnight, diluted with 50 ml tetrahydrofuran and treated dropwise with 6.5 ml water, 6.5 ml 15% sodium hydroxide and 19.5 ml water. Solids were removed by filtration and the filtrate was evaporated to a syrup which was dissolved in dichloromethane, dried (MgSO4), and reevaporated to give 8.06 g of crude crystalline product. Recrystallization from hexane afforded 7.25 g (87%) of the title compound, mp 86°–88° C. $[\alpha]_D+51.3°$ C. (C, 1.06, methanol).

Anal. calcd. for $C_{13}H_{19}NO$: C, 76.06; H, 9.33; N, 6.82. Found: C, 76.38; H, 9.63; N, 7.05.

[3R-(R*,R*)]-3-Chloromethyl-1-(1-phenylethyl)pyrrolidine

A solution of 0.50 g (2.44 mmol) [3R-(R*,R*)]-1-(1-phenylethyl)-3-pyrrolidinemethanol in 5 ml 1,2-dichloroethane was treated with 2 ml thionyl chloride, refluxed two hours, evaporated, and crystallized by trituration with ether to afford 0.64 g (100%) of the title compound as the hydrochloride, mp 140°–146° C., $[\alpha]_D+27.8°$ C. (c, 1.07, methanol).

Anal. calcd. for $C_{13}H_{19}Cl_2N$: C, 60.00; H, 7.36; N, 5.38; Cl, 27.25. Found: C, 59.75; H, 7.09; N, 5.25; Cl, 26.94.

[3S-(R*,S*)]-N-Ethyl-1-(1-phenylethyl)-3-pyrrolidinemethanamine

A solution of 4.0 g (15.4 mmol) [3R-(R*,R*)]-3-(chloromethyl)-1-(1-phenylethyl)pyrrolidine in 60 ml 70% ethylamine was heated in a pressure bottle on the steam bath overnight. The mixture was cooled, filtered, and evaporated to a thick syrup which was treated with 50 ml 2N sodium hydroxide and extracted with 3×30 ml dichloromethane. The combined organic layer was dried (MgSO4) and evaporated to afford 3.49 g (98%) of the title compound as a syrup, $[\alpha]_D+45.6°$ C. (C, 1.04, methanol).

Anal. calcd. for $C_{15}H_{24}N_2$: C, 77.53; H, 10.41; N, 12.06. Found: C, 77.14; H, 10.23; N, 11.91.

(S)-N-Ethyl-3-pyrrolidinemethanmine Dihydrochloride

A solution of 5.97 g (25.7 mmol) [3S-(R*,S*)]-N-ethyl-1-(1-phenylethyl)-3-pyrrolidinemethanamine in 100 ml methanol with 0.6 g 20% Pd/C catalyst was hydrogenated at 50 psi for 23 hours. More catalyst (0.6 g) was added and the reaction continued an additional 23 hours. After filtration and evaporation of solvent the product was distilled to afford 2.05 g (62%) of the title compound as the free base, bp 74° C. (8 mm Hg). A sample (0.25 g) dissolved in 10 ml ether was treated with 1 ml 6N hydrogen chloride in 2-propanol to afford 0.29 g of the amine dihydrochloride after two crystallizations from ethanol, mp 184.5°–185.5° C., $[\alpha]_D+5.4°$ C. (C, 0.85, 0.1N NaOH).

EXAMPLE RR

N,N-Dimethyl-3-pyrrolidinemethanamine

N,N-Dimethyl-5-oxo-1-(phenylmethyl)-3-pyrrolidinecarboxamide

A mixture of 15.0 g (64.3 mmol) of methyl-5-oxo-1-(phenylmethyl)pyrrolidine carboxylate [J. Org. Chem., 26, 1519 (1961)] and 100 ml of methyl alcohol was cooled to 0° C. for 0.5 hours. To this solution excess N,N-dimethylamine (approximately 50 g, 1.11 mole) was added. The reaction was stirred overnight and brought to room temperature. The mixture was concentrated under reduced pressure and chromatographed over silica using chloroform, hexane, 2-propanol (6:3:1) giving 4.91 g (31%) of N,N-dimethyl-5-oxo-1-(phenylmethyl)-3-pyrrolidinecarboxamide as a clear yellow oil. This material was used in the next step.

N,N-Dimethyl-1-(phenylmethyl)-3-pyrrolidinemethanamine

A solution of 2.91 g (11.8 mmol) N,N-dimethyl-5-oxo-1-(phenylmethyl)-3-pyrrolidinecarboxamide and 15 ml anhydrous tetrahydrofuran was dropped into a suspension of 1.41 g (35 mmol) lithium aluminum hydride and 30 ml tetrahydrofuran The reaction was refluxed overnight then cooled to room temperature. To the solution was added 1.5 ml water, 1.5 ml 15% sodium hydroxide and 4.5 ml of water. The resulting precipitate was filtered The filtrate was concentrated under reduced pressure, dissolved in dichlromethane, dried over magnesium sulfate and the solvent evaporated under reduced pressure. The residue was bulb to bulb distilled giving 1.5 g (58%) of N,N-dimethyl-1-(phenylmethyl)-3-pyrrolidinemethanamine as a clear liquid. This material was used in the next step.

N,N-Dimethyl-3-pyrrolidinemethanamine

A mixture of 1.25 g (5.72 mmol) of N,N-dimethyl-1-(phenylmethyl)-3-pyrrolidinemethanamine, 100 ml of methyl alcohol, 0.2 g of 20% palladium on carbon and hydrogen were shaken at a pressure of 55.1 psi. After 16.8 hours the catalyst was filtered and the filtrate evaporated under reduced pressure. The residue was bulb to bulb distilled yielding 0.71 g (97%) N,N-dimethyl-3-pyrrolidinemethanamine as a clear yellow oil.

EXAMPLE SS

N,N-Diethyl-3-pyrrolidinemethanamine

N,N-Diethyl-1-(phenylmethyl)-3-pyrrolidinemethanamine

To a solution of 32.9 g (0.15 mole) 5-oxo-1-(phenylmethyl)-3-pyrrolidinecarboxylic acid [J. Org. Chem., 26, 1519 (1961)] and 300 ml of dichloromethane was added 15.2 g (0.15 mole) of N-methylmorpholine. After 15 minutes the solution was cooled to $-25°$ C. and 16.3 g (0.15 mole) of ethyl chloroformate was added. After an additional ten minutes, a solution of 13.5 g (0.18 mole) of diethylamine and 18 ml dichloromethane was added to the reaction. Carbon dioxide was evolved and after 1.5 h another 10 g (0.13 mole) of diethylamine in 10 ml of dichloromethane was added. The reaction was stirred four hours, washed with 1N sodium hydroxide, dried over magnesium sulfate, and concentrated under reduced pressure. The residue was added to a suspension of 17.4 g (0.46 mole) of lithium aluminum hydride and 210 ml anhydrous tetrahydrofuran. The reaction was refluxed overnight then cooled to room temperature. The cooled solution was quenched with 17.4 ml water, 17.4 ml 15% sodium hydroxide, and 52.2 ml water. The resulting precipitate was filtered and washed with ethyl alcohol. The filtrate was concentrated under reduced pressure, taken up in dichloromethane, dried over magnesium sulfate. The solvent was removed under vacuum giving 25.8 g (69%) of N,N-diethyl-1-(phenylmethyl)-3-pyrrolidinemethanamine as a yellow oil. This material was used in the next step without purification.

N,N-Diethyl-3-pyrrolidinemethanamine

A mixture of 25.4 g (0.10 mole) of N,N-diethyl-1-(phenylmethyl)-3-pyrrolidinemethanamine, 200 ml of methyl alcohol, 2 g of palladium on carbon and hydrogen were shaken at a pressure of 51.5 psi. After 20.3 hours, the catalyst was filtered and the filtrate concentrated under reduced pressure. The residue was bulb to bulb distilled giving 15.9 g of N,N-diethyl-3-pyrrolidinemethanamine.

EXAMPLE TT

3-(Ethylamino)pyrrolidine

To 12.7 g (72 mmol) of the 3-amino-1-(phenylmethyl)pyrrolidine in 25 ml of acetic acid was added 75 ml of acetic anhydride and the mixture refluxed for four hours. The reaction was concentrated, taken into water, and extracted with ether at pH 11. The ether was dried (magnesium sulfate) and concentrated to give 10.93 g of an oil. This material was taken directly into dry tetrahydrofuran and added dropwise to 7.0 g (184 mmol) of lithium aluminum hydride in 75 ml of tetrahydrofuran at 10° C. The mixture was refluxed for 18 hours, cooled to room temperature, and the treated sequentially with 7.0 ml of water, 7.0 ml of 15% sodium hydroxide, and 21.0 ml of water. The mixture was filtered, concentrated, taken up in dichloromethane, dried (magnesium sulfate), concentrated, and distilled in vacuo to give 8.30 g of 3-(ethylamino)-1-(phenylmethyl)pyrrolidine. This product was treated with 1.0 g of 20% palladium on charcoal in 100 ml of methanol and hydrogenated at 51.4 psi. After 24 hours, the mixture was filtered, concentrated, and distilled to give 2.1 g of 3-(ethylamino)pyrrolidine.

EXAMPLE UU

2-[(t-Butoxycarbonylamino)methyl]azetidine

1-Benzyl-2-[(t-butoxycarbonylamino)methyl]azetidine

To a solution of 14.4 g (82.0 mmol) of 1-benzyl-2-(aminomethyl)azetidine [French Patent No. 79-00258; C.A. 94:208573n (1981)], 90 ml of 1N sodium hydroxide, and 125 ml of tertiary butyl alcohol was added, dropwise, 19.64 g (90 mmol) of di-tert-butyl dicarbonate keeping the temperature below 60° C. When the addition was completed, the reaction was heated at 60° for three hours and then at room temperature for 18 hours. The solvent was removed in vacuo and the residue was partitioned between chloroform and water. The organic layer was washed with water, dried (MgSO$_4$), and evaporated in vacuo to give 19.3 g (95%) of the title compound as a pale yellow oil, which was used without further purification.

2-[(t-Butoxycarbonylamino)methyl]azetidine

A suspension of 18.8 g (68.0 mmol) of 1-benzyl-2-[(t-butoxycarbonylamino)methyl]azetidine, 8.2 g (137 mmol) of acetic acid, 1.0 g of 20% palladium on carbon and 200 ml of tetrahydrofuran was shaken in a hydrogen atmosphere at pressures of 48.3–51.7 psi and temperatures of 21.5°–27° for 16 hours. The catalyst was removed by filtration and the solvent was removed in vacuo to give 11.7 g (92%) of the title compound as a colorless viscous oil which was used without further purification.

EXAMPLE VV 6,7,8-Trifluoro-1,4-dihydro-1-(1-methylcyclopropyl)-4-oxo-3-quinolinecarboxylic Acid To 3.0 g (11.33 mmol) of the 2,3,4,5-tetrafluoro-β-oxo-benzenepropanoic acid, ethyl ester was added 2.76 g of acetic anhydride and 2.5 g of triethylorthoformate. These were refluxed for 2.5 hours and concentrated under high vacuum at 80° C. The residual oil was treated at 45° C. with 1.33 g (1.1 equivalents) of 1-amino-1-methylcyclopropane hydrochloride (U.S. Pat. No. 3,451,802) in 50 ml of t-butanol. To this mixture was added 1.43 g (1.1 equivalents) of potassium t-butoxide in 20 ml t-butanol. After 24 hours the mixture was treated with an additional 1.1 equivalents of potassium t-butoxide in 20 ml of t-butanol and was heated to 75° for 24 hours. The reaction was cooled, partially concentrated, and filtered. The solids were dissolved in 75 ml of hot acetic acid and 25 ml of 3N hydrochloric acid was added in portions over two hours at 100° C. The reaction was maintained at this temperature for two additional hours and 20 ml of water was added. The mixture was cooled and filtered to give 2.0 g of 6,7,8-trifluoro-1,4-dihydro-1-(1-methylcyclopropyl)-4-oxo-3-quinolinecarboxylic acid, mp 292°-294° C.

EXAMPLE WW 6,7,8-Trifluoro-1,4-dihydro-1-(2-methylcyclopropyl)-4-oxo-3-quinolinecarboxylic Acid Using the procedure of Example VV with 2-methylcyclopropylamine (prepared as in U.S. Pat. No. 3,451,802) 3.0 g (11.33 mmol) of 2,3,4,5-tetrafluoro-β-oxo-benzenepropanoic acid, ethyl ester was converted to 1.79 g of 6,7,8-trifluoro-1,4-dihydro-1-(2-methylcyclopropyl)-4-oxo-3-quinolinecarboxylic acid as a mixture of isomers, mp 167°-168° C.

EXAMPLE XX 6,7,8-Trifluoro-1-(2,2,2-trifluoroethyl)-1,4-dihydro-4-oxo-3-quinolinecarboxylic Acid Using the procedure of Example VV with 2,2,2-trifluoroethylamine, 3.0 g (11.33 mmol) of 2,3,4,5-tetrafluoro-β-oxo-benzenepropanoic acid, ethyl ester was converted to 1.28 g of the 6,7,8-trifluoro-1-(2,2,2-trifluoroethyl)-1,4-dihydro-4-oxo-3-quinolinecarboxylic acid, mp 205°-207° C.

EXAMPLE YY 1-(Cyclopropylmethyl)-6,7,8-trifluoro-1,4-dihydro-4-oxo-3-quinolinecarboxylic Acid Using the procedure of Example VV with cyclopropylmethylamine, 3.0 g (11.33 mmol) of 2,3,4,5-tetrafluoro-β-oxo-benzenepropanoic acid, ethyl ester was converted to 1.31 g of 1-(cyclopropylmethyl)-6,7,8-trifluoro-1,4-dihydro-4oxo-3-quinolinecarboxylic acid, mp 223°-255° C. (slow decomposition).

EXAMPLE ZZ 6,7,8-Trifluoro-1,4-dihydro-1-(1-methylethyl)-4-oxo--quinolinecarboxylic Acid Using the procedure of Example VV with isopropyl amine, 3.0 g (11.33 mmol) of 2,3,4,5-tetrafluoro-β-oxo-benzeneproprionic acid, ethyl ester was converted to 1.21 g of 6,7,8-trifluoro-1,4-dihydro-1-(1-methylethyl)-4oxo-3-quinolinecarboxylic acid, mp 256°-260° C.

EXAMPLE AAA

1-Cyclopentyl-6,7,8-trifluoro-1,4-dihydro-4-oxo-3-quinolinecarboxylic Acid

Using the procedure of Example VV with cyclopentyl amine, 3.0 g (11.33 mmol) of 2,3,4,5-tetrafluoro-β-oxo-benzenepropanoic acid, ethyl ester was converted to 1.63 g of 1-cyclopentyl-6,7,8-trifluoro-1,4-dihydro-4-oxo-3-quinolinecarboxylic acid, mp 206°-207° C.

EXAMPLE BBB

1-Cyclohexyl-6,7,8-trifluoro-1,4-dihydro-4-oxo-3-quinolinecarboxylic Acid

Using the procedure of Example VV with cyclohexylamine, 3.0 g (11.33 mmol) of 2,3,4,5-tetrafluoro-β-oxo-benzenepropanoic acid, ethyl ester was converted to 2.13 g of 1-cyclo-hexyl-6,7,8-trifluoro-1,4-dihydro-4-oxo-3-quinolinecarboxylic acid, mp 261°-264° C.

EXAMPLE CCC

1-Cyclobutyl-6,7,8-trifluoro-1,4-dihydro-4-oxo-3-quinolinecarboxylic Acid

Using the procedure of Example VV with cyclobutylamine, 3.0 g (11.33 mmol) of 2,3,4,5-tetrafluoro-β-oxo-benzenepropanoic acid, ethyl ester, was converted to 1.01 g of 1-cyclobutyl-6,7,8-trifluoro-1,4-dihydro-4-oxo-3-quinolinecarboxylic acid, mp 192°-194° C.

We claim:

1. A compound of the formula

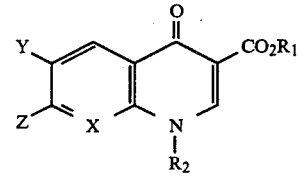

wherein
Z is

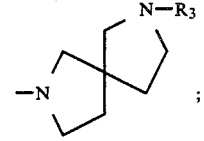

X is CH, CCl, CF, CO-alkyl having from one to three carbon atoms, C—NH—alkyl having from one to three carbon atoms or N;

Y is hydrogen, fluorine, chlorine, or bromine;

$R_1$ is hydrogen, alkyl having from one to six carbon atoms or a cation;

$R_2$ is alkyl having from one to four carbon atoms, vinyl, haloalkyl, or hydroxyalkyl having from two to four carbon atoms or cycloalkyl having three to six carbon atoms;

$R_3$ is hydrogen, alkyl having from one to four carbon atom or cycloalkyl having three to six carbon atoms or a pharmaceutically acceptable acid addition or base salt thereof.

2. A compound as claimed in claim 1, wherein Y is fluorine.

3. A compound as claimed in claim 2, wherein $R_2$ is ethyl, vinyl, or 2-fluoroethyl.

4. A compound as claimed in claim 3, wherein X is CH, CF, or N.

5. A compound as claimed in claim 4, wherein $R_1$ is hydrogen or a pharmaceutically acceptable base salt thereof.

6. A compound as claimed in claim 1, wherein Z is

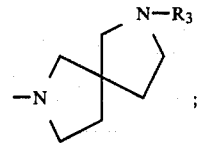

X is C—F or N, and $R_3$ is hydrogen, methyl, or ethyl.

7. A compound as claimed in claim 6 and being 1-ethyl-6-fluoro-1,4-dihydro-7-(7-methyl-2,7-diazaspiro[4.4]non-2-yl)-4-oxo-1,8-naphthyridine-3-carboxylic acid.

8. A compound as claimed in claim 6 and being 1-ethyl-6,8-difluoro-1,4-dihydro-7-(7-methyl-2,7diazaspiro[4.4]non-2-yl)-4-oxo-3-quinolinecarboxylic acid.

* * * * *